United States Patent
Klencke et al.

(10) Patent No.: US 11,963,962 B2
(45) Date of Patent: Apr. 23, 2024

(54) PLATELET COUNT-AGNOSTIC METHODS OF TREATING MYELOFIBROSIS

(71) Applicant: Sierra Oncology, Inc., Plymouth, MI (US)

(72) Inventors: Barbara Jane Klencke, Plymouth, MI (US); Gregg David Smith, Plymouth, MI (US); Rafe Michael Joseph Donahue, Plymouth, MI (US)

(73) Assignee: GLAXOSMITHKLINE LLC, Wilmington, DE (US)

( * ) Notice: Subject to any disclaimer, the term of this patent is extended or adjusted under 35 U.S.C. 154(b) by 469 days.

(21) Appl. No.: 17/266,262

(22) PCT Filed: Aug. 21, 2019

(86) PCT No.: PCT/US2019/047499
§ 371 (c)(1),
(2) Date: Feb. 5, 2021

(87) PCT Pub. No.: WO2020/041466
PCT Pub. Date: Feb. 27, 2020

(65) Prior Publication Data
US 2021/0299132 A1 Sep. 30, 2021

Related U.S. Application Data

(60) Provisional application No. 62/774,752, filed on Dec. 3, 2018, provisional application No. 62/749,052, filed on Oct. 22, 2018, provisional application No. 62/720,782, filed on Aug. 21, 2018.

(51) Int. Cl.
*A61K 31/5377* (2006.01)
*A61K 9/00* (2006.01)
*A61P 35/00* (2006.01)

(52) U.S. Cl.
CPC ........ *A61K 31/5377* (2013.01); *A61K 9/0053* (2013.01); *A61P 35/00* (2018.01)

(58) Field of Classification Search
CPC ................................................. A61K 31/5377
See application file for complete search history.

(56) References Cited

U.S. PATENT DOCUMENTS

| | | | |
|---|---|---|---|
| 2014/0073643 A1 | 3/2014 | Smith et al. | |
| 2018/0042933 A1 | 2/2018 | Koh et al. | |

FOREIGN PATENT DOCUMENTS

| | | |
|---|---|---|
| JP | 2016537433 | 12/2016 |
| JP | 2017517535 | 6/2017 |
| WO | WO 2008109943 | 9/2008 |
| WO | WO 2012071612 | 6/2012 |
| WO | WO 2015/081127 | 6/2015 |
| WO | WO 2015191846 | 12/2015 |
| WO | WO 2018031579 | 2/2018 |

OTHER PUBLICATIONS

Al-Ali et al., "Managing patients with myelofibrosis and low platelet counts," Annals of Hematology, May 21, 2016, 96:537-548.
Bose et al., "Management of Myelofibrosis-Related Cytopenias," Current Hematologic Malignancy Reports, May 23, 2018, 12:164-172.
Cervantes et al., "Newprognostic scoring system for primary myelofibrosis based on a study of the International Working Group for Myelofibrosis Research and Treatment," Blood, Mar. 26, 2009, 113(13):2895-2901.
ClinicalTrials.gov[online], "Efficacy of Momelotinib Versus Best Available Therapy in Anemic or Thrombocytopeniabjects With Primary Myelofibrosis (MF), Post-polycythemia Vera MF, or Post-essential Thrombocythemia MF (Simplify 2)," NCT02101268, Apr. 2, 2014, retrieved on Jul. 13, 2022, retrieved from URL<https://clinicaltrials.gov/ct2/show/NCT02101268>, 11 pages.
ClinicalTrials.gov[online], "Momelotinib Versus Ruxolitinib in Subjects With Myelofibrosis (Simplify 1)," NCT01969838, Apr. 15, 2020, retrieved on Jul. 13, 2022, retrieved from URL<https://clinicaltrials.gov/ct2/show/NCT01969838>, 8 pages.
Extended Search Report in European Application No. 19851119.8, dated Apr. 19, 2022, 12 pages.
Gangat et al., "DIPSS Plus: A Refined Dynamic International Prognostic Scoring System for Primary Myelofibrosis That Incorporates Prognostic Information From Karyotype, Platelet Count, and Transfusion Status," J. Clin. Oncol., Feb. 1, 2011, 29(4):392-397.
Ganz et al., "Systemic Iron Homeostasis," Physiol Rev. 2013, 93:1721-1741.
Gwaltney et al., "Development of a harmonized patient-reported outcome questionnaire to assess myelofibrosis symptoms in clinical trials," Leukemia Research, Aug. 2017, 59:26-31.
Harrison et al., "Momelotinib versus best available therapy in patients with myelofibrosis previously treated with ruxolitinib (Simplify 2): a randomised, open-label, phase 3 trial," Lancet Haematol, Feb. 2018, 5(2):e73-e81.

(Continued)

*Primary Examiner* — Golam M Shameem
(74) *Attorney, Agent, or Firm* — Fish & Richardson P.C.

(57) ABSTRACT

Reanalysis of the SIMPLIFY 1 and 2 trials data indicates MMB is effective in JAKi-naïve patients and in second line therapy to RUX, providing benefits of reducing enlarged spleens, improving myelofibrosis-related symptoms, and increasing transfusion independence in patient at risk for thrombocytopenia from the underlying disease and RUX therapy. Accordingly, methods of treating myeloproliferative neoplasms (MPN) such as myelofibrosis are described. The methods can include administering a therapeutically effective amount of momelotinib or a pharmaceutically acceptable salt thereof to a subject identified as having (i) myelofibrosis and (ii) a platelet count of less than $150 \times 10^9$/L. Also described are methods including administering to a subject with myelofibrosis a therapeutically effective stable dose of momelotinib or a pharmaceutically acceptable salt thereof, for a period of a plurality of weeks, where the subject is assessed as maintaining a platelet count above a predetermined threshold platelet count during the period.

21 Claims, 47 Drawing Sheets

(56) References Cited

OTHER PUBLICATIONS

Harrison et al., "Ruxolitinib is effective in patients with intermediate-1 risk myelofibrosis: a summary of recent evidence," Leukemia & Lymphoma, Oct. 2, 2016, 57(10):2259-2267.
Hobbs et al., "New drugs for myelofibrosis," Expert Opinion on Orphan Drugs, Apr. 8, 2016, 4(5):521-529.
Langdon et al., "Hepcidin-dependent and hepcidin-independent regulation of erythropoiesis in a mouse model of anemia of chronic inflammation", Am J Hematol. May 2014, 89(5):470-9.
Oh et al., "Hepcidin Suppression by Momelotinib is Associated with Increased Iron Availability and Erythropoiesis in Transfusion-Dependent Myelofibrosis Patients (Abstract)," Blood, Nov. 29, 2018, 132(1).
Pardanani et al., "Associations and prognostic interactions between circulating levels of hepcidin, ferritin and inflammatory cytokines in primary myelofibrosis." Am J Hematol., Feb. 6, 2013, 88:312-6.
Passamonti et al., "Adynamic prognostic model to predict survival in primary myelofibrosis: a study by the IWG-MRT(International Working Group for Myeloproliferative Neoplasms Research and Treatment)," Blood, Mar. 4, 2010, 115(9):1703-1708.
Pettit et al., "Novel therapies for myelofibrosis," Current Hematologic Malignancy Reports, Nov. 2, 2017, 12(6):615-617.
Tefferi et al., "One Thousand Patients With Primary Myelofibrosis: The Mayo Clinic Experience," Mayo Clin. Proc., Jan. 2012; 87(1):25-33.
Tefferi et al., "Revised cytogenetic risk stratification in primary myelofibrosis: analysis based on 1002 informative patients," Leukemia, May 2018, 32(5): 1189-1199.
Vannucchi et al., "Advances in Understanding and Management of Myeloproliferative Neoplasms," CA Cancer J. Clin., Apr. 16, 2009, 59: 171-191.
Vannucchi et al., "Mutation-Enhanced International Prognostic Scoring System (MIPSS) for Primary Myelofibrosis: An AGIMM & IWG-MRT Project," Blood, Dec. 6, 2014; 124(21):405.
International Search Report and Written Opinion of International Application No. PCT/US2019/047499, dated Oct. 25, 2019 (7 pages).
Mesa et al., "Simplify-1: A Phase III Randomized Trial of Momelotinib Versus Ruxolitinib in Janus Kinase Inhibitor—Naïve Patients With Myelofibrosis," J Clin Oncol vol. 35, No. 34, pp. 3844-3850 (Dec. 2017).
Harrison et al., "Janus kinase-2 inhibitor fedratinib in patients with myelofibrosis previously treated with ruxolitinib (JAKARTA-2): a single-arm, open-label, non-randomised, phase 2, multicentre study," Lancet Haematol., Jul. 2017, 4(7):e317-e324.
Bose et al., "Management of Myelofibrosis-Related Cytopenias," Current Hematologic Malignancy Reports, May 23, 2018, 13(3):164-172.
Pardanani et al., "Genetic determinants of response and survival in momelotinib-treated patients with myelofibrosis," Leukemia, Mar. 2015, 29(3):741-744.
International Preliminary Report on Patentability in International Appln. No. PCT/US2019/047499, dated Mar. 4, 2021, 6 pages.

| | Momelotinib (MMB) | Ruxolitinib (RUX) | Fedratinib (FED) | Pacritinib (PAC) |
|---|---|---|---|---|
| Status in Myelofibrosis | Phase 3 (2x completed P3s; P2 translational biology) | Approved (intermediate / high-risk; platelets ≥50 × 10³/dL) | Post-Phase 3 (NDA filing 2018 TBD) | Phase 2 (P3 trial requested by FDA; EU MAA refiled) |
| Targets | JAK1, JAK2, ACVR1 | JAK1, JAK2 | JAK2, FLT3 | JAK2, FLT3 |
| Splenic Response | ✓ | ✓ | ✓ | ✓ |
| Symptom Benefit | ✓ | ✓ | ✓ | ✓ |
| Anemia Benefit | ✓ | ✗ | ✗ | ✗ |
| Toxicity: Anemia & Thrombocytopenia | LOW | HIGH | HIGH | HIGH |

FIG. 7

PLATELET COUNT-AGNOSTIC METHODS OF TREATING MYELOFIBROSIS

CROSS REFERENCE

This application is a national phase entry pursuant to 35 U.S.C. § 371 of International Application No. PCT/US2019/047499, filed Aug. 21, 2019, which claims the benefit of U.S. Provisional Application No. 62/720,782, filed Aug. 21, 2018, U.S. Provisional Application No. 62/749,052, filed Oct. 22, 2018 and U.S. Provisional Application No. 62/774,752, filed Dec. 3, 2018, each of which is incorporated by reference herein in its entirety.

BACKGROUND

Myelofibrosis (MF) is a disease that affects approximately 40,000 to 50,000 patients worldwide, of which 70-80% of patients are categorized as intermediate to high risk MF patients. The median survival for all patients with MF is about 6 years, but is considerably worse for patients classified as intermediate-2 or high-risk MF, at 4 years and 2.25 years, respectively.

Myelofibrosis may occur de novo as Primary MF (PMF) or may arise from a pre-existing myeloproliferative neoplasm (MPN), primarily polycythemia vera (PV) or essential thrombocythemia (ET). Once these conditions reach the overtly fibrotic stage, they are virtually indistinguishable clinically.

The three cardinal disease manifestations of MF are (1) anemia, often in association with thrombocytopenia or other cytopenias; (2) constitutional symptoms, such as fatigue, night sweats, fever, cachexia, bone pain, pruritus, and weight loss; and (3) organomegaly due to extramedullary hematopoiesis, principally of the spleen and less often the liver, which can cause commonly associated symptoms such as abdominal distension and pain, early satiety, dyspnea, and diarrhea.

Ruxolitinib (RUX) is a Janus kinase (JAK) inhibitor used for the treatment of intermediate and high-risk myelofibrosis, including primary myelofibrosis, post-polycythemia vera myelofibrosis and post-essential thrombocythemia myelofibrosis. Ruxolitinib is used for treating approximately 70% of presenting patients, but is not approved for patients with severe thrombocytopenia.

In addition, treatment with ruxolitinib can itself cause thrombocytopenia. In the two Phase 3 clinical trials of ruxolitinib, patients with a platelet count of $100\times10^9$ to $200\times10^9$/L before starting ruxolitinib had a higher frequency of Grade 3 or 4 thrombocytopenia compared to patients with an entry platelet count greater than $200\times10^9$/L (17% versus 7%). In patients who developed Grade 3 or 4 thrombocytopenia, the median time to onset of thrombocytopenia was approximately 8 weeks. Thrombocytopenia was generally reversible with dose reduction or dose interruption. The median time to recovery of platelet counts above $50\times10^9$/L was 14 days.

In clinical practice, on-treatment thrombocytopenia is managed by reducing the dose or temporarily interrupting ruxolitinib treatment, with platelet transfusions as needed. Following discontinuation of ruxolitinib, symptoms from myeloproliferative neoplasms may return to pretreatment severity in as few as 7 days.

MF is a chronic, progressive, and invariably fatal disease. Ruxolitinib, the current standard of care, cannot be administered to 30% of presenting patients. Ruxolitinib itself causes thrombocytopenia and anemia, leading to dose reduction or interruption and recurrence of symptoms. Most patients need additional treatment after ruxolitinib therapy.

Unfortunately, the recently approved JAK2/FLT3 inhibitor fedratinib has a similar hematological toxicity profile to ruxolitinib and is to be administered only to patients with a baseline platelet count of $50\times10^9$/L or greater, with dose reduction for Grade 4 thrombocytopenia or other adverse events. Consequently, despite the availability of ruxolitinib and fedratinib, there continues to be a need for additional therapies for this fatal disease.

SUMMARY

Momelotinib (MMB) is a potent, selective, orally-bioavailable, small-molecule inhibitor of JAK1, JAK2 and activin A receptor, type I (ACVR1) that was developed for the treatment of myelofibrosis (MF). In two Phase three clinical trials for first-line and second-line treatment of MF (SIMPLIFY-1 and -2, respectively), however, MMB failed to meet one of the predefined primary or secondary endpoints in each of these two clinical trials.

In the SIMPLIFY-1 trial (NCT01969838), the efficacy and safety of MMB versus ruxolitinib (RUX) was studied in patients with myelofibrosis who were naïve to treatment with a JAK inhibitor and a platelet count of at least $50\times10^9$ per liter (/L). Patients (N=432) with high risk or intermediate-2 risk or symptomatic intermediate-1 risk myelofibrosis received 24 weeks of treatment with 200 mg MMB once daily or 20 mg RUX twice a day (or per label), after which all patients could receive open-label momelotinib. Efficacy was measured, with a goal of demonstrating non-inferiority of MMB to RUX, by spleen response, total symptom score (TSS), rate of red blood cell transfusion, and transfusion independence or transfusion dependence. The primary endpoint was a reduction by at least 35% in the spleen volume at 24 weeks compared with baseline.

An initial analysis of the results of the SIMPLIFY-1 trial was reported by Mesa et al. (SIMPLIFY-1: A Phase III Randomized Trial of Momelotinib Versus Ruxolitinib in Janus Kinase Inhibitor-Naive Patients with Myelofibrosis", J. Clinical Oncology 2017, 35(34):3844-3850). That analysis of the SIMPLIFY-1 trial data indicated momelotinib was noninferior to RUX for the reduction of spleen size in JAKi-naïve patients, thus meeting the study's primary endpoint. However, non-inferiority was not demonstrated for the secondary endpoint of total symptom score (TSS) response despite evidence of momelotinib's symptomatic benefits in symptomatic patients in that study. MMB treatment was associated with an increased transfusion independence rate, a decreased transfusion dependence rate and a reduced transfusion rate compared to RUX, all of which were nominally statistically-significant.

In the SIMPLIFY-2 trial (NCT02101268), the efficacy and safety of MMB versus best available treatment (BAT) was studied in anemic or thrombocytopenic subjects with myelofibrosis who were previously treated with ruxolitinib (RUX). There was no lower limit for a required baseline platelet count. Efficacy, with a goal of demonstrating superiority of MMB over BAT, was measured by spleen response, total symptom score (TSS), rate of red blood cell transfusion, and transfusion-independence or transfusion dependence. The primary endpoint was a reduction by at least 35% in the spleen volume at 24 weeks compared with baseline.

An initial analysis of the results of the SIMPLIFY-2 trial was reported by Harrison et al. ("Momelotinib versus best available therapy in patients with myelofibrosis previously treated with ruxolitinib (SIMPLIFY 2): a randomised, open-label, phase 3 trial." Lancet Haematol; Volume 5, Issue 2, February 2018, Pages e73-e81). That analysis of the SIMPLIFY-2 trial data indicated momelotinib was not superior to predominantly ruxolitinib BAT for the reduction of spleen size, thus the trial failed to achieve its primary endpoint and formal hierarchical statistical testing was ceased.

Nominal statistical significance was observed for the TSS response rate and transfusion independence rate versus BAT. A lower rate of transfusion dependence and decreased transfusion burden was also noted. The initial analysis was complicated by the failure to mandate discontinuation of ruxolitinib prior to the start of randomized study treatment. By not including a mandatory washout from prior ruxolitinib, the evaluation of the splenic response was obscured in this study in subjects in either arm. In addition, patients enrolled in this study were not selected based on splenic progression on RUX.

We have re-analyzed the data from the SIMPLIFY-1 and SIMPLIFY-2 trials and discovered that momelotinib is effective in reducing spleen size (SSR), improving total symptom scores (TSS), and improving transfusion independence rates in patients whose platelet counts are $150 \times 10^9$ per liter (/L) or below, without momelotinib administration causing thrombocytopenia, and without therefore requiring dose reduction or interruption for thrombocytopenia. Our reanalyses indicate that MMB is effective in JAKi-näive patients and in patients as a second line therapy to RUX, providing benefits of reducing enlarged spleens and improving myelofibrosis-related symptoms and improving transfusion independence rates in a patient population with or at risk for thrombocytopenia from the underlying disease and from current standard of care.

Accordingly, this disclosure describes methods of treating myeloproliferative neoplasms (MPN) such as myelofibrosis. In some embodiments, the method includes administering a therapeutically effective amount of momelotinib or a pharmaceutically acceptable salt thereof to a subject identified as having (i) myelofibrosis and (ii) a platelet count of less than $150 \times 10^9$/L. Also provided are methods of treating myeloproliferative neoplasms (MPN) such as myelofibrosis that include administering to a subject a therapeutically effective stable dose of momelotinib or a pharmaceutically acceptable salt thereof, for a period of a plurality of weeks, where the subject is assessed as maintaining a platelet count above a predetermined threshold platelet count during the treatment period.

BRIEF DESCRIPTION OF THE DRAWINGS

These and other features, aspects, and advantages of the present disclosure will become better understood with regard to the following description, and accompanying drawings.

FIG. 7 illustrates that momelotinib is a differentiated JAK inhibitor (JAKi). No other JAKi has consistently demonstrated a broader ability to address the needs of MF patients: Only momelotinib has robust spleen, symptom and anemia benefits. Momelotinib has been studied is over 20 Phase 1, 2 and 3 clinical studies, including dosing of over 1,200 patients. Over 550 myelofibrosis patients have been treated, and several patients have been on treatment for at least seven years. Momelotinib can provide a spectrum of robust benefits in MF, e.g., spleen, symptoms and anemia and is the only JAKi which is not associated with high rates of anemia and thrombocytopenia.

FIG. 8A: SIMPLIFY-1 study of MMB in a first line population previously untreated with JAKi. For SIMPLIFY-1, the goal was non-inferiority over ruxolitinib (RUX). FIG. 8B: SIMPLIFY-2 study of second line population of anemic or thrombocytopenic subjects previously treated with RUX. For SIMPLIFY-2, the goal was superiority over best available treatment (BAT).

DETAILED DESCRIPTION

Figure 1:
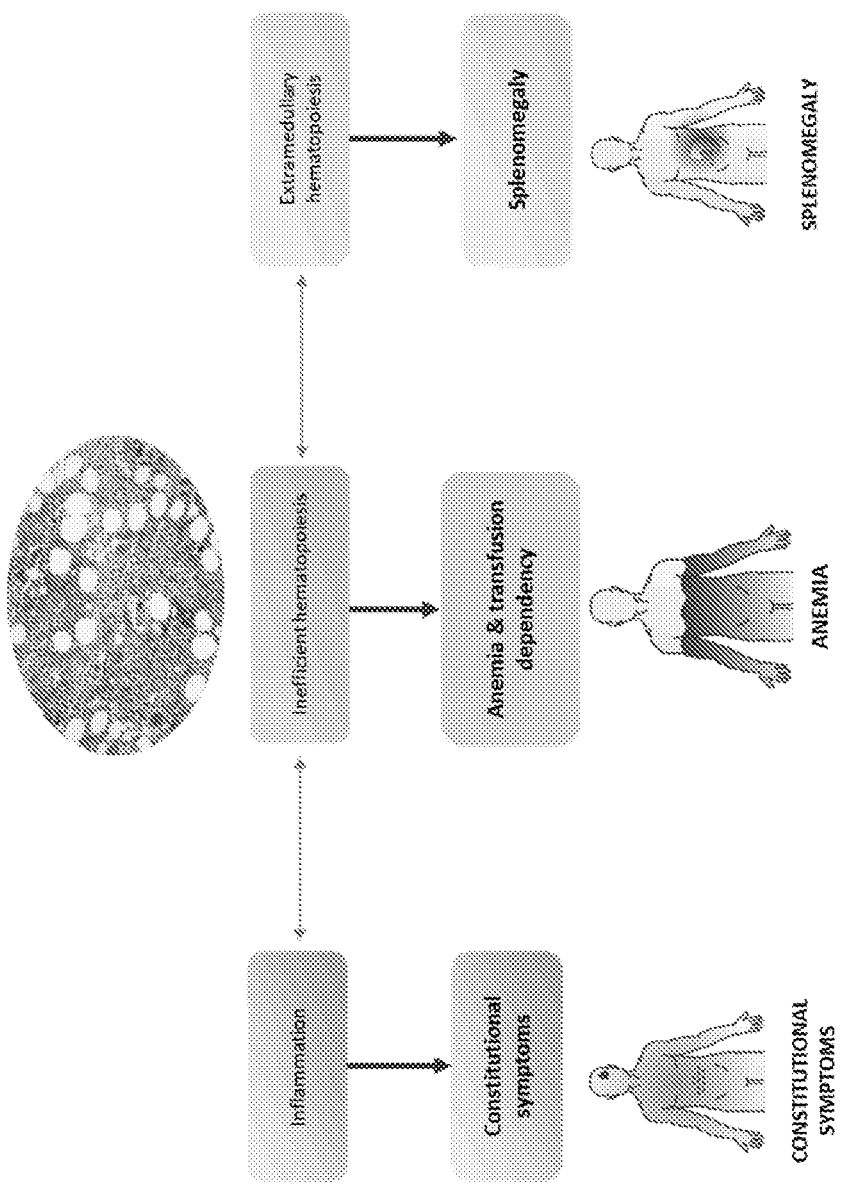
FIG. 1 shows a schematic related to characteristics of myelofibrosis, a chronic myeloproliferative neoplasm (MPN).
Figure 2:
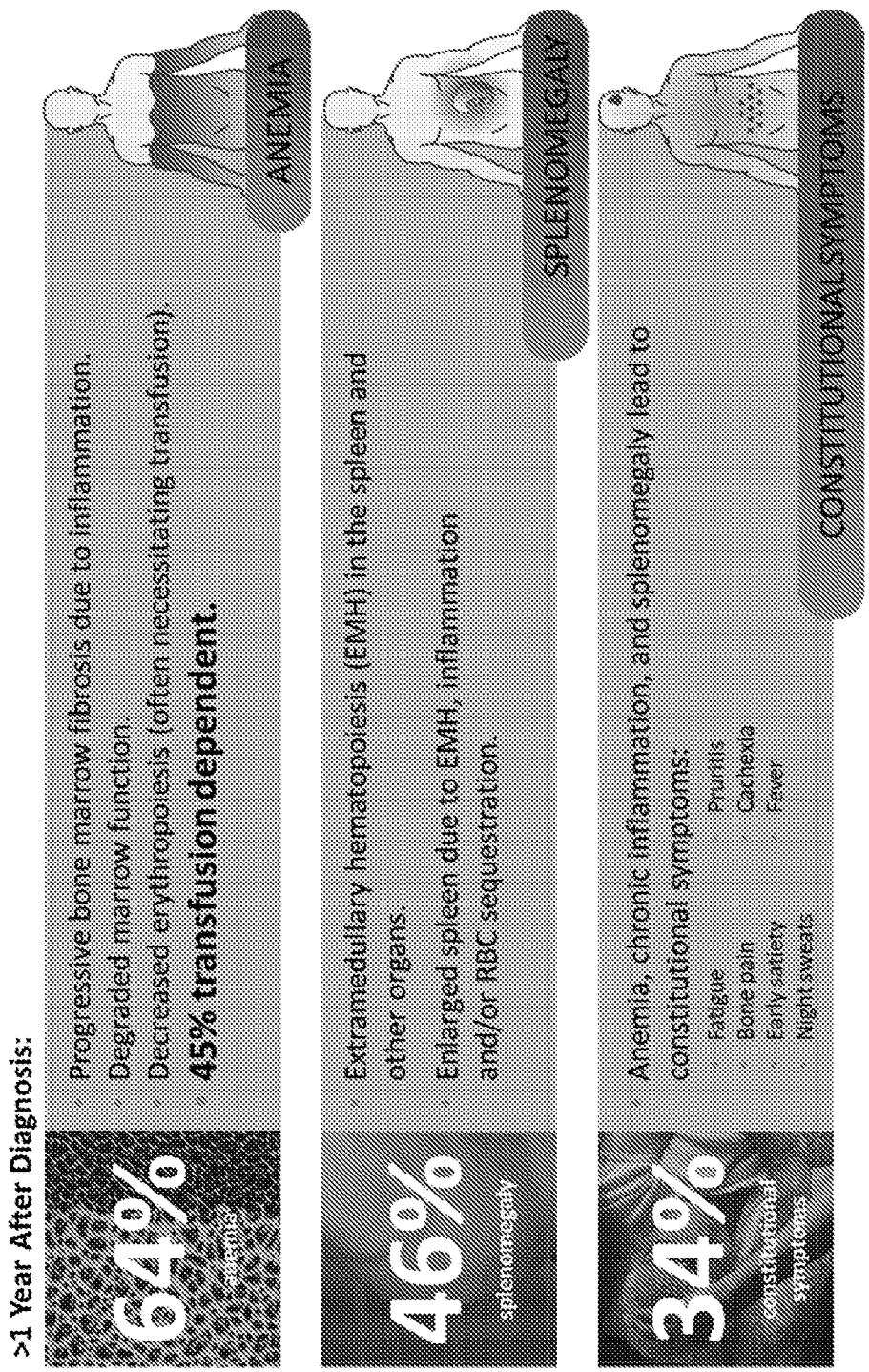
FIG. 2 shows a schematic illustrating three characteristics of disease for myelofibrosis and the proportion of patients who exhibit these manifestations one year after initial diagnosis. See Tefferi A et al. Mayo Clin. Proc. 2012; 87:25-33.
Figure 3:
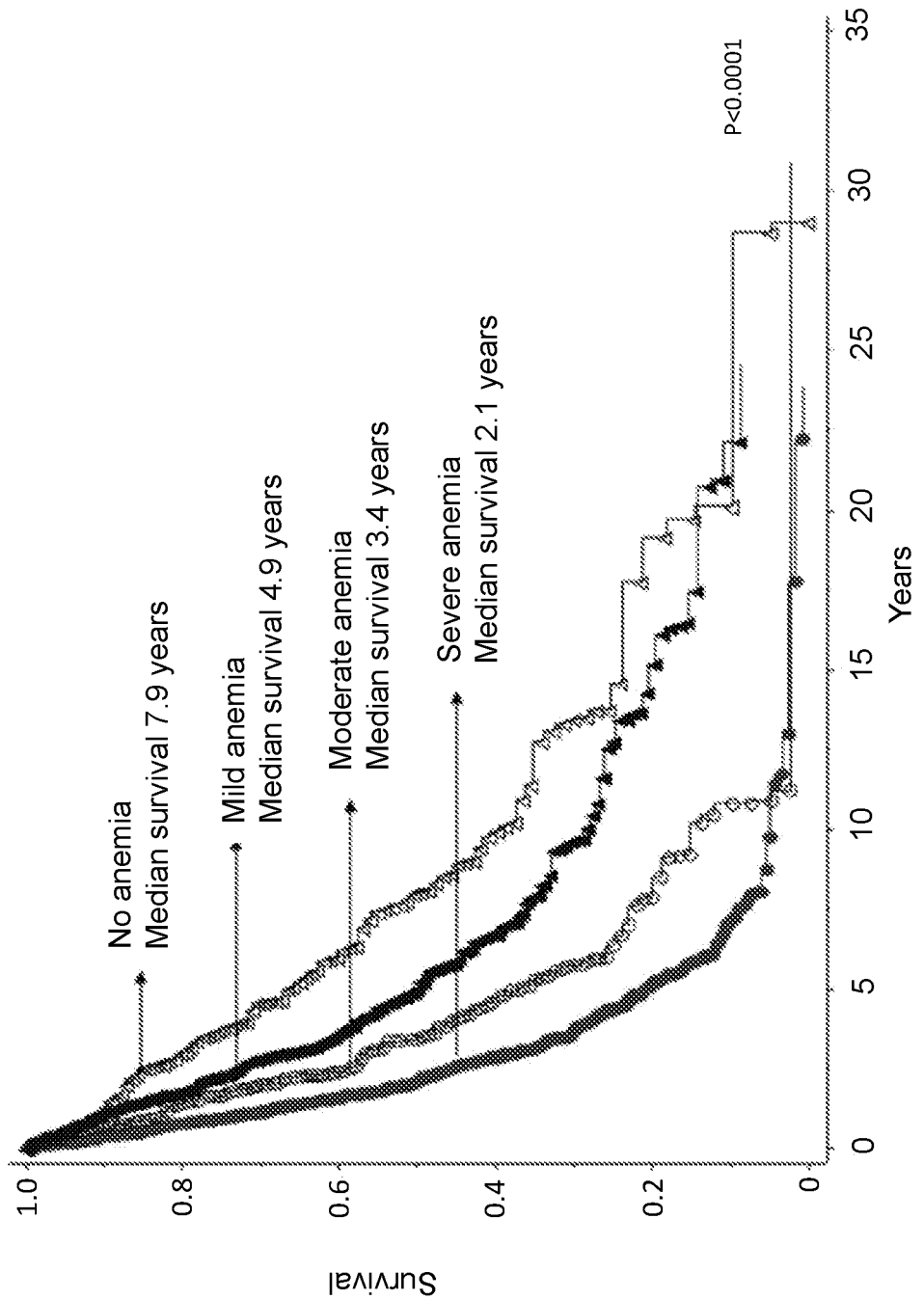
FIG. 3 shows a graph of survival rate over time for myelofibrosis subjects having mild, moderate or severe anemia versus no anemia, indicating anemia is an important prognostic factor. Baseline Anemia: Mild=Hgb≥10 g/dl but below lower limit of normal. Moderate=Hgb between 8 g/dl and <10 g/dl; Severe=Hgb<8 g/dl or transfusion dependent. See e.g., Nicolosi et al. *Leukemia* 2018 32(5):1189-1199.
Figure 4:
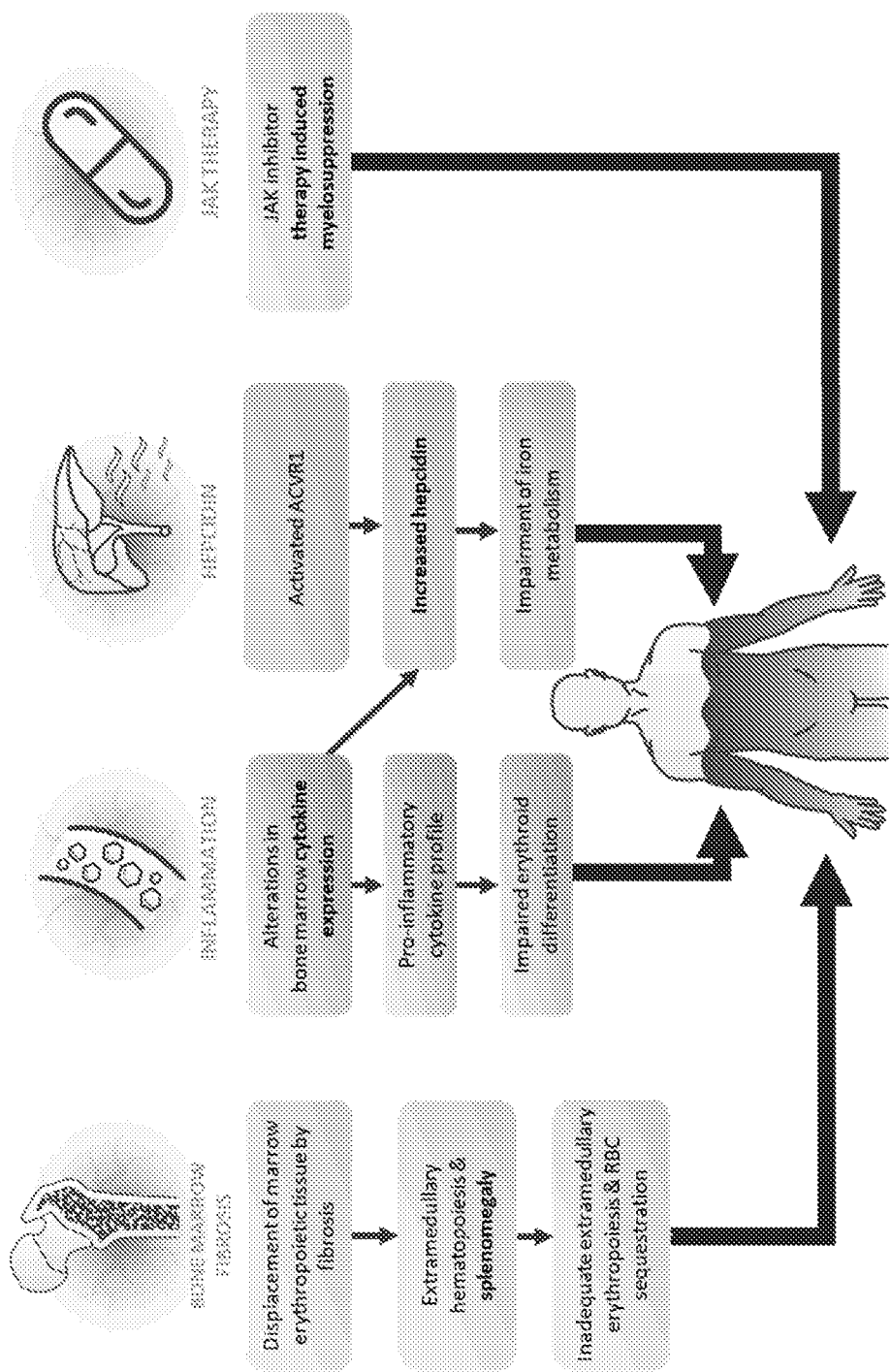
FIG. 4 shows a schematic that illustrates pathways to anemia in myelofibrosis.
Figure 5B:
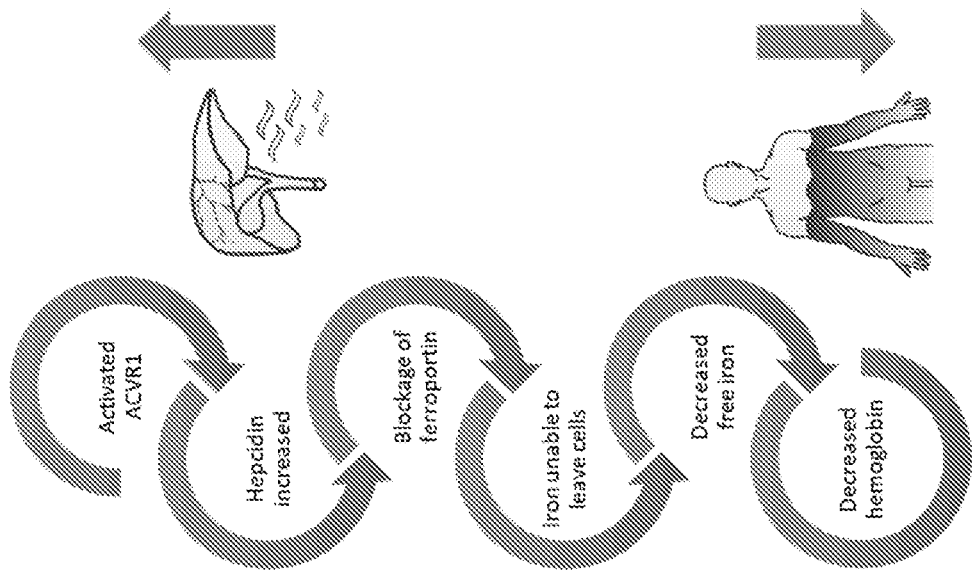
FIG. 5A-5B illustrates a biological basis for momelotinib's anemia benefit in subject's having myelofibrosis. ACVR1 and hepcidin: the iron metabolism pathway involves TGFβ superfamily receptors such as ACVR1; ACVR1 signals through Smads activating the transcription of hepcidin (FIG. 5A); and elevated hepcidin leads to decreased erythropoiesis (FIG. 5B). Other therapeutics targeting the TGFβ superfamily include luspatercept and sotatercept.
Figure 5A:
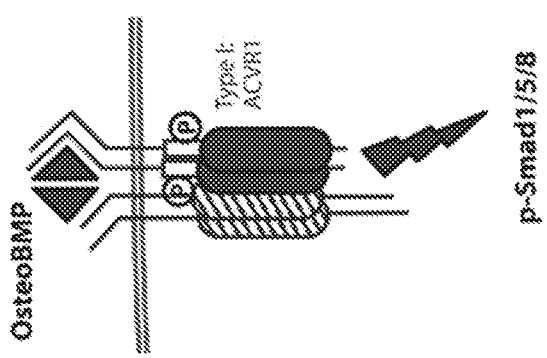
Figure 6:
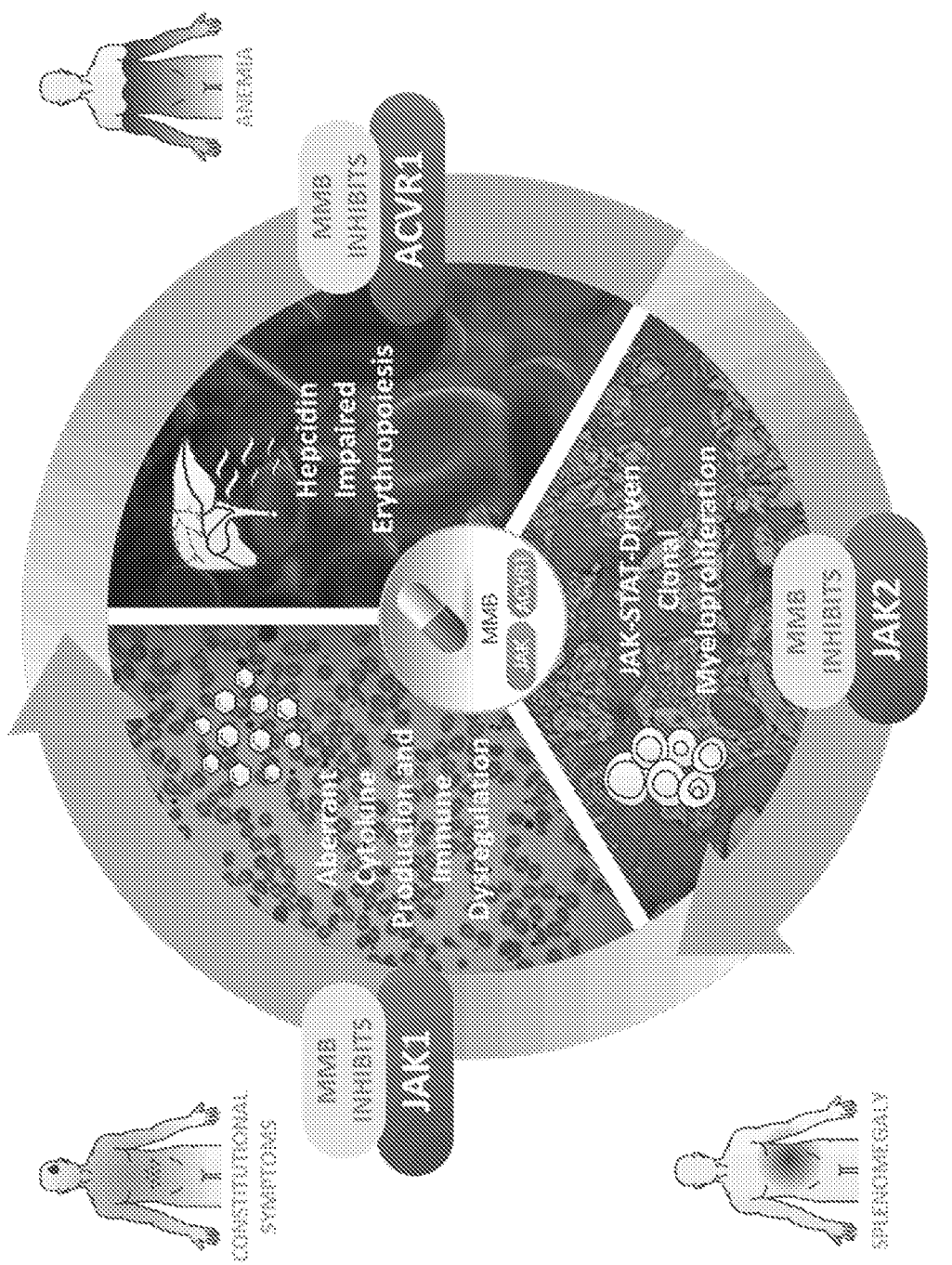
FIG. 6 is a schematic illustrating that momelotinib therapy improves three characteristics of myelofibrosis disease.

Momelotinib (MMB) is a potent, selective, orally-bioavailable, small-molecule inhibitor of JAK1, JAK2 and ACVR1 that was developed for the treatment of myelofibrosis (MF).

In two Phase three clinical trials (SIMPLIFY-1 and -2), however, MMB failed to meet the pre-defined secondary endpoints of TSS response in SIMPLIFY-1 and the primary endpoint of SRR in SIMPLIFY-2.

In the SIMPLIFY-1 trial (NCT01969838; GS-US-352-0101), the efficacy and safety of MMB versus ruxolitinib (RUX) was studied in patients with myelofibrosis who were naïve to treatment with a JAK inhibitor. Patients (N=432) with high risk or intermediate-2 risk or symptomatic intermediate-1 risk myelofibrosis received 24 weeks of treatment with 200 mg MMB once daily or 20 mg RUX twice a day (or per label), after which all patients could receive open-label momelotinib. Efficacy was measured, with a goal of demonstrating non-inferiority of MMB to RUX, by spleen response, total symptom score (TSS), rate of red blood cell transfusion, and transfusion-independence or transfusion dependence. The primary endpoint was a reduction by at least 35% in the spleen volume at 24 weeks compared with baseline.

An initial analysis of the results of the SIMPLIFY 1 trial was reported by Mesa et al. (SIMPLIFY-1: A Phase III Randomized Trial of Momelotinib Versus Ruxolitinib in Janus Kinase Inhibitor-Naive Patients with Myelofibrosis", J. Clinical Oncology 2017, 35(34):3844-3850). That analysis of the SIMPLIFY-1 trial data indicated momelotinib was noninferior to RUX for the reduction of spleen size in JAKi-näive patients, thus meeting the study's primary endpoint. However, non-inferiority was not demonstrated for the secondary endpoint of total symptom score (TSS) response, despite evidence of momelotinib's symptomatic benefits in symptomatic patients in that study. MMB treatment was associated with an increased transfusion independence rate, a decreased transfusion dependence rate and a reduced transfusion rate compared to RUX, all of which were nominally statistically-significant.

In the SIMPLIFY-2 trial (NCT02101268; GS-US-352-1214), the efficacy and safety of MMB versus best available treatment (BAT) was studied in anemic or thrombocytopenic subjects with myelofibrosis who were previously treated with ruxolitinib (RUX). There was no lower limit for the required baseline platelet count. Efficacy, with a goal of demonstrating superiority of MMB over BAT, was measured by spleen response, total symptom score (TSS), rate of red blood cell transfusion, and transfusion-independence or transfusion dependence. The primary endpoint was a reduction by at least 35% in the spleen volume at 24 weeks compared with baseline.

An initial analysis of the results of the SIMPLIFY-2 trial was reported by Harrison et al. ("Momelotinib versus best available therapy in patients with myelofibrosis previously treated with ruxolitinib (SIMPLIFY 2): a randomised, open-label, phase 3 trial." Lancet Haematol; Volume 5, Issue 2, February 2018, Pages e73-e81). That analysis of the SIMPLIFY-2 trial data indicated momelotinib was not superior to BAT for the reduction of spleen size, thus the trial failed to achieve its primary endpoint.

Although the key secondary endpoints were nominally significant in the analysis by Harrison et al., theses were not considered statistically significant in the hierarchy of analysis endpoints. In general, patients in the momelotinib group had a greater total symptom score (TSS) response, fewer transfusions, higher transfusion independence, and lower transfusion dependence compared to patients in the BAT group. The initial analysis was complicated by the failure to mandate discontinuation of ruxolitinib prior to the start of randomized study treatment. By not including a mandatory washout from prior ruxolitinib, the evaluation of the splenic response was obscured in this study in subjects in either arm. In addition, patients enrolled in this study were not selected based on splenic progression on RUX.

We have re-analyzed the data from the SIMPLIFY-1 and SIMPLIFY-2 trials and discovered that momelotinib is effective in reducing spleen size (SSR), improving total symptom scores (TSS), and improving transfusion independence rates in patients whose platelet counts are $150 \times 10^9$ per liter or below, without momelotinib administration causing thrombocytopenia, and without therefore requiring dose reduction or interruption for thrombocytopenia. Our reanalyses indicate MMB is effective in JAKi-näive patients and in patients as a second line therapy to RUX, providing benefits such as reducing enlarged spleens and improving myelofibrosis-related symptoms and/or improving transfusion independence rates in a patient population with or at risk for thrombocytopenia from the underlying disease and from current standard of care Accordingly, this disclosure describes methods of treating myeloproliferative neoplasms (MPN) such as myelofibrosis. In some embodiments, the method includes administering a therapeutically effective amount of momelotinib or a pharmaceutically acceptable salt thereof to a subject identified as having (i) myelofibrosis and (ii) a platelet count of less than $150 \times 10^9$/L.

Accordingly, this disclosure describes methods of treating myeloproliferative neoplasms (MPN) such as myelofibrosis that include administering to a subject a therapeutically effective stable dose of momelotinib or a pharmaceutically acceptable salt thereof, for a period of a plurality of weeks, where the subject is assessed as maintaining a platelet count above a predetermined threshold platelet count during the treatment period.

Methods of Treating Myelofibrosis

In a first aspect, methods are presented for treating myeloproliferative neoplasms (MPN), such as myelofibrosis, in subjects without significant reductions of baseline (pre-treatment) platelet counts or risk of developing thrombocytopenia during treatment (on-treatment). In particular, methods of treating a MPN in subjects who are identified as having particular low platelet counts, or being at risk of developing thrombocytopenia, are provided. In some embodiments, subjects having a platelet count of less than $150 \times 10^9$/L (e.g., as described herein) are targeted for treatment according to the subject methods. In some embodiments, the methods provide for administration of therapeutically effective stable doses of momelotinib over an extended period of time while avoiding the efficacy-limiting dose reductions that are often necessary for ruxolitinib patients when on-treatment platelet counts drop below certain thresholds.

Figure 34:
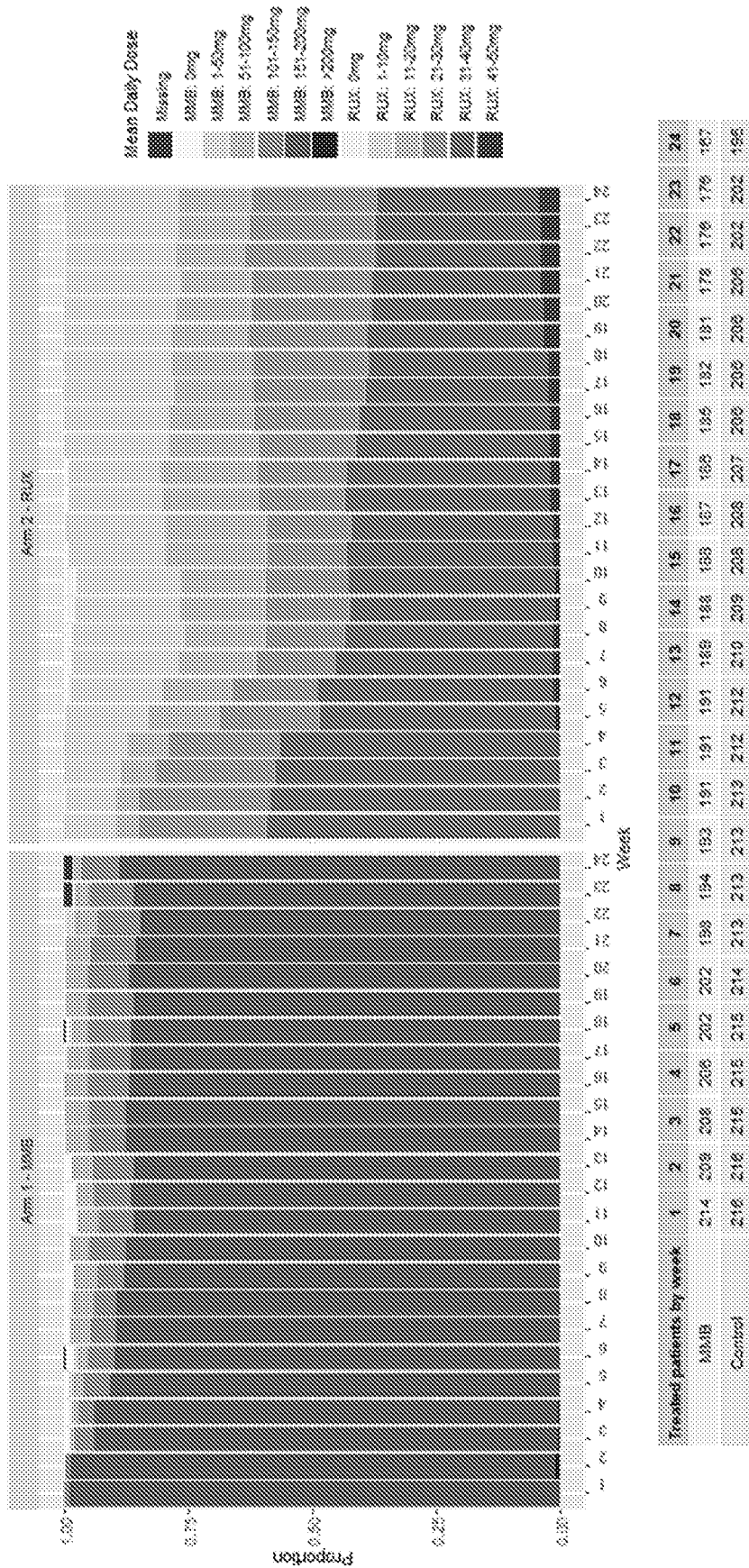
FIG. 34 shows dose categories by treatment for treated patients during the first 24 weeks of the SIMPLIFY 1 trial showing the drop in RUX doses and relative stability of MMB dose levels during treatment.
Figure 37:
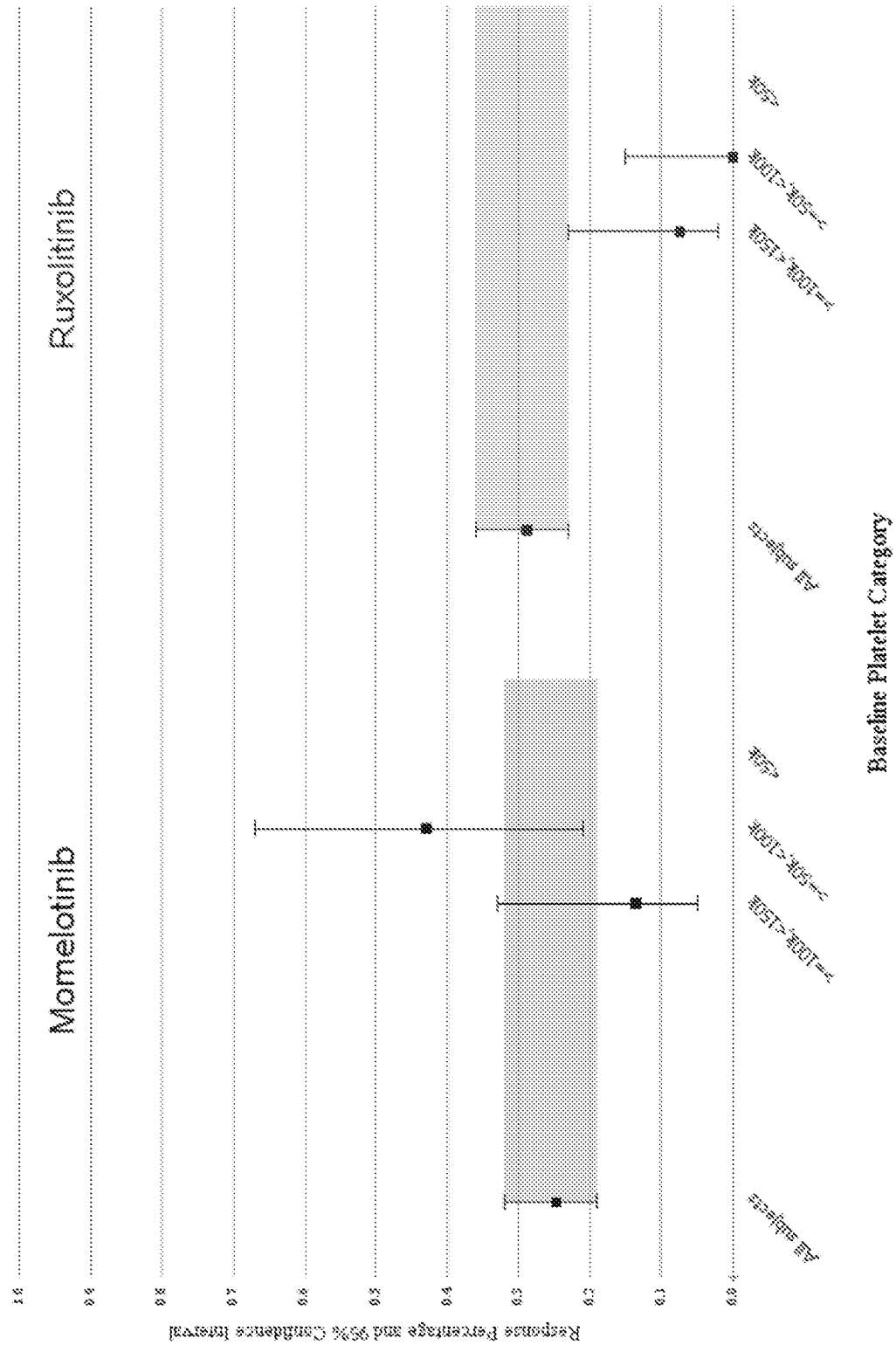
FIG. 37 shows a graph of SRR at week 24 versus baseline platelet count subgroup for symptomatic (e.g., baseline TSS of 6 or more) MMB or control (i.e., RUX) patients treated in the SIMPLIFY 1 study.
Figure 40:
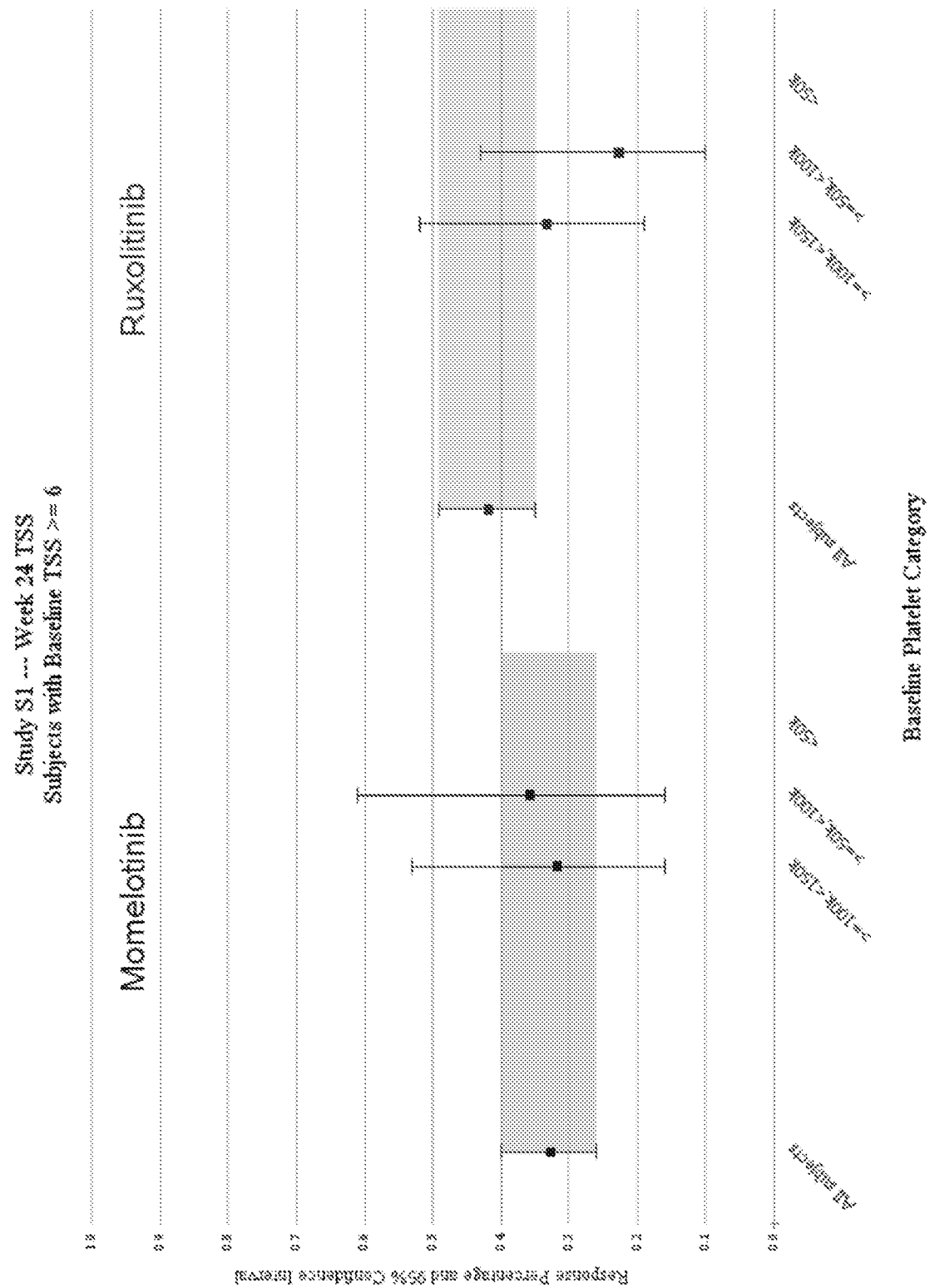
FIG. 40 shows a graph of TSS at week 24 versus baseline platelet count subgroup for symptomatic (e.g., baseline TSS of 6 or more) MMB or control (i.e., RUX) patients treated in the SIMPLIFY 1 study.
Figure 43:
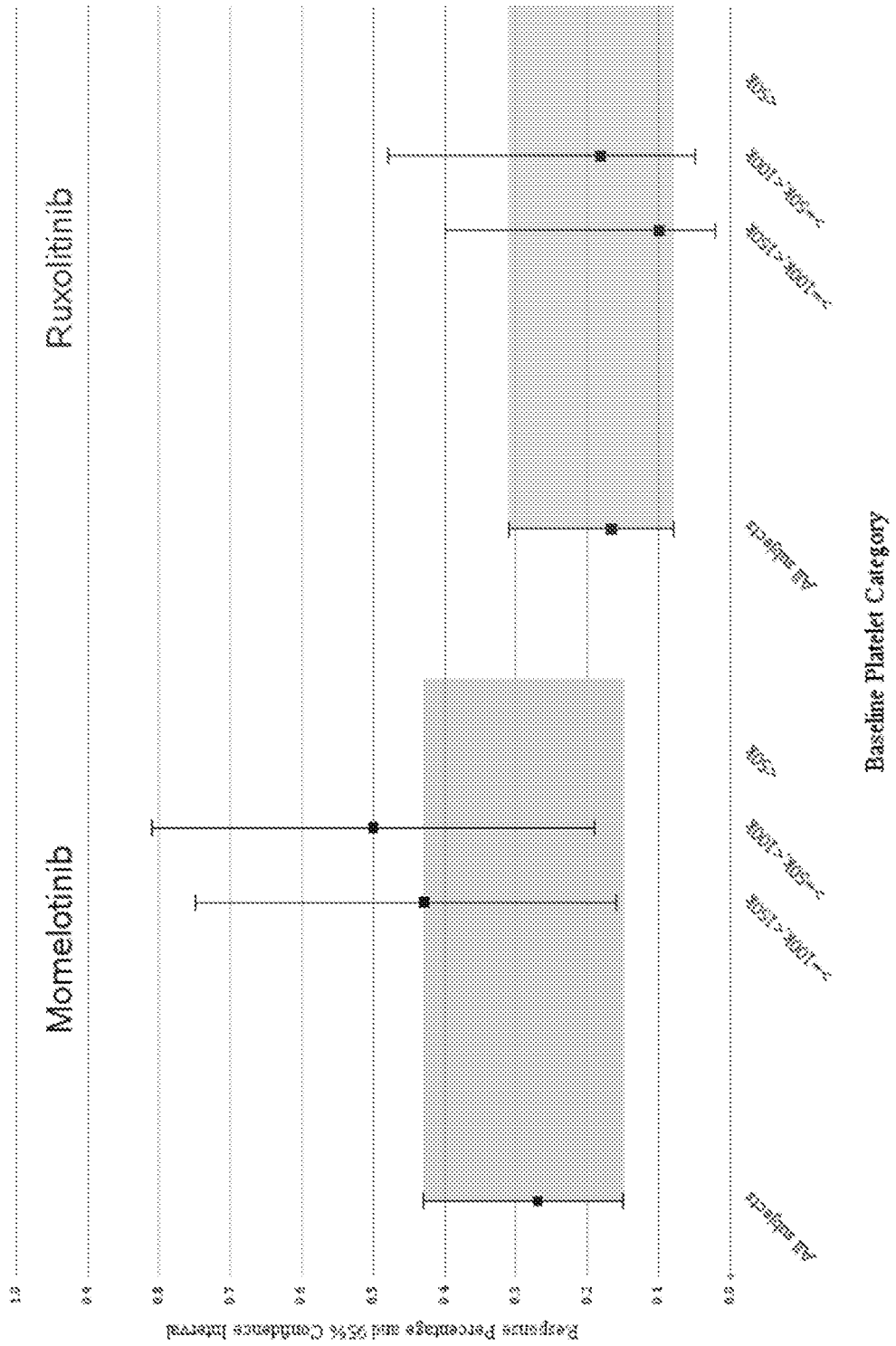
FIG. 43 shows a graph of rate of TD to TI conversion at week 24 versus baseline platelet count subgroup for symptomatic (e.g., baseline TSS of 6 or more) MMB or control (i.e., RUX) patients treated in the SIMPLIFY 1 study.

As demonstrated in the analysis of the experimental section and figures, momelotinib therapy can provide a desirable therapeutic benefit to myelofibrosis patients having particular low platelet counts in comparison to conventional ruxolitinib therapy. FIG. 34 illustrates that the splenic response rate (SRR) of MMB patients of the SIMPLIFY 1 study was better than RUX patients when the JAKi-näive myelofibrosis patients had baseline platelet count of less than $150 \times 10^9$/L, such as less than $100 \times 10^9$/L. That advantage of MMB over conventional RUX therapy was shown to be more pronounced when the subject was also symptomatic at initiation of therapy, e.g., the subject had a Total Symptom Score (TSS) of 6 or more (FIGS. 37, 40, 43).

In some embodiments, the method includes administering a therapeutically effective amount of momelotinib or a pharmaceutically acceptable salt thereof to a subject identified as having (i) a myeloproliferative neoplasm (MPN) and (ii) a platelet count of less than $150 \times 10^9$/L. In certain embodiments of the method, the subject is identified as having a platelet count of less than $100 \times 10^9$/L. In some embodiments, the subject is also identified as having a platelet count of at least $25 \times 10^9$/L, such as at least $30 \times 10^9$/L, at least $40 \times 10^9$/L or at least $50 \times 10^9$/L. In some embodiments, subject is identified as having a platelet count of $\geq 25 \times 10^9$/L and $<50 \times 10^9$/L. In some embodiments, subject is identified as having a platelet count of $\geq 50 \times 10^9$/L and $<100 \times 10^9$/L. In some embodiments, subject is identified as having a platelet count of $\geq 100 \times 10^9$/L and $<150 \times 10^9$/L. In general, platelet counts of $150 \times 10^9$/L to about $450 \times 10^9$/L are considered to be normal levels. Thrombocytopenia is generally characterized by platelet counts of less than $150 \times 10^9$/L, and further characterized by Grades 1-4 depending on the particular platelet counts of the subject. In some cases, Grade 3 or 4 thrombocytopenia (platelet counts of less than $50 \times 10^9$/L) are considered severe and require emergency attention.

The platelet count of a subject can be determined prior to initiation of momelotinib therapy. Thus, aspects of the methods include determining the level of platelets in a sample of the patient (e.g., platelet count). The platelet count can be a baseline platelet count. In some embodiments, the baseline platelet count is determined within one week prior to initiation of momelotinib therapy, where the patient: i) had not been treated with previous JAK inhibitor therapy for at least two weeks prior to initiation of momelotinib therapy; or ii) was näive to previous JAKi therapy. In some embodiments, the baseline platelet count is determined via a sample taken within two or three weeks prior to initiation of momelotinib therapy, where the patient had not been treated with previous JAK inhibitor therapy for at least two weeks prior to the platelet sample being taken. In certain embodiments, the platelet count of the patient is monitored during treatment, e.g., to determine whether or not any significant change occurs from a baseline value (e.g., a decrease of 25% or less, such as 20% or less, 15% or less 10% or less or 5% or in platelet counts from baseline). Any convenient methods can be utilized to determine the platelet count of a patient, e.g., via sampling. Methods for counting platelets that can be adapted for use in the methods disclosed herein include, but are not limited to, an electronic particle counting method (e.g., Coulter S-plus), an optical counting method (e.g., Ortho ELT 8) and a counting method using a hemocytometer.

Figure 31:
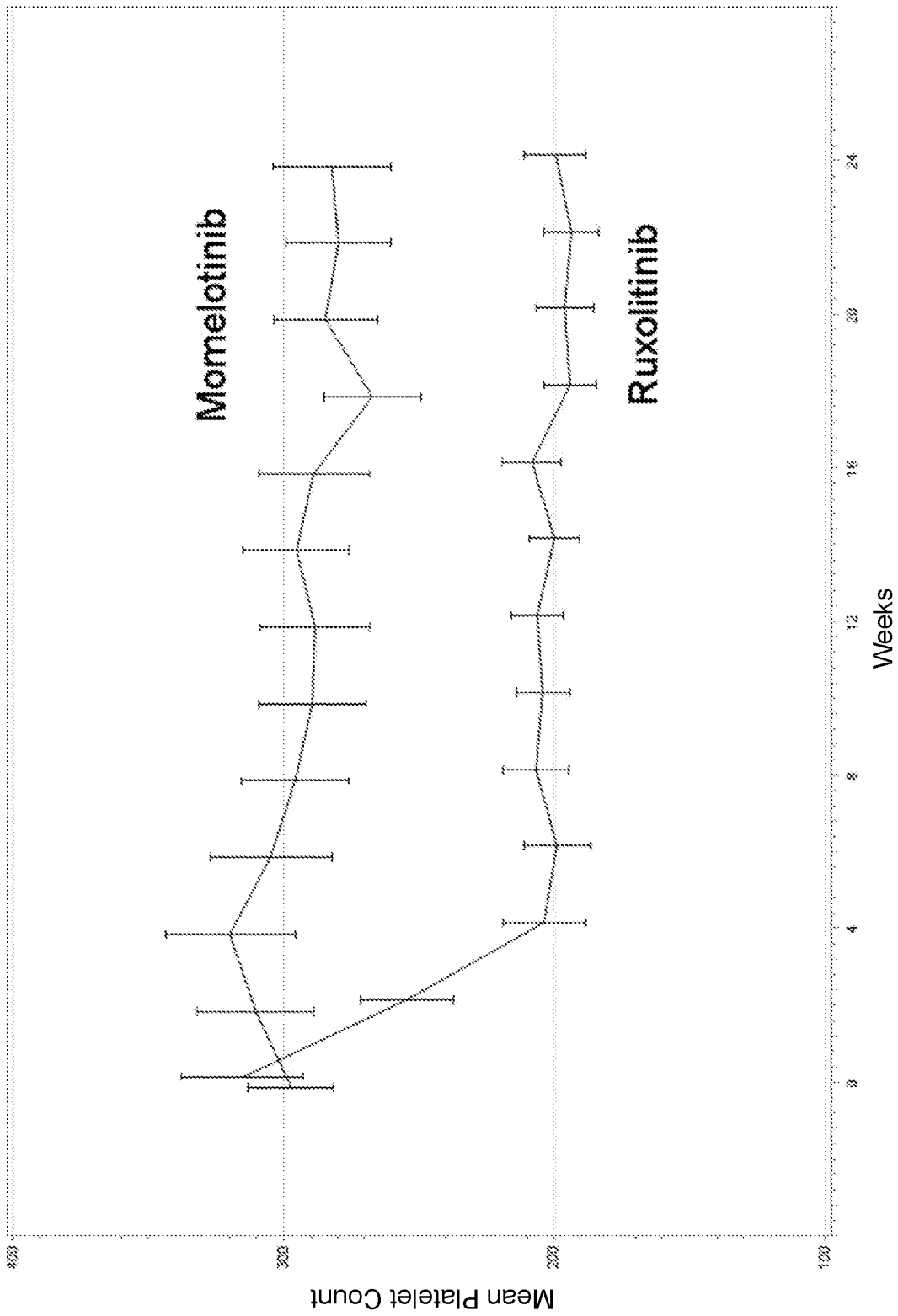
FIG. 31 shows a plot of mean (±standard error) platelet counts for MMB versus RUX subjects in the SIMPLIFY 1 study over the 24 week double blind treatment phase.
Figure 32:
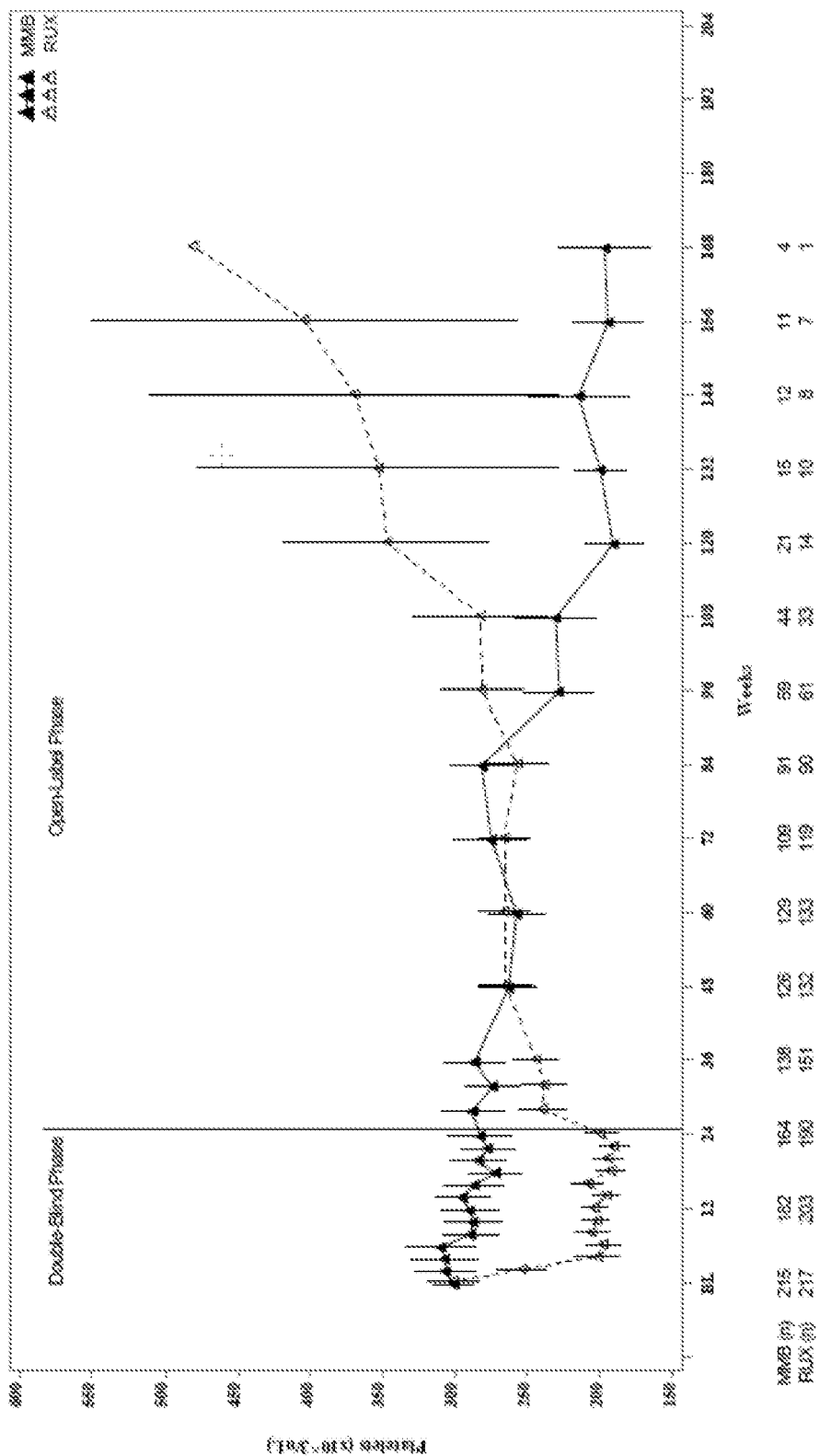
FIG. 32 shows a plot of mean (±standard error) platelet count over time for double blind and open label treatment phases for MMB versus RUX of the SIMPLIFY 1 study (Intention-to-Treat (ITT) analysis).
Figure 33:
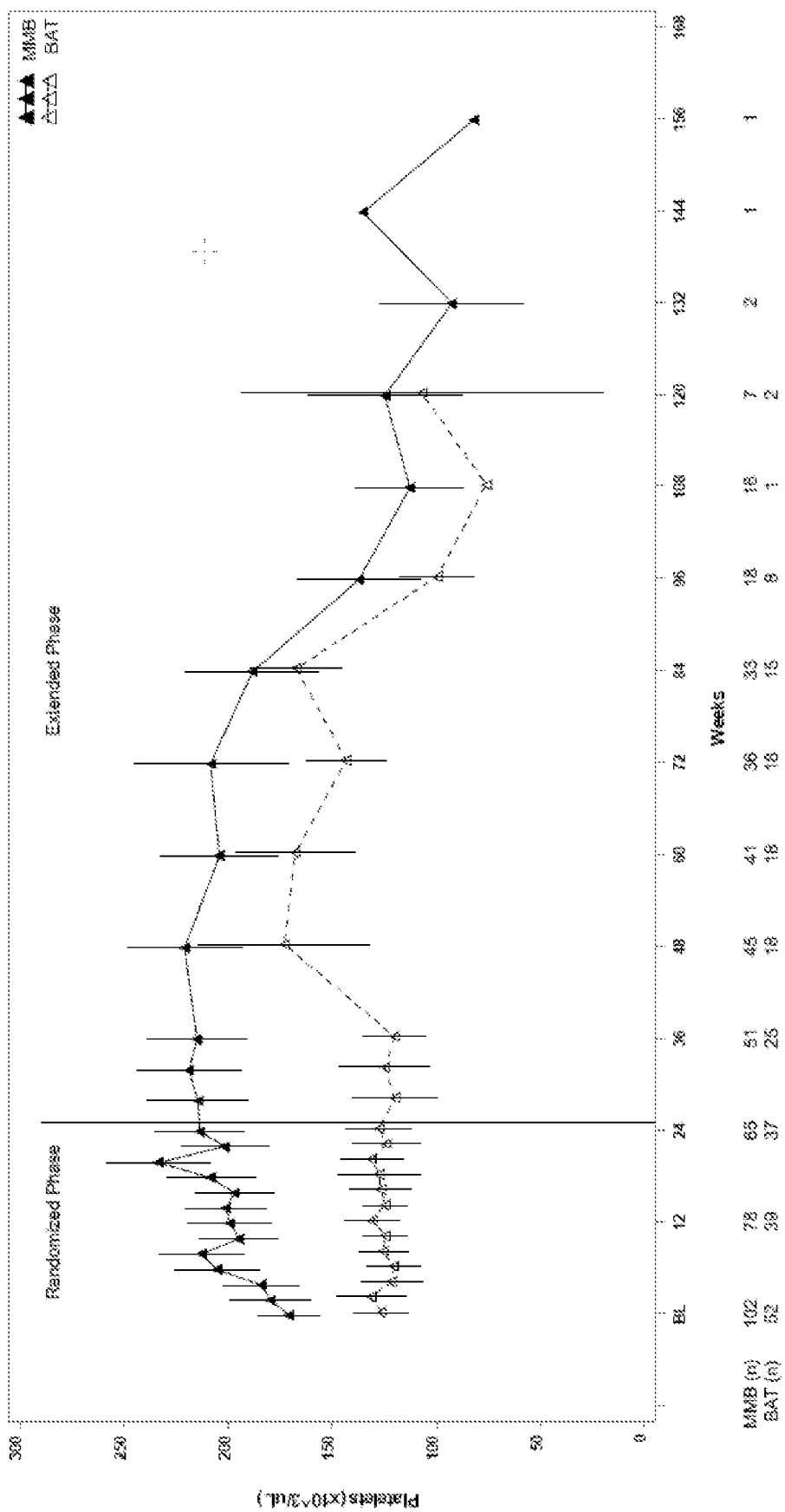
FIG. 33 shows a plot of mean (±standard error) platelet count over time for randomized and extended treatment phases for MMB versus best available therapy (BAT) of the SIMPLIFY 2 study (ITT).

FIGS. 31-33 show plots of mean platelet counts for MMB versus RUX subjects in the SIMPLIFY 1 study. This data indicates that subjects treated with MMB were able to maintain platelet levels during treatment period, e.g., during the 24 week double blind phase of the study. In comparison, RUX subjects showed significant reductions in platelet counts from baseline, which in many cases can lead to necessary dose reduction (e.g., as described herein). The MMB subjects were thus at lower risk of developing thrombocytopenia (e.g., Grade 3 or 4 thrombocytopenia), or of having to undergo undesirable dose reduction because they were able to largely maintain their platelet counts during therapy. By comparison, dose reduction (e.g., as described herein) can be necessary during conventional RUX treatment to avoid or address the development of adverse events such as thrombocytopenia.

Aspects of this disclosure thus include methods of treating a subject for a MPN (e.g., as described herein) using MMB without causing thrombocytopenia, increased risk of thrombocytopenia, or worsening the degree of thrombocytopenia (e.g., as caused by a drop in platelet counts during treatment), and without therefore requiring dose reduction or interruption for thrombocytopenia during the period of treatment. In some embodiments, the methods include administering a therapeutically effective stable dose of momelotinib or a pharmaceutically acceptable salt thereof for a treatment period of a plurality of weeks, i.e., administering MMB or a pharmaceutically acceptable salt thereof without dose reduction. The subjects treated according to these methods can maintain a platelet count above a predetermined threshold platelet count during the treatment period. In certain embodiments, the MPN is MF.

A "stable dose" is an amount of a drug administered during a set unit of time (e.g., one day up to one week) according to a dosage regimen (e.g., as described herein) that continues for multiple regular dosing intervals without dose reduction (i.e., with consistent doses), thereby maintaining therapeutically effective levels of the drug in the subject during the treatment period. In certain embodiments, the stable dose is a consistent daily dose (e.g., once daily) that is maintained during the treatment period. In some embodiments, the particular dosage regimen may be adjusted, but the amount of drug administered remains consistent. In some embodiments, a stable dose is administered once or twice daily according to a particular regimen. Any convenient therapeutically effective dose (e.g., as described herein) of momelotinib can be selected as the stable dose for use in the subject methods. The stable dose can be administered according to any convenient regimen (e.g., as described herein). In certain embodiments, the therapeutically effective stable dose of momelotinib or a pharmaceutically acceptable salt thereof is 200 mg/day. In certain embodiments, the stable dose is administered once daily. In certain embodiments, the stable dose is BID. In certain embodiments, the stable dose is administered orally.

As summarized above, subjects treated according to these methods can maintain a platelet count above a predetermined threshold platelet count during the treatment period. Accordingly, embodiments of the methods disclosed herein include administering the MMB to a subject assessed as maintaining a platelet count above a predetermined threshold platelet count during the treatment period. The predetermined threshold platelet count can be a platelet count level that is determined based on a subject's platelet count prior to initiation of treatment. In some embodiments, the subject's platelet count prior to initiation of treatment is referred to as a baseline platelet count (e.g., as described herein). In some embodiments, the predetermined threshold platelet count is a platelet level that is at a level that is at most 25% below the baseline platelet count of the subject, such as within 20%, within 15%, within 10% or within 5% below the baseline platelet count of the subject. In some embodiments, the predetermined threshold platelet count is selected to be at a level of 75% or more of the baseline platelet count, such as 80% or more, 85% or more, 90% or more, or 95% or more of the baseline platelet count.

Typically, the baseline platelet count is determined within one week prior to initiation of MMB therapy, where the patient had not been treated with previous JAK inhibitor therapy for at least two weeks prior to initiation of MMB therapy. Previous JAK inhibitor therapy such as RUX therapy can affect the platelet counts of the subject being treated and thus skew a subject's expected platelet count in absence of therapy.

The treatment period during which the therapeutically effective stable dose is administered can be an extended period of time. In some embodiments, the plurality of weeks without dose reduction is 8 weeks or more, such as 10 weeks or more. In some embodiments, the plurality of weeks without dose reduction is 12 weeks or more. In some embodiments, the plurality of weeks without dose reduction is 24 weeks or more (e.g., more than 24 weeks), such as 28 weeks or more, 32 weeks or more, 36 weeks or more, 40 weeks or more, 44 weeks or more, 48 weeks or more, 52 weeks or more, or even more. In some embodiments, the treatment period without dose reduction is 1 year or more, such as 2 years or more, 3 years or more, 4 years or more, 5 years or more, 6 years or more, 7 years or more, or 8 years or more.

In some embodiments, the subject the subject maintains a platelet count above a threshold platelet count of $50 \times 10^9$/L or more during the treatment period, such as $100 \times 10^9$/L or more, $150 \times 10^9$/L or more, $200 \times 10^9$/L or more, $250 \times 10^9$/L or more, $300 \times 10^9$/L or more, or even more. In some embodiments, the subject maintains a platelet count during the treatment period above a threshold platelet count that is less than $150 \times 10^9$/L, without the need for dose reduction due to risk of thrombocytopenia. In some embodiments, subject maintains a platelet count during the treatment period above a threshold platelet count that is $\geq 50 \times 10^9$/L and $<150 \times 10^9$/L. In some embodiments, the threshold platelet count is $\geq 25 \times 10^9$/L and $<50 \times 10^9$/L. In some embodiments, the threshold platelet count is $\geq 50 \times 10^9$/L and $<100 \times 10^9$/L. In some embodiments, the threshold platelet count is $\geq 100 \times 10^9$/L and $<150 \times 10^9$/L.

In some embodiments, the subject is one who has been identified or diagnosed as having, or being at risk for, a Myeloproliferative Neoplasm (MPN). "Myeloproliferative diseases" and "myeloproliferative neoplasms (MPN)" most notably polycythemia vera (PV), essential thrombocythemia (ET) and myelofibrosis (MF) are a diverse but inter-related group of clonal disorders of pluripotent hematopoietic stem cells that share a range of biological, pathological and clinical features including the relative overproduction of one or more cells of myeloid origin, growth factor independent colony formation in vitro, marrow hypercellularity, extramedullary hematopoiesis, spleno- and hepatomegaly, and thrombotic and/or hemorrhagic diathesis. An international working group for myeloproliferative neoplasms research and treatment (IWG-MRT) has been established to delineate and define these conditions (see for instance Vannucchi et al., CA Cancer J. Clin., 2009, 59: 171-191).

Any convenient methods can be utilized to identify or diagnose a subject who would be a candidate for treatment according to the subject methods. Subjects, most notably human patients, who present with MPN and particularly MF (e.g., PMF) are identifiable using methods such as the IWG-MRT criteria mentioned above. Some MPNs are associated with dysregulated JAK1 and JAK2 signaling. Subjects "at risk for" a particular form of MPN are subjects having an early stage form of the disease, and may for instance include subjects having a genetic marker thereof, such as the JAK2V617F allele which is associated with PV (>95%), with ET (60%) and with PMF (60%). Subjects are also considered to be "at risk for" a form of MPN if they already manifest symptoms of an earlier stage form.

In certain embodiments, the MPN that is diagnosed in the subject is myelofibrosis (MF). Myelofibrosis is meant to include primary myelofibrosis (PMF), post-polycythemia vera MF (post-PV MF), and post-essential thrombocythemia MF (post-ET MF). Diagnosis of PMF can be performed in accordance with the World Health Organization (WHO) 2016 criteria. Diagnosis of post-PV/ET MF can be confirmed in accordance with the International Working Group-Myeloproliferative Neoplasms Research and Treatment (IWG-MRT) criteria.

In some cases, the subject is classified as having intermediate or high-risk MF. Subjects with myelofibrosis can be classified as having low, intermediate-1, intermediate-2, or high risk of shortened survival, with median survival times of approximately 11, 8, 4, and 2 years, respectively. The subject can be classified according to the criteria summarized in Table 1. See e.g., Cervantes et al. ("New prognostic scoring system for primary myelofibrosis based on a study of the International Working Group for Myelofibrosis Research and Treatment." Blood. 2009; 113:2895-2901). Risk stratification of patients with MF can also be achieved according to the International Prognostic Scoring System (IPSS) (see Cervantes et al.), the dynamic IPSS (DIPSS) (see Passamonti et al. "A dynamic prognostic model to predict survival in primary myelofibrosis: a study by the IWG-MRT (International Working Group for Myeloproliferative Neoplasms Research and Treatment)" Blood 2010; 115: 1703-1708), DIPSS plus (Gangat et al. "DIPSS plus: a refined Dynamic International Prognostic Scoring System for primary myelofibrosis that incorporates prognostic information from karyotype, platelet count, and transfusion status", J. Clin. Oncol., 2011; 29:392-397), and mutation-enhanced IPSS (MIPSS) (Vannucchi et al., "Mutation-enhanced International Prognostic Scoring System (MIPSS) for primary myelofibrosis: an AGIMM & IWG-MRT project [abstract]", Blood. 2014; 124:405).

Table 1: Risk stratification of patients with MF. See Table 1 of Harrison et al. Leukemia & Lymphoma, 2016 Vol. 57, No. 10, 2259-2267.

| Risk category | Scale | Estimated survival (years) |
|---|---|---|
| IPSS | No. of risk factors[a] | Median (95% CI) |
| Low | 0 | 11.3 (9.8~15.1) |
| Intermediate-1 | 1 | 7.9 (6.6~9.5) |
| Intermediate-2 | 2 | 4.0 (3.6~4.9) |
| High | ≥3 | 2.3 (1.9~2.6) |
| DIPSS | Prognostic score[b] | Median |
| LOW | 0 | NR |
| Intermediate-1 | 1 or 2 | 14.2 |
| Intermediate-2 | 3 or 4 | 4 |
| High | 5 or 6 | 1.5 |
| DIPSS plus | Prognostic score[c] | Median |
| Low | 0 | 15.4 |
| Intermediate-1 | 1 | 6.5 |
| Intermediate-2 | 2 or 3 | 2.9 |
| High | 4-6 | 13 |
| MIPSS | Prognostic score[d] | Median |
| Low | 0-0.5 | 17.6 |
| Intermediate-1 | 1-1.5 | 7.8 |
| Intermediate-2 | 2~3.5 | 4.3 |
| High | ≥4 | 1.6 |

NR: not reached. [a] Risk factors include age>65 years, constitutional symptoms (defined as weight loss>10% of baseline value in the year preceding diagnosis and/or unexplained fever or excessive sweats persisting for more than 1 month), hemoglobin 25 $10^9$/L, and peripheral blood blasts 1%. [b] Risk factors (score) include age>65 years (1), constitutional symptoms (1), hemoglobin<10 g/dL (2), white blood cell count>25 $10^9$/L (1), and peripheral blood blasts 1% (1). [c] Scoring is based on DIPSS risk categories (low risk, 0 points; intermediate 1 risk, 1 point; intermediate-2 risk, 2 points; high risk, 3 points) and additional risk factors (unfavorable karyotype, 1 point; platelet count<100 $10^9$/L, 1 point; transfusion need, 1 point). [d] Risk factors (score) include age>60 years (1.5), constitutional symptoms (0.5), hemoglobin<100 g/L (0.5), platelet count<200 $10^9$/L (1.0), triple negative mutation status (1.5), JAK2 or MPL mutation (0.5), ASXL1 (0.5), and SRSF2 (0.5).

In certain embodiments, the patient targeted for treatment according to the subject methods is identified as having myelofibrosis and being symptomatic. A symptomatic patient is one showing one or more symptoms of the disease. Symptomatic patients can be assessed using the myeloproliferative neoplasm-symptom assessment form (MPN-SAF) total symptom score (TSS) guidelines. See e.g., Gwaltney C, Paty J, Kwitkowski V E et al. Development of a harmonized patient-reported outcome questionnaire to assess myelofibrosis symptoms in clinical trials. Leukemia Research. 2017. In some embodiments, a symptomatic myelofibrosis patient is one identified as having a Total Symptom Score (TSS) score of 6 or more, such as 7 or more, 8 or more, 9 or more or 10 or more.

The subject methods can be utilized as a first line treatment for the MPN of interest. In certain cases, the MPN is myelofibrosis. The patient to be treated according to the methods of this disclosure can be naive to Janus kinase inhibitor (JAKi) therapy. Second line treatment methods are also provided. In certain embodiments, the patient to be treated according to the methods of this disclosure has previously been treated with a JAK inhibitor. In particular embodiments, the JAK inhibitor is ruxolitinib (RUX). In particular embodiments, the JAK inhibitor is fedratinib. In certain cases, the previously-treated patient had an inadequate response to, or not deriving sufficient benefit from, or was intolerant of a Janus kinase inhibitor, e.g., RUX or fedratinib. In some embodiments, a patient who failed to respond or ceased to respond to previous therapy (e.g., with RUX or fedratinib) is treated according to the methods of this disclosure. In some case, the subject did not obtain any beneficial or desired clinical results from a prior treatment, e.g., as determined via a primary or secondary endpoint.

In certain embodiments, the subject or patient is one who (i) has not received any treatment (i.e. naive) for the disease, (ii) has received a prior treatment (e.g., JAKi, such as RUX or fedratinib) and is intolerant of the prior treatment; or (iii) is not deriving sufficient benefit from, did not respond or is resistant to, or is relapsed to a prior treatment (e.g., JAKi, such as RUX). In particular embodiments, the patient is not deriving sufficient benefit from a prior treatment (e.g., JAKi, such as RUX or fedratinib) because necessary dose reductions (e.g., due to an adverse event) result in less therapeutic benefit.

"Treatment" or "treating" is an approach for obtaining beneficial or desired results including clinical results. Beneficial or desired clinical results may include one or more of the following: a) inhibiting the disease or condition (e.g., decreasing one or more symptoms or manifestations resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); c) relieving the disease, that is, causing the regression of clinical symptoms (e.g., ameliorating the disease state, alleviating or ameliorating one or more symptoms or manifestations, providing partial or total remission of the disease or condition, enhancing effect of another medication, delaying the progression of the disease, increasing the quality of life, and/or prolonging survival; and/or d) improving or stabilizing or preventing decline in one or more clinical endpoints (e.g., as described here), including but not limited to, transfusion independence, conversion from transfusion dependent to independent, total symptom score (TSS), splenic response (SRR), and improvement of anemia.

As a chronic disease, MF is characterized by a high disease burden, disease complications, reduced quality of life (QoL) and shortened survival. Patients suffering with the disease experience a broad range of symptoms that negatively impact their social functioning, physical activity, independence with daily tasks, and overall productivity. The most common symptoms affecting patients with MF include constitutional symptoms associated with systemic inflammation such as night sweats, fever, and weight loss; abdominal symptoms secondary to splenomegaly such as abdominal discomfort/pain, early satiety, dyspnea, and diarrhea; symptoms of anemia such as fatigue; and symptoms secondary to complications of MF. Fatigue (weariness, tiredness) has been identified as the most common and most severe symptom.

Aspects of the disclosure include methods of at least ameliorating one or more symptoms or manifestations of disease of a subject identified as having a MPN. In some cases, the MPN is myelofibrosis, and the one or more symptoms of myelofibrosis are as described herein. Symptoms of myelofibrosis that may be ameliorated include, but are not limited to, fatigue, night sweats, fever, cachexia, bone pain, pruritus, weight loss, abdominal distension and pain, early satiety, dyspnea, and diarrhea. Other manifestations of the disease include, but are not limited to anemia, thrombocytopenia, and hepato-splenomegaly.

The treatment of ongoing disease, where the treatment stabilizes or reduces the undesirable clinical symptoms of the patient, is of particular interest. The expected progression-free survival times can be measured in months to years, depending on prognostic factors including the number of relapses, stage of disease, and other factors. Prolonging survival includes without limitation times of at least 1 month, about at least 2 months, about at least 3 months, about at least 4 months, about at least 6 months, about at least 1 year, about at least 2 years, about at least 3 years, or more.

Overall survival can also be measured in months to years. The patient's symptoms may remain static or may decrease. The term "effective amount" refers to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc., of the subject to be treated. The effective amount can include a range of amounts.

The terms "subject" and "patient" are used interchangeably and refer to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. A variety of other mammals can be treated using the methods of the present disclosure. For instance, mammals including, but not limited to, cows, sheep, goats, horses, dogs, cats, guinea pigs, rats or other bovine, ovine, equine, canine, feline, rodent or murine species can be treated.

"Human in need thereof" refers to a human who may have or is suspected to have diseases or conditions that would benefit from certain treatment; for example, being treated with the compounds according to the present application. The terms "subject in need thereof" or "patient in need thereof" refer to a subject or a patient who may have, is diagnosed, or is suspected to have a disease, or disorder, or condition that would benefit from the treatment described herein.

The term "therapeutically effective amount" of a compound or a pharmaceutically acceptable salt, isomer, prodrug, or solvate thereof, means an amount sufficient to effect treatment when administered to a subject, e.g., to provide a therapeutic benefit such as amelioration of one or more symptoms or slowing of disease progression. The therapeutically effective amount may vary depending on the subject, and disease or condition being treated, the weight and age of the subject, the severity of the disease or condition, and the manner of administering, which can be readily determined.

The compounds of the present application or the compositions thereof may be administered once, twice, three, or four times daily, using any suitable mode described herein. Also, administration or treatment with MMB may be continued for a number of days; for example, commonly treatment would continue for at least 7 days, 14 days, or 28 days, for one cycle of treatment. Treatment cycles are generally known and are frequently alternated with resting periods of about 1 to 28 days, commonly about 7 days or about 14 days, between cycles. The treatment cycles, in other embodiments, may also be continuous.

In the treatment of an identified subject, an appropriate unit dose of the MMB compound will generally be about 0.01 to 500 mg per kg patient body weight per day which can be administered in single or multiple doses. The dosage level will be about 0.1 to about 250 mg/kg per day; such as about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. Suitable unit doses will typically be in the range from 10 to 500 mg, such as 50-400 mg, e.g., 100, 150, 200, 250 or 300 mg. For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient. The dosage may be selected, for example to any dose within any of these ranges, for therapeutic efficacy and/or symptomatic adjustment of the dosage to the patient to be treated. The compound will preferably be administered on a regimen of 1 to 4 times per day, preferably once or twice per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In some embodiments of the subject methods, the therapeutic effective amount of the MMB compound described herein is a dose of 50 mg, 100 mg, 150 mg, 200 mg, 250 mg, or 300 mg. In certain cases, the therapeutically effective amount is between 100 mg/day and 300 mg/day, such as 100 mg/day, 150 mg/day, 200 mg/day, 250 mg/day, or 300 mg/day. In certain cases, the therapeutically effective amount is between 50 mg/day and 200 mg/day, such as 50 mg/day, 100 mg/day, 150 mg/day, or 200 mg/day. In some embodiments of the subject methods, the therapeutic effective amount is 200 mg/day. The administration can be oral. In some cases, the administration is once daily. In some cases, the administration is BID, e.g., in equally divided doses. In certain cases, the MMB is administered with food. In certain cases, the MMB is administered without food.

For patients unable to ingest tablets orally, the therapeutic effective amount of the MMB compound can be administered through another route, e.g., via a nasogastric tube.

The improved outcome from MMB therapy that results from practicing the subject methods can be manifested as an improvement in one or more clinical endpoints (e.g., as described herein), such as anemia response, in spleen response and/or symptom response. By "anemia response" is meant an increase in the patient's hemoglobin level or a patient who was transfusion dependent becoming transfusion independent. Desirably, a minimum increase in hemoglobin of 0.5 g/dL, such as 1.0 g/dL 1.5 g/dL or 2.0 g/dL lasting a minimum of 8 weeks is achieved, which is the level of improvement specified in the International Working Group (IWG) consensus criteria. However, smaller, but still medically significant, increases in hemoglobin are also considered to be within the term "anemia response". "Transfusion independence" is an anemia endpoint and refers to a subject who required no RBC transfusions over a 12 week period and had no hemoglobin levels less than 8 g/dL to 8.5 g/dL over the 12 week period. In some embodiments, the 12 week period of transfusion independence is the terminal 12 weeks of a 24 week study period. By red blood cell (RBC) transfusion independence rate at week 24 of a study is meant the proportion of subjects who were transfusion independent at week 24, excluding cases associated with clinically overt bleeding.

By "spleen response" is meant a reduction in the size of the patient's spleen as assessed by either palpation of a previously palpable spleen during physical exam or by diagnostic imaging. The IWG consensus criteria specifies that there be either a minimum 50% reduction in palpable splenomegaly (spleen enlargement) of a spleen that is at least 10 cm at baseline (prior to treatment) or of a spleen that is palpable at more than 5 cm below the left costal margin at baseline becomes not palpable. However, smaller reductions are also considered to be within the term "spleen response". Splenic enlargement can be assessed by palpation. Splenic size and volume can also be measured by diagnostic imaging such as ultrasound, CT or MRI). In some cases, normal spleen size is considered to be approximately 11.0 cm. in craniocaudal length.

By "symptom response" or "symptomatic response" is meant a reduction in a patient's average daily TSS of at least 50% as compared to a baseline TSS determined at or before initiation of treatment (e.g., as described herein).

Momelotinib

In the methods described herein, momelotinib, or a pharmaceutically acceptable salt thereof, is administered in therapeutically effective amounts.

Momelotinib (MMB) is an inhibitor of JAK (JAK1 and JAK2) and ACVR1 that is also known as N-(cyanomethyl)-4-(2-(4-morpholinophenylamino)pyrimidin-4-yl)benzamide or CYT-0387 and has the structure of Formula I:

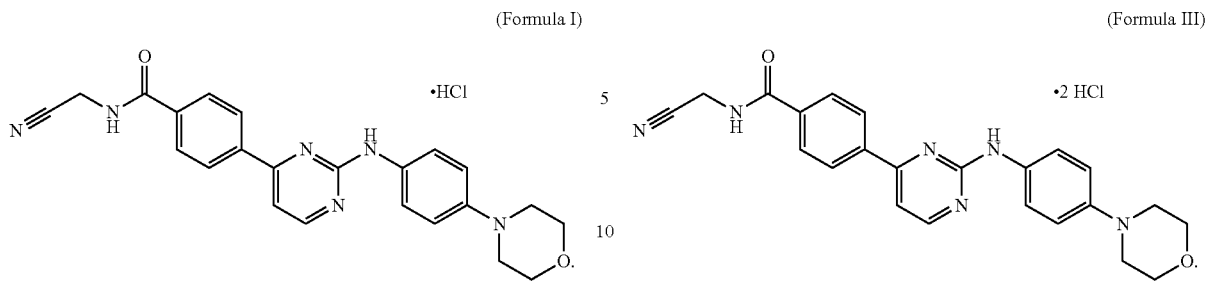

(Formula I)

(Formula III)

"Pharmaceutically acceptable salt" refers to a salt of a compound that retains the biological effectiveness and properties of the underlying compound, and which is not biologically or otherwise undesirable. MMB can be present as an acid addition salt. Pharmaceutically acceptable acid addition salts of basic drugs may be prepared using inorganic and organic acids. Acids useful for reaction with MMB to form pharmaceutically acceptable salts (acid addition salts), and methods for accomplishing same, are known to skilled artisans. If the MMB is present as an acid addition salt, MMB free base can be obtained by basifying a solution of the acid salt. A solvate is formed by the interaction of a solvent and a MMB compound. Solvates of salts of the MMB compounds described herein are also used in particular embodiments of the methods described herein. In some cases, the MMB compound solvate is a hydrate.

Embodiments of the methods disclosed herein use any convenient acid addition pharmaceutically acceptable salts of momelotinib, or a solvate or hydrate thereof. In some embodiments, the momelotinib compound is a hydrochloride salt. In certain embodiments, the compound hydrochloride salt that finds use in the subject methods is momelotinib monohydrochloride of formula II:

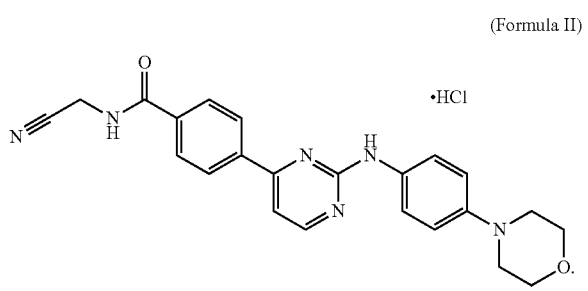 [SMILES: N#CCNC(=O)c1ccc(-c2ccnc(Nc3ccc(N4CCOCC4)cc3)n2)cc1 ; Cl]

(Formula II)

In certain embodiments, the momelotinib monohydrochloride salt is anhydrous. In certain embodiments, the momelotinib monohydrochloride salt is a hydrate, e.g., a monohydrate.

In particular embodiments, the momelotinib hydrochloride salt used is momelotinib dihydrochloride of formula III:

In certain embodiments, the momelotinib dihydrochloride salt is anhydrous. In certain embodiments, the momelotinib dihydrochloride salt is a hydrate, e.g., momelotinib dihydrochloride monohydrate.

Embodiments of the methods described herein use any crystalline salt forms of momelotinib, including but not limited to, those forms described in WO2015191846, the disclosure of which is herein incorporated by reference. In some embodiments, a crystalline salt form of momelotinib is referred to as a polymorph form of the compound.

Figure 19:
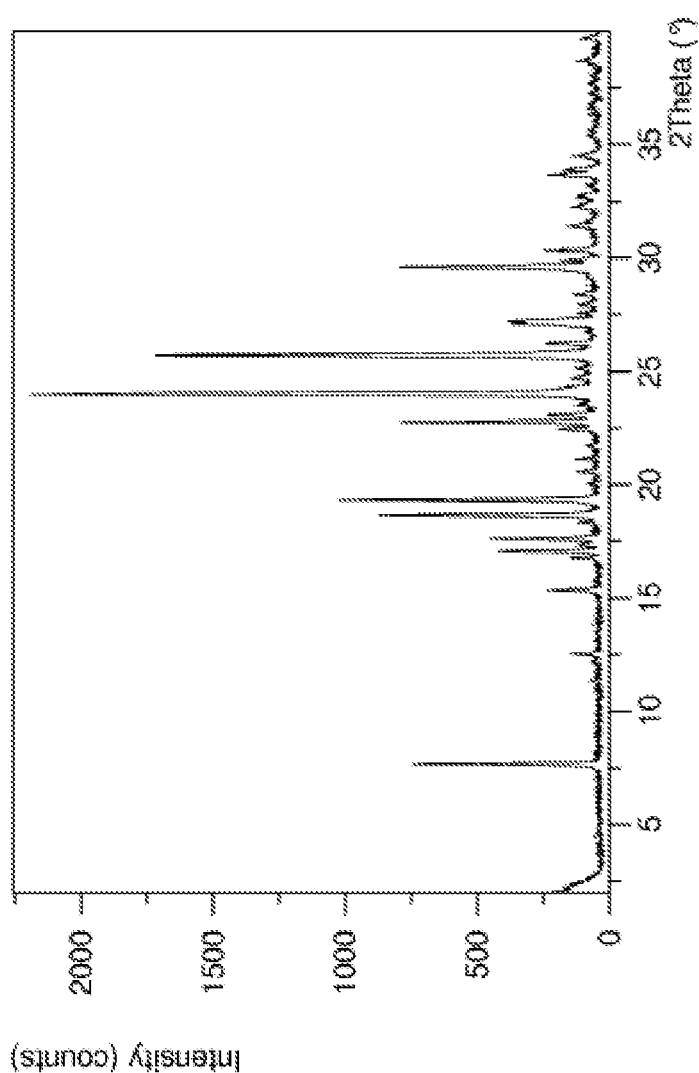
FIG. 19 shows a XRPD pattern for momelotinib dihydrochloride monohydrate Form II.
Figure 22:
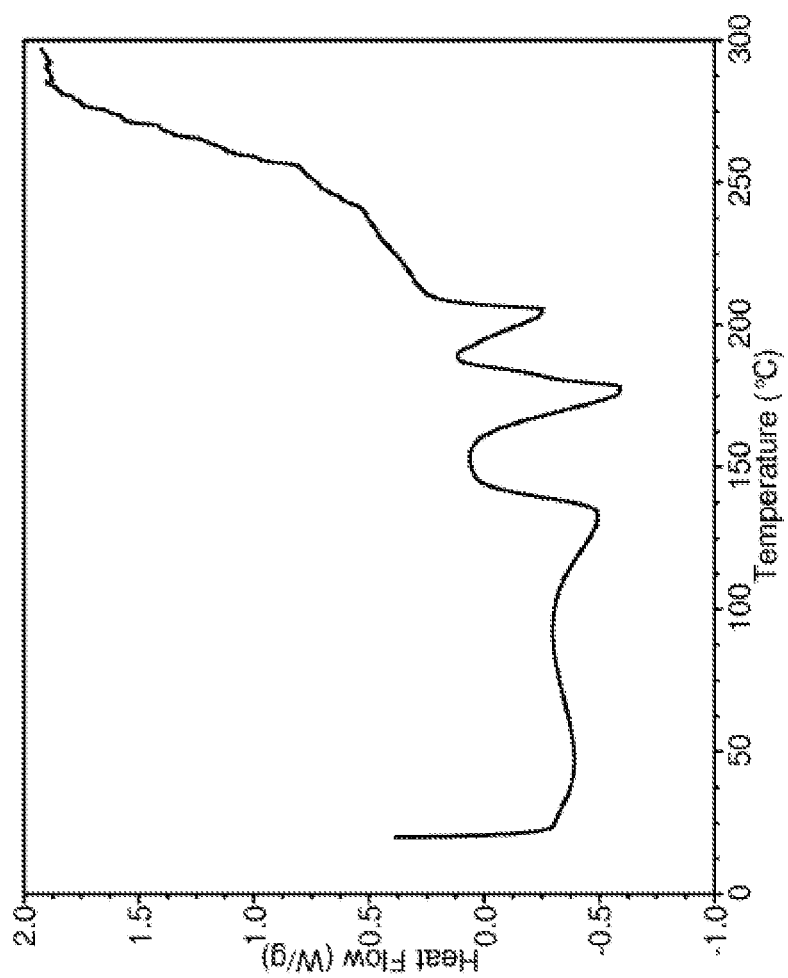
FIG. 22 shows a DSC plot for momelotinib dihydrochloride monohydrate Form II.
Figure 25:
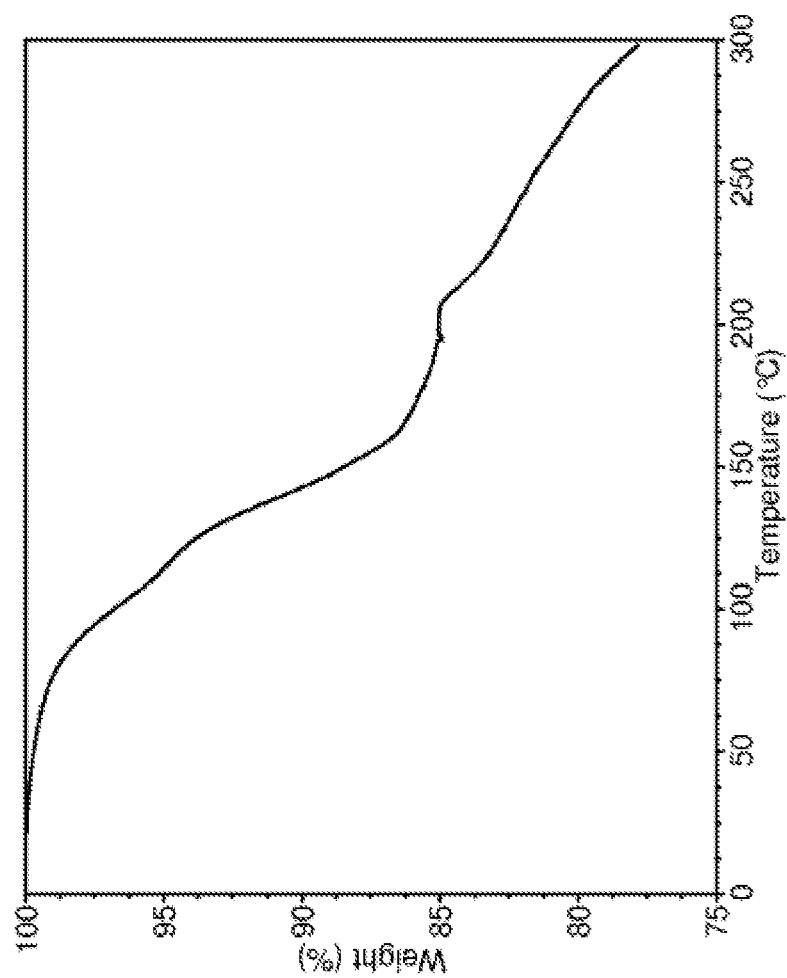
FIG. 25 shows a TGA for momelotinib dihydrochloride monohydrate Form II.
Figure 28:
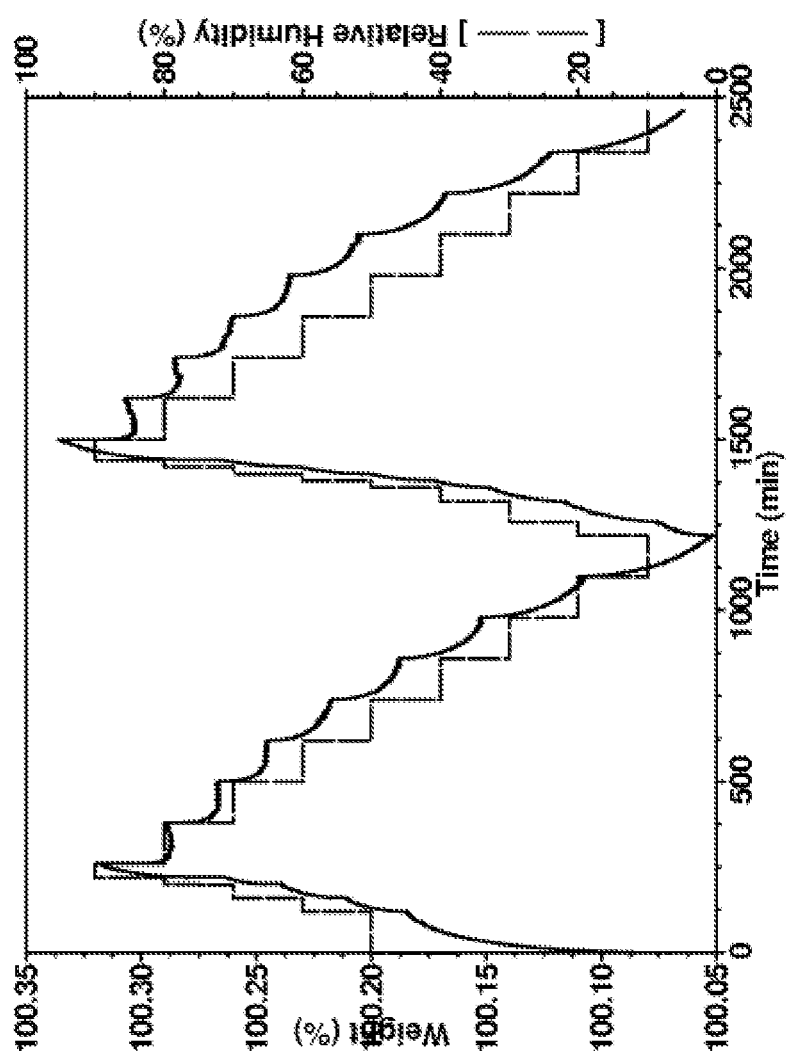
FIG. 28 shows a DVS plot for momelotinib dihydrochloride monohydrate Form II.

In some embodiments, the MMB compound used is momelotinib dihydrochloride monohydrate that is in crystalline Form II. The crystalline Form II is characterized by one or more parameters, as follows. The crystalline Form II can be characterized by crystals with unit cell parameters at T=100° K of: a=10.2837(6) A, b=10.4981(6) A, c=11.5143(7) A, α=83.297(2)®, β=87.649(2)°, γ=67.445(2)°, and a triclinic P-1 space group. The crystalline Form II can be characterized by an x-ray powder diffraction (XRPD) pattern substantially as set forth in FIG. 19. The crystalline Form II can be characterized by an x-ray powder diffraction (XRPD) pattern having peaks at 7.7°, 19.3°, 24.0°, 25.7°, and 29.6° 2-Θ+0.2° 2-Θ. The crystalline Form II can be characterized by differential scanning calorimetry (DSC) pattern substantially as set forth in FIG. 22. The crystalline Form II can be characterized by a dynamic vapor sorption (DVS) pattern substantially as set forth in FIG. 28, or by a thermogravimetric analysis (TGA) substantially as set forth in FIG. 25.

Figure 20:
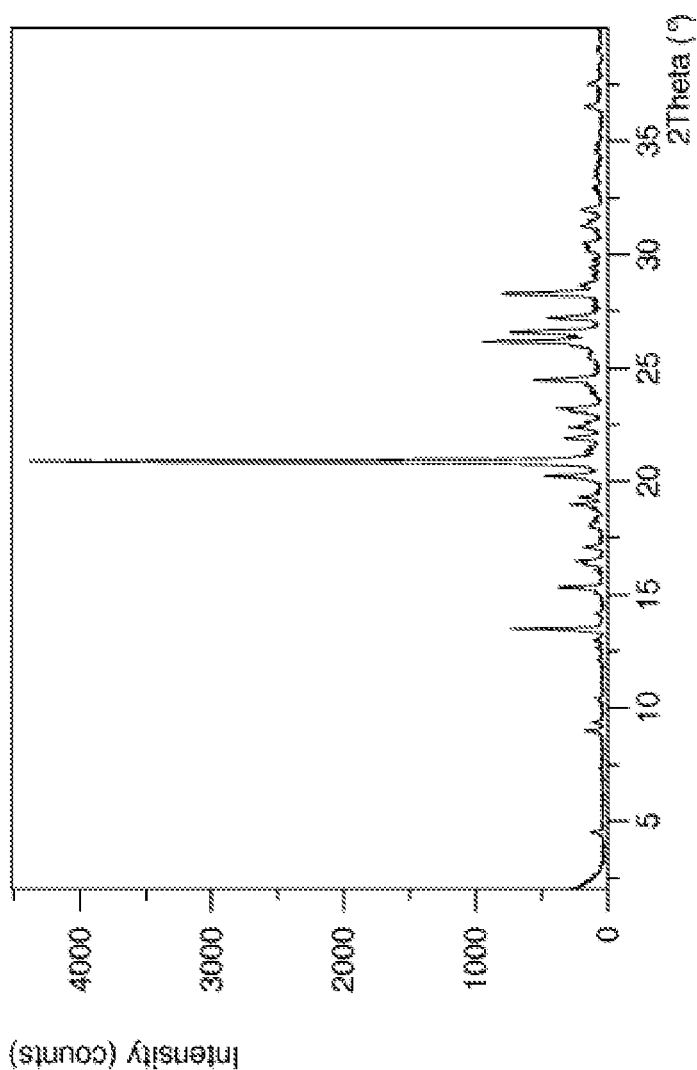
FIG. 20 shows a XRPD pattern for momelotinib monohydrochloride anhydrous Form I.
Figure 23:
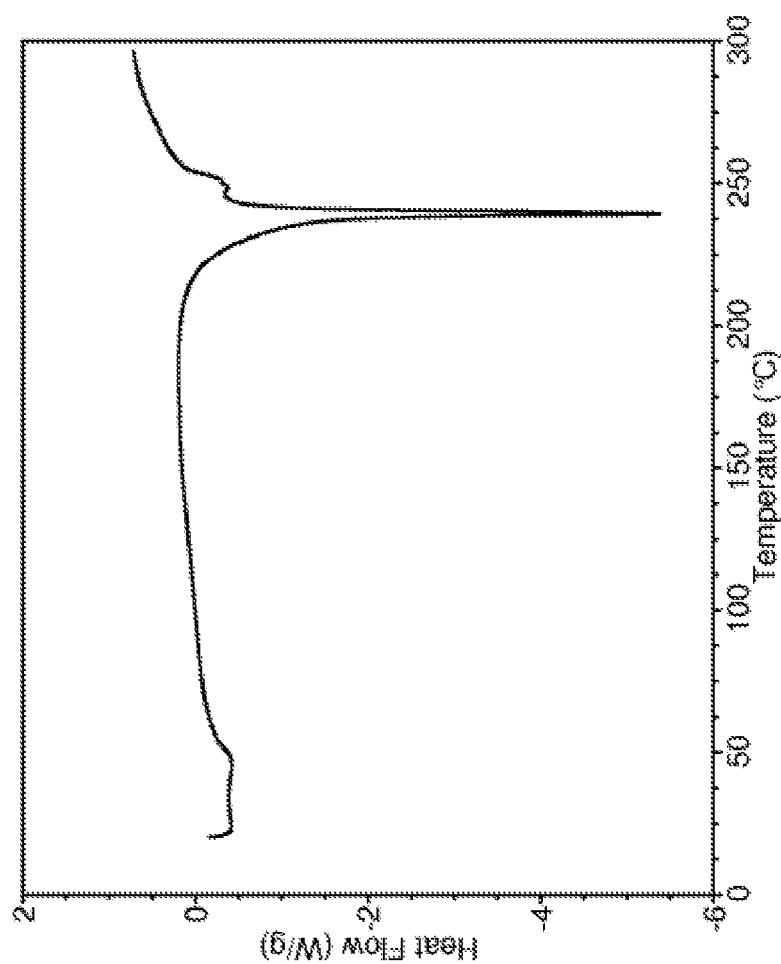
FIG. 23 shows a DSC plot for momelotinib monohydrochloride anhydrous Form I.
Figure 26:
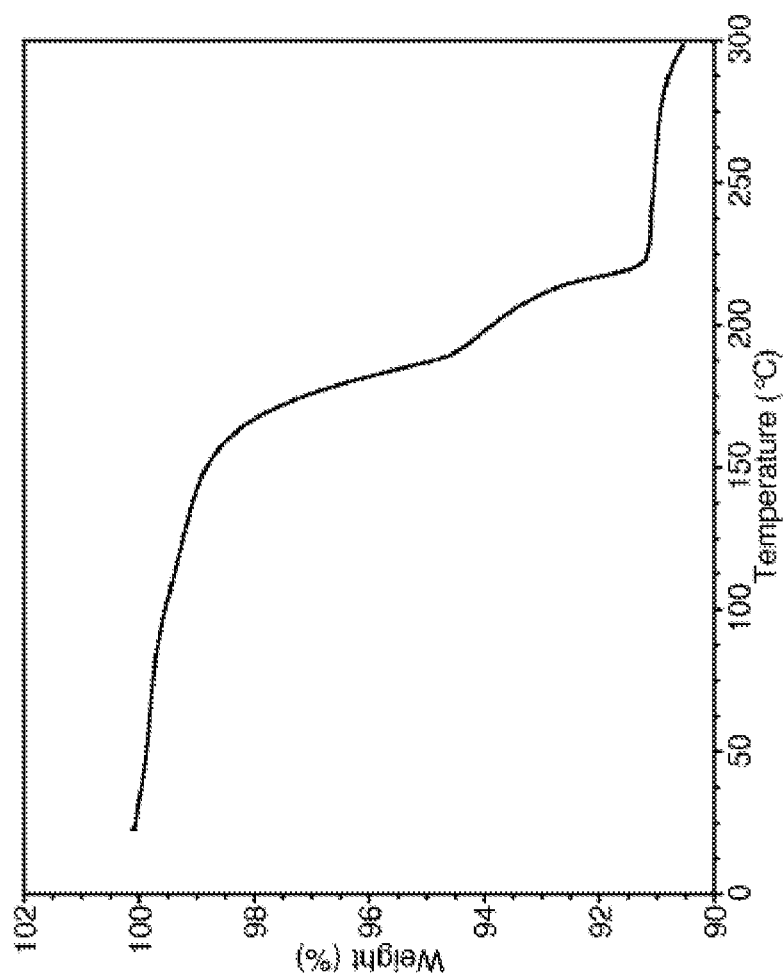
FIG. 26 shows a TGA for momelotinib monohydrochloride anhydrous Form I.

In some embodiments, the MMB compound used is momelotinib monohydrochloride anhydrous that is in crystalline Form I. The crystalline Form I is characterized by one or more parameters, as follows. The crystalline Form I can be characterized by an x-ray powder diffraction (XRPD) pattern substantially as set forth in FIG. 20. The crystalline Form I can be characterized by an X-ray powder diffraction ("XRPD") pattern having peaks at 13.5°, 20.9°, 26.1°, 26.6°, and 28.3° 2-Θ+0.2° 2-Θ. The crystalline Form I can be characterized by a differential scanning calorimetry (DSC) pattern substantially as set forth in FIG. 23. The crystalline Form I can be characterized by a TGA substantially as set forth in FIG. 26.

Figure 21:
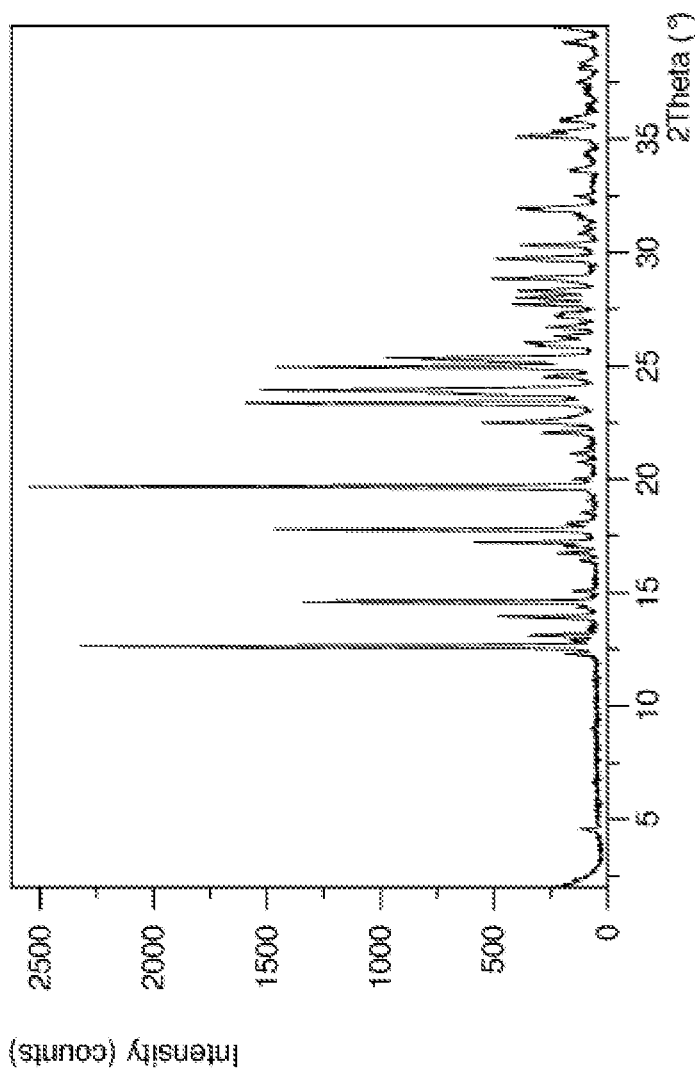
FIG. 21 shows a XRPD pattern for momelotinib monohydrochloride anhydrous Form III.
Figure 24:
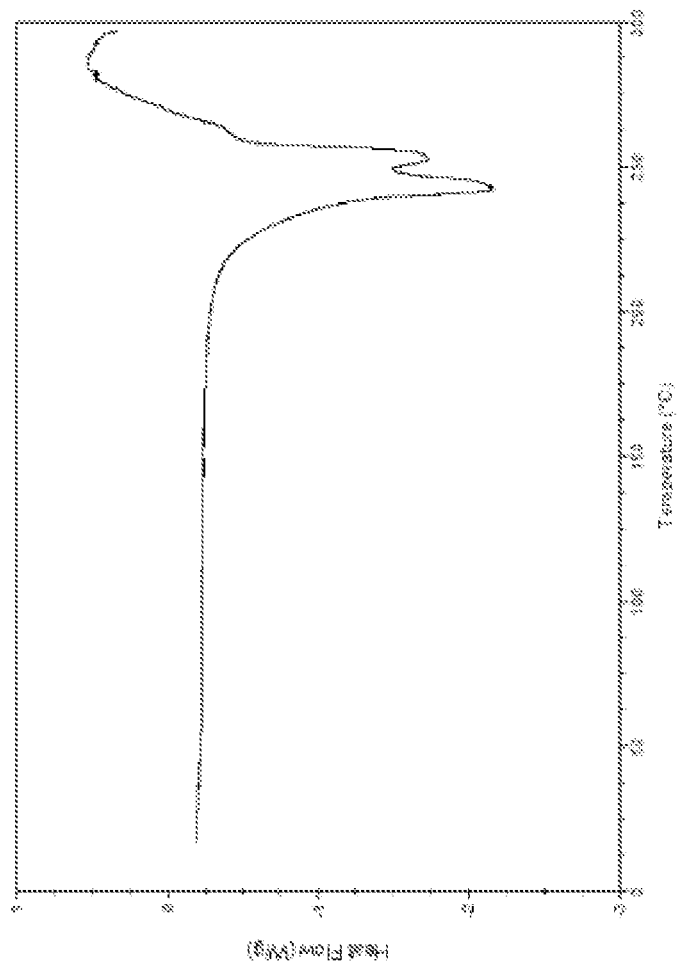
FIG. 24 shows a DSC plot for momelotinib monohydrochloride anhydrous Form III.
Figure 27:
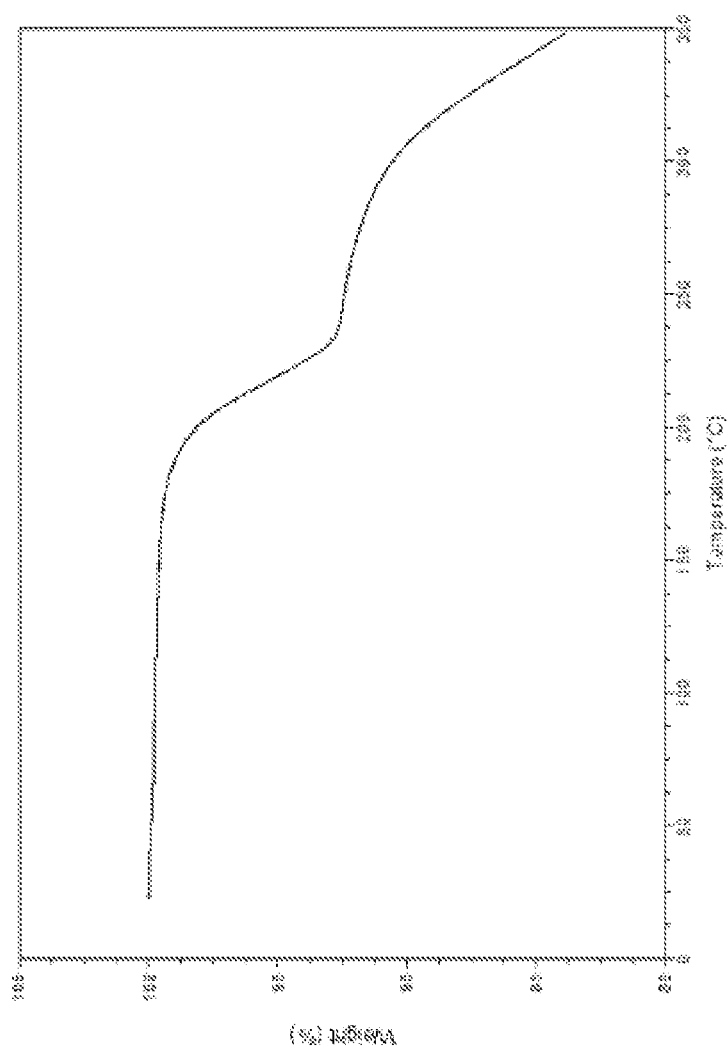
FIG. 27 shows a TGA for momelotinib monohydrochloride anhydrous Form III.

In some embodiments, the MMB compound used is momelotinib monohydrochloride anhydrous that is in crystalline Form III. The crystalline Form III is characterized by one or more parameters, as follows. The crystalline Form III can be characterized by an x-ray powder diffraction (XRPD) pattern substantially as set forth in FIG. 21. The crystalline Form III can be characterized by an X-ray powder diffraction pattern having peaks at 12.7°, 14.6°, 17.8°, 19.7°, and 23.3° 2-Θ+0.2° 2-Θ. The crystalline Form III can be characterized by a differential scanning calorimetry (DSC) pattern substantially as set forth in FIG. 24. The crystalline Form III can be characterized by a TGA substantially as set forth in FIG. 27.

In some embodiments, the MMB compound used is momelotinib dihydrochloride anhydrous Form IV (MMB Form IV). The crystalline Form IV is characterized by one or more parameters, as follows. The crystalline Form III can have an XRPD pattern having peaks at 5.5°, 10.1°, 14.9°, 25.1°, and 26.6° 2-Θ+0.2° 2-Θ.

TABLE 2

XRPD peaks for momelotinib forms

| MMB dihydrochloride anhydrous Form I | | MMB dihydrochloride monohydrate Form II | | MMB monohydrochloride anhydrous Form I | | MMB monohydrochloride anhydrous Form III | |
|---|---|---|---|---|---|---|---|
| Position [°2th.] | Relative Intensity [%] | Position [°2th.] | Relative Intensity [%] | Position [°2th.] | Relative Intensity [%] | Position [°2th.] | Relative Intensity [%] |
| 5.5 | 31.0 | 7.7 | 33.7 | 13.5 | 15.3 | 12.7 | 85.0 |
| 10.1 | 100.0 | 19.3 | 43.7 | 20.9 | 100.0 | 14.6 | 50.0 |
| 14.9 | 66.5 | 24.0 | 100.0 | 26.1 | 20.6 | 17.8 | 55.5 |
| 25.1 | 86.7 | 25.7 | 79.0 | 26.6 | 15.5 | 19.7 | 100.0 |
| 26.6 | 69.3 | 29.6 | 35.7 | 28.3 | 16.6 | 23.3 | 60.1 |

The following patent applications are incorporated by reference for all purposes, including but not limited to the use of MMB described therein: International application no. PCT/AU2008/000339, filed on Mar. 12, 2008; and International application no. PCT/AU2011/001551, filed on Nov. 29, 2011; and International application no. PCT/US2015/035316, filed on Jun. 11, 2015; and International application no. PCT/US2017/045957, filed on Aug. 8, 2017.

Pharmaceutical Compositions

The MMB compounds are usually administered in the form of pharmaceutical compositions. Embodiments of the methods disclosed herein include administering a pharmaceutical composition that contains a MMB compound disclosed herein or a pharmaceutically acceptable salt, or solvate or hydrate thereof, and one or more pharmaceutically acceptable vehicles selected from carriers, adjuvants and excipients.

The pharmaceutical compositions may be administered in either single or multiple doses. The pharmaceutical composition may be administered by various methods. In certain embodiments, the pharmaceutical composition is administered by intra-arterial injection, intravenously, intraperitoneally, parenterally, intramuscularly, subcutaneously, orally, topically, or as an inhalant.

Oral administration is a currently preferred route for administration of the MMB compounds described herein. In currently preferred embodiments, the forms or compositions of MMB thereof described herein are formulated for oral administration using pharmaceutically acceptable carriers. Pharmaceutical compositions formulated for oral administration can be in the form of tablets, capsules, cachets, dragees, lozenges, liquids, gels, syrups, slurries, elixirs, suspensions, or powders.

Administration may be via, for example, capsule or enteric coated tablets. In making the pharmaceutical compositions that include a MMB compound described herein or a pharmaceutically acceptable salt, or solvate or hydrate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, and capsules. The tablets of the MMB compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The specific dose level of a MMB compound described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a MMB compound per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Pharmaceutically Acceptable Vehicles

Pharmaceutically acceptable vehicles include carriers, adjuvants and excipients, for example, inert solid diluents and fillers, diluents, including sterile aqueous solution and various organic solvents, permeation enhancers, solubilizers and adjuvants.

The term "carrier" refers to diluents or fillers, disintegrants, precipitation inhibitors, surfactants, glidants, binders, lubricants, anti-oxidants, and other excipients and vehicles with which the MMB compound is administered. Examples of carriers that are useful in dosage forms administered in the methods described herein include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions provided in the present disclosure, and the amounts of such carriers in the composition, may vary depending on the method of formulation (e.g., dry granulation formulation, solid dispersion formulation).

The term "diluent" or "filler" generally refers to a substance that is used to dilute the MMB compound prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent. One example of a precipitation inhibitor includes hydroxypropylmethylcellulose.

The term "surfactants" generally refers to compounds that lower the surface tension between two liquids or between a liquid and a solid. Examples of surfactants include poloxamer and sodium lauryl sulfate.

The term "glidant" generally refers to a substance used in tablet and capsule formulations to improve flow-properties during tablet compression and to produce an anti-caking effect. Examples of glidants include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders include hydroxypropylcellulose, hydroxypropylmethylcellulose, povidone, copovidone, ethyl cellulose, gelatin, and polyethylene glycol.

The term "lubricant" generally refers to a substance that is added to a powder blend to prevent the compacted powder mass from sticking to the equipment during the tableting or encapsulation process. A lubricant can aid the ejection of the tablet from the dies during tableting, and can improve powder flow. Examples of lubricants include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

The term "anti-oxidant" generally refers to a substance that inhibits the oxidation of other substances. In certain embodiments of the invention, anti-oxidants are added to the pharmaceutical composition. Examples of anti-oxidants include ethylenediaminetetraacetic acid, ethylenediaminetetraacetic acid disodium salt, sodium sulfite, sodium metabisulfite, sodium bisulfite, butylated hydroxytoluene (BHT), butylated hydroxyanisole (BHA), ascorbic acid, ascorbyl palmitate, thioglycerol, thioglycolic acid, tocopherol (vitamin E), D-α tocopheryl polyethylene glycol 1000 succinate (vitamin E TPGS) and propyl gallate. In certain embodiments, the antioxidant is propyl gallate.

In some embodiments, the pharmaceutical composition includes MMB dihydrochloride monohydrate Form II and an antioxidant selected from butylated hydroxyanisole (BHA), ascorbic acid, and propyl gallate. In particular embodiments, the pharmaceutical composition comprises MMB dihydrochloride monohydrate Form II and the antioxidant propyl gallate. The antioxidant may be present in an amount sufficient to prevent, inhibit, and/or reduce degradation of the MMB active ingredient (such as MMB Form II). By way of examples, the antioxidant may be present in an amount of about 0.001, about 0.002%, about 0.005%, about 0.01%, about 0.02%, about 0.05%, about 0.1%, about 0.2%, about 0.5%, or about 1% by weight in the pharmaceutical composition. In one embodiment, the pharmaceutical composition includes propyl gallate at an amount of about 0.001%, about 0.01%, about 0.1%, about 0.2%, about 0.5%, or about 1%. In particular embodiments, the pharmaceutical composition includes MMB dihydrochloride monohydrate Form II and about 0.2% of propyl gallate.

In certain aspects, a pharmaceutical composition including a MMB compound active agent (for example, MMB dihydrochloride monohydrate Form II), and one or more of (a)-(e): a) at least one diluent; b) at least one disintegrant; c) at least one glidant; d) at least one lubricant; and e) at least one anti-oxidant.

In some embodiments, the pharmaceutical composition includes at least one or at least two diluent(s). In certain embodiments, the pharmaceutical composition includes one or two diluent(s). In particular embodiments, the diluent is selected from mannitol, microcrystalline cellulose, lactose, dextrose, sucrose, ludiflash, F-melt, advantose, GalenIQ, and any mixtures thereof. In one embodiment, the diluent is mannitol, microcrystalline cellulose, or a mixture thereof.

In some embodiments, the pharmaceutical composition includes at least one disintegrant. In certain embodiments, the pharmaceutical composition includes one disintegrant. In a particular embodiment, the disintegrant is sodium starch glycolate. In one embodiment, the disintegrant is croscarmellose sodium. In another embodiment, the disintegrant is crospovidone.

In some embodiments, the pharmaceutical composition includes at least one glidant. In certain embodiments, the pharmaceutical composition includes one glidant. In one embodiment, the glidant is colloidal silicon dioxide.

In some embodiments, the pharmaceutical composition includes at least one lubricant. In certain embodiments, the pharmaceutical composition includes one lubricant. In one embodiment, the lubricant is magnesium stearate.

In particular embodiments, the pharmaceutical composition includes MMB dihydrochloride monohydrate Form II, at least one diluent, at least one disintegrant, at least one glidant, at least one lubricant, and at least one anti-oxidant. In further embodiments, the at least one diluent is microcrystalline cellulose, the at least one disintegrant is sodium starch glycolate, the at least one glidant is colloidal silicon dioxide, the at least one lubricant is magnesium stearate, and at least one anti-oxidant is propyl gallate. In yet further embodiments, the at least one diluent is lactose, the at least one disintegrant is sodium starch glycolate, the at least one glidant is colloidal silicon dioxide, the at least one lubricant is magnesium stearate, and at least one anti-oxidant is propyl gallate.

In other embodiments, the pharmaceutical composition includes MMB dihydrochloride monohydrate Form II, at least two diluents, at least one disintegrant, at least one glidant, at least one lubricant, and at least one anti-oxidant. In yet other embodiments, the at least two diluents are microcrystalline cellulose and lactose, the at least one disintegrant is sodium starch glycolate, the at least one glidant is colloidal silicon dioxide, the at least one lubricant is magnesium stearate, and at least one anti-oxidant is propyl gallate.

In certain embodiments, the pharmaceutical composition includes MMB compound of which at least about 80% is MMB dihydrochloride monohydrate Form II. In further embodiments, the pharmaceutical composition includes MMB compound of which at least about 85% is MMB dihydrochloride monohydrate Form II. In still further embodiments, the pharmaceutical composition includes MMB compound of which at least about 90% is MMB dihydrochloride monohydrate Form II. In yet further embodiments, the pharmaceutical composition includes MMB compound of which at least about 95% is MMB dihydrochloride monohydrate Form II. In particular embodiments, the pharmaceutical composition includes MMB compound of which at least about 97% is MMB dihydrochloride monohydrate Form II. In other embodiments, the pharmaceutical composition includes MMB compound of which at least about 98% is MMB dihydrochloride monohydrate Form II. In still other embodiments, the pharmaceutical composition includes MMB compound of which at least about 99% is MMB dihydrochloride monohydrate Form II. In yet other embodiments, the pharmaceutical composition includes MMB compound of which at least about 99.5% is MMB dihydrochloride monohydrate Form II. In particular embodiments, the pharmaceutical composition includes MMB compound of which at least about 99.9% is MMB dihydrochloride monohydrate Form II.

It should be understood that the pharmaceutical composition includes pharmaceutically acceptable carriers detailed herein, the same as if each and every combination of pharmaceutically acceptable carrier were specifically and individually listed.

Unit Dosage Forms

In some embodiments, the pharmaceutical compositions as described herein are formulated in a unit dosage form. The term "unit dosage forms" refers to physically discrete units suitable as unitary dosages for subjects (e.g., human subjects and other mammals), each unit containing a predetermined quantity of MMB compound active material calculated to produce the desired therapeutic effect, in association with a suitable pharmaceutical carrier.

In a further embodiment, the unit dosage forms include MMB dihydrochloride monohydrate Form II. In some embodiments, the unit dosage form includes MMB dihydrochloride monohydrate Form II in amount equivalent to from about 10 mg to about 1000 mg, about 10 mg to about 800 mg, about 10 mg to about 700 mg about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 10 mg to about 50 mg, about 50 mg to about 1000 mg, about 50 mg to about 800 mg, about 50 mg to about 700 mg about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 100 mg to about 1000 mgs, about 100 mg to about 800 mg, about 100 mg to about 700 mg about 100 mg to about 500 mg, about 100 mg to about 400 mg, about 100 mg to about 300 mg, about 100 mg to about 250 mg, about 100 mg to about 200 mg, about 150 mg to about 300 mg, about 150 mg to about 250 mg, about 150 mg to about 200 mg, about 200 mg to about 300 mg, about 200 mg to about 250 mg, or about 200 mg to about 300 mg of MMB free base.

In certain embodiments of the invention, the unit dosage form includes at least one pharmaceutically acceptable carrier. In other embodiments, the unit dosage form includes MMB dihydrochloride monohydrate Form II, at least two diluents, at least one disintegrant, at least one glidant, at least one lubricant, and at least one anti-oxidant. In still further embodiments, the unit dosage form includes about 36% to 44% MMB dihydrochloride monohydrate Form II; about 44% to 58% diluent; about 4% to 8% disintegrant, about 0.25% to 0.75% glidant, about 1.2% to 1.8% lubricant, and about 0.1% to 0.5% anti-oxidant. In yet other embodiments, the at least two diluents are microcrystalline cellulose and lactose, the at least one disintegrant is sodium starch glycolate, the at least one glidant is colloidal silicon dioxide, the at least one lubricant is magnesium stearate, and at least one anti-oxidant is propyl gallate. In still further embodiments, the unit dosage form includes about 36% to 44% MMB dihydrochloride monohydrate Form II; about 30% to 38% microcrystalline cellulose; about 14% to 20% lactose, about 4% to 8% sodium starch glycolate; about 0.25% to 0.75% colloidal silicon dioxide, about 1.2% to 1.8% magnesium stearate, and about 0.1% to 0.5% propyl gallate.

The pharmaceutical compositions described herein can be manufactured using any conventional method, such as, but not limited to, mixing, dissolving, granulating, dragee-making, levigating, emulsifying, encapsulating, entrapping, melt-spinning, spray-drying, or lyophilizing processes. A skilled artisan would recognize suitable methods and techniques to prepare a tablet by conventional formulation. Exemplary methods and techniques to prepare powders for compression into a tablet include dry granulation or wet granulation. Dry granulation generally refers to the process of forming granules without using a liquid solution, whereas wet granulation generally refers to the process of adding a liquid solution to powders to granulate.

Ruxolitinib Therapy

Aspects of this disclosure include methods of treating a subject for a MPN (e.g., as described herein) using MMB as a second line therapy. In some embodiments, the subject has been treated with a previous first line JAK inhibitor therapy, such as ruxolitinib or fedratinib. Further details of conventional ruxolitinib therapy of the SIMPLIFY 1 and 2 clinical trials are provided below.

Ruxolitinib is typically administrated BID in equally divided doses. The range of recommended doses for patients with myelofibrosis is 10-fold, from a high of 25 mg twice daily to a low of 5 mg once daily. The recommended starting dose of ruxolitinib is based on platelet count, with an attenuated starting dose of 15 mg twice daily recommended for patients whose pre-treatment platelet count is 100 to 200×109/L (Table 3). A complete blood count (CBC) and platelet count is performed before initiating therapy, every 2 to 4 weeks until doses are stabilized, and then as clinically indicated. Doses may be titrated based on safety and efficacy.

TABLE 3

Ruxolitinib starting doses

| Platelet Count | Starting Dose |
|---|---|
| Greater than 200 × 10$^9$/L | 20 mg orally twice daily |
| 100 × 10$^9$/L to 200 × 10$^9$/L | 15 mg orally twice daily |
| 50 × 10$^9$/L to less than 100 × 10$^9$/L | 5 mg orally twice daily |

Ruxolitinib dose modification guidelines for hematologic toxicity for patients with myelofibrosis starting treatment with a platelet count of 100×10$^9$/L or greater include treatment interruption and restarting dosing. Interrupt treatment for platelet counts less than 50×10$^9$/L or absolute neutrophil count (ANC) less than 0.5×10$^9$/L. After recovery of platelet counts above 50×10$^9$/L and ANC above 0.75×10$^9$/L, dosing may be restarted. Following treatment interruption for ANC below 0.5×10$^9$/L, after ANC recovers to 0.75×10$^9$/L or greater, restart dosing at the higher of 5 mg once daily or 5 mg twice daily below the largest dose in the week prior to the treatment interruption. Following treatment interruption for platelet count of less than 50×10$^9$/L and recover to above this threshold, the maximum restarting dose is displayed in Table 4.

TABLE 4

Myelofibrosis: Maximum restarting doses for RUX after safety interruption for thrombocytopenia for patients starting treatment with a platelet count of 100 × 10$^9$/L or greater

| Current Platelet Count | Maximum Dose when restarting RUX treatment |
|---|---|
| Greater than or equal to 125 × 10$^9$/L | 20 mg twice daily |
| 100 to less than 125 × 10$^9$/L | 15 mg twice daily |
| 75 to less than 100 × 10$^9$/L | 10 mg twice daily for at least 2 weeks; if stable, may increase to 15 mg twice daily |
| 50 to less than 75 × 10$^9$/L | 5 mg twice daily for at least 2 weeks; if stable, may increase to 10 mg twice daily |
| Less than 50 × 10$^9$/L | Continue hold |

Ruxolitinib dose reductions are considered if the platelet counts decrease as outlined in Tables 5 and 6 with the goal of avoiding dose interruptions for thrombocytopenia.

TABLE 5

Ruxolitinib dosing recommendations for thrombocytopenia for myelofibrosis patients starting treatment with a platelet count of 100 × 10$^9$/L or greater.

| | Dose at Time of Platelet Decline | | | | |
|---|---|---|---|---|---|
| Platelet Count | 25 mg twice daily New Dose | 20 mg twice daily New Dose | 15 mg twice daily New Dose | 10 mg twice daily New Dose | 5 mg twice daily New Dose |
| 100 to less than 125 × 10$^9$/L | 20 mg twice daily | 15 mg twice daily | No Change | No Change | No Change |
| 75 to less than 100 × 10$^9$/L | 10 mg twice daily | 10 mg twice daily | 10 mg twice daily | No Change | No Change |
| 50 to less than 75 × 10$^9$/L | 5 mg twice daily | 5 mg twice daily | 5 mg twice daily | 5 mg twice daily | No Change |
| Less than 50 × 10$^9$/L | Hold | Hold | Hold | Hold | Hold |

Ruxolitinib dose modifications for hematologic toxicity for patients with myelofibrosis starting treatment with platelet counts of 50×10$^9$/L to less than 100×10$^9$/L include treatment interruption and restarting dosing. Interrupt treatment for platelet counts less than 25×10$^9$/L or ANC less than 0.5×10$^9$/L. After recovery of platelet counts above 35×10$^9$/L and ANC above 0.75×10$^9$/L, ruxolitinib dosing may be restarted. Dosing can be restarted at the higher of 5 mg once daily or 5 mg twice daily below the largest dose in the week prior to the decrease in platelet count below 25×10$^9$/L or ANC below 0.5×10$^9$/L that led to dose interruption. Reduce the dose of ruxolitinib for platelet counts less than 35×10$^9$/L as described in Table 3.

TABLE 6

Ruxolitinib dosing modifications for thrombocytopenia for myelofibrosis patients with starting platelet count of 50 × 10$^9$/L to less than 100 × 10$^9$/L.

| Platelet Count | Dosing recommendations |
|---|---|
| Less than 25 × 10$^9$/L. | Interrupt dosing |
| 25 × 10$^9$/L to less than 35 × 10$^9$/L AND the platelet count decline is less than 20% during the prior four weeks | Decrease dose by 5 mg once daily For patients on 5 mg once daily maintain dose at 5mg once daily |
| 25 × 10$^9$/L to less than 35 × 10$^9$/L AND the platelet count decline is 20% or greater during the prior four weeks | Decrease dose by 5 mg twice daily For patients on 5 mg twice daily, decrease the dose to 5mg once daily For patients on 5 mg once daily, maintain dose at 5mg once daily |

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It must be noted that, as used in the specification and the appended claims, the singular forms "a," "an" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Below are examples of specific embodiments for carrying out the present invention. the examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: SIMPLIFY-1 and SIMPLIFY-2

Momelotinib (MMB) is a potent, selective, orally-bioavailable, small-molecule inhibitor of JAK1, JAK2 and ACVR1 that was developed for the treatment of myelofibrosis (MF). In two Phase three clinical trials for first-line and second-line treatment of MF (SIMPLIFY-1 and -2, respectively), however, MMB failed to meet all of the pre-defined secondary endpoints of TSS response in SIMPLIFY-1 and the primary endpoint of SRR in SIMPLIFY-2.

In the SIMPLIFY-1 trial (NCT01969838), the efficacy and safety of MMB versus ruxolitinib (RUX) was studied in patients with myelofibrosis who were naïve to treatment with a JAK inhibitor and a platelet count of $\geq 50 \times 10^9$/L. Patients (N=432) with high risk or intermediate-2 risk or symptomatic intermediate-1 risk myelofibrosis received 24 weeks of treatment with 200 mg MMB once daily or 20 mg RUX twice a day (or per label), after which all patients could receive open-label momelotinib. Efficacy was measured, with a goal of demonstrating non-inferiority of MMB to RUX, by spleen response, total symptom score (TSS), rate of red blood cell transfusion, and transfusion-independence or transfusion dependence. The primary endpoint was a reduction by at least 35% in the spleen volume at 24 weeks compared with baseline.

In the SIMPLIFY-2 trial (NCT02101268), the efficacy and safety of MMB was studied in anemic or thrombocytopenic subjects with myelofibrosis who were previously treated with ruxolitinib (RUX). Efficacy was measured, with a goal of demonstrating superiority of MMB over BAT, by spleen response, total symptom score (TSS), rate of red blood cell transfusion, and transfusion-independence or transfusion dependence. Specifically, anemic or thrombocytopenic myelofibrosis patients who had and were previously treated with (RUX) (for at least 28 days) were studied over 24 weeks for response to MMB versus best available treatment (BAT), primarily RUX (89% of patients) but alternatively no treatment or other standard interventions, after which period all patients could receive extended MMB treatment. Previously treated RUX patients who either required red blood cell transfusions or RUX dose reduction with grade 3 thrombocytopenia, anemia, and/or bleeding at grade 3 or worse, with palpable spleen of at least 5 cm and without grade 2 or greater peripheral neuropathy were included in the trial. There was no lower limit for the required baseline platelet count. The primary endpoint was a reduction by at least 35% in the spleen volume at 24 weeks compared with baseline.

Figure 8A:
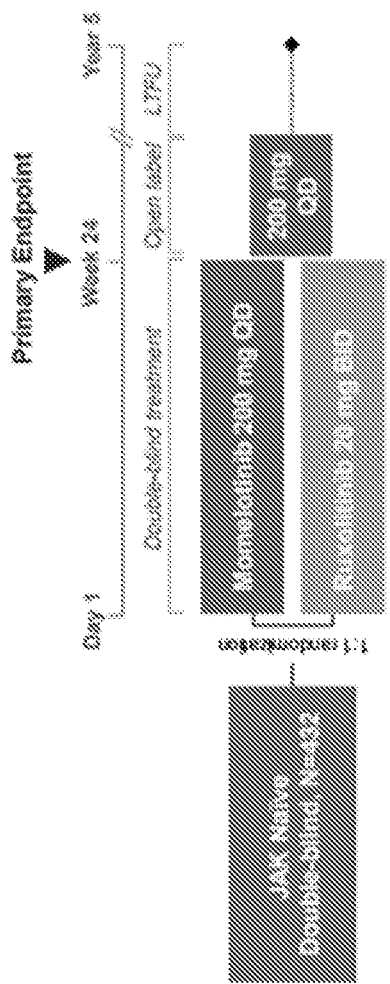
FIG. 8A-8B shows schematics summarizing the parameters of two completed Phase 3 studies with momelotinib (MMB) treatment of myelofibrosis: SIMPLIFY-1 and SIMPLIFY-2.
Figure 8B:
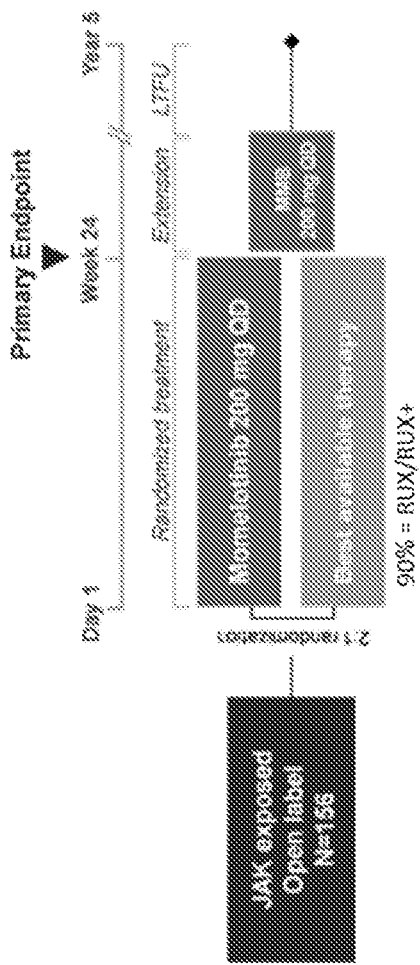

FIG. 8A-8B shows schematics summarizing the parameters of two completed Phase 3 studies with momelotinib (MMB) treatment of myelofibrosis: SIMPLIFY-1 and SIMPLIFY-2. FIG. 8A: SIMPLIFY-1 study of MMB in a first line population previously untreated with JAKi. For SIMPLIFY-1, the goal was non-inferiority over ruxolitinib (RUX) (MMB: N=215 subjects, and RUX: N=217 subjects). FIG. 8B: SIMPLIFY-2 study of second line population of anemic or thrombocytopenic subjects previously treated with RUX (red blood cell (RBC) transfusions on RUX=64%. RUX dose adjustment for: thrombocytopenia=21%; anemia/hematoma=35%). For SIMPLIFY-2, the goal was superiority over best available treatment (BAT) (MMB: N=104 subjects, and BAT: N=52 subjects). In both SIMPLIFY-1 and SIMPLIFY: Primary endpoint: >=35% reduction in spleen volume at 24 weeks. Secondary endpoints: Total symptom score (TSS) response at 24 weeks. Effects on RBC transfusion requirements.

An initial analysis of the results of the SIMPLIFY-1 trial was reported by Mesa et al. (SIMPLIFY-1: A Phase III Randomized Trial of Momelotinib Versus Ruxolitinib in Janus Kinase Inhibitor—Naive Patients with Myelofibrosis", J. Clinical Oncology 2017, 35(34):3844-3850). That analysis of the SIMPLIFY-1 trial data indicated momelotinib was noninferior to RUX for the reduction of spleen size in JAKi-näive patients, thus meeting the study's primary endpoint. However, non-inferiority was not demonstrated for the secondary endpoint of total symptom score (TSS) response despite evidence of momelotinib's demonstrable symptomatic benefits in symptomatic patients in that study. MMB treatment was associated with an increased transfusion independence rate; a decreased transfusion dependence rate and a reduced transfusion rate compared to RUX, all of which were nominally statistically-significant.

The results of the SIMPLIFY-2 trial were reported by Harrison et al. ("Momelotinib versus best available therapy in patients with myelofibrosis previously treated with ruxolitinib (SIMPLIFY 2): a randomised, open-label, phase 3 trial." Lancet Haematol; Volume 5, Issue 2, February 2018, Pages e73-e81). The interpretation of the SIMPLIFY-2 trial data indicated in momelotinib was not superior to BAT for the reduction of spleen size thus the trial failed to achieve its primary endpoint.

Although the key secondary endpoints were nominally significant in the analysis by Harrison et al., these were not considered statistically significant in the hierarchy of analysis endpoints. In general, patients in the momelotinib group has a greater a greater total symptom score (TSS) response, fewer transfusions, higher transfusion independence, and lower transfusion dependence compared to patients in the BAT group. The initial analysis was complicated by the failure to allow or even permit discontinuation of ruxolitinib prior to the start of randomized study treatment. By not including a mandatory washout from prior ruxolitinib, the evaluation of the splenic response was obscured in this study in subjects in either arm. In addition, patients enrolled in this study were not selected based on splenic progression on RUX.

Example 2: SIMPLIFY-1 and SIMPLIFY-2 Reanalyses

We have re-analyzed the data from the SIMPLIFY-1 and SIMPLIFY-2 trials and discovered that momelotinib is effective in reducing spleen size (SSR), improving total symptom scores (TSS), and improving transfusion independence rates in patients whose platelet counts are $150\times10^9$ per liter or below, without momelotinib administration causing thrombocytopenia, and without therefore requiring dose reduction or interruption for thrombocytopenia. Our reanalyses indicates MMB is effective in JAKi-näive patients and in patients as a second line therapy to RUX, providing benefits of reducing enlarged spleens, improving myelofibrosis-related symptoms, and increasing transfusion independence rates in a patient population with or at risk for thrombocytopenia from the underlying disease and from current standard of care.

Platelet Levels During MMB or RUX Treatment

FIG. 31 shows a plot of mean (±standard error) platelet counts for MMB versus RUX subjects in the SIMPLIFY 1 study over the 24 weeks of the double blind treatment phase. The mean platelet count for RUX patients is demonstrably lower than the mean platelet count for MMB patients.

FIG. 32 shows a plot of mean (±standard error) platelet count over time for double blind and open label treatment phases for MMB versus RUX of the SIMPLIFY 1 study (Intention-to-Treat (ITT) analysis).

FIG. 33 shows a plot of mean (±standard error) platelet count over time for randomized and extended treatment phases for MMB versus best available therapy (BAT) of the SIMPLIFY 2 study (Intention-to-Treat (ITT) analysis).

FIGS. 31-33 show plots of mean platelet counts for MMB versus RUX subjects in the SIMPLIFY 1 study which indicate that subjects treated with MMB were able to maintain platelet levels during treatment period, e.g., during the 24 week double blind phase of the study. In comparison, RUX subjects showed significant reductions in platelet counts from baseline, which in many cases can lead to necessary dose reduction (e.g., as described herein). The MMB subjects were thus at lower risk of developing thrombocytopenia (e.g., Grade 3 or 4 thrombocytopenia), or of having to undergo undesirable dose reduction because they were able to largely maintain their platelet counts during therapy.

FIGS. 32-33 also illustrate MMB's ability to recover platelets (rebound) upon switch from RUX to MMB after 24 weeks.

FIG. 34 shows a plot of mean daily dose in SIMPLIFY 1, by arm for each week of study during the 24 week double blind treatment phase. The vertical bars represent the proportion of subjects receiving the various doses. The vast majority of MMB subjects received 200 mg per day throughout the course of the study. In the RUX arm, less than half of the subjects were receiving a standard 40 mg/day (20 mg BID) and nearly a quarter were receiving only 10 mg/day (5 mg BID).

Figure 35:
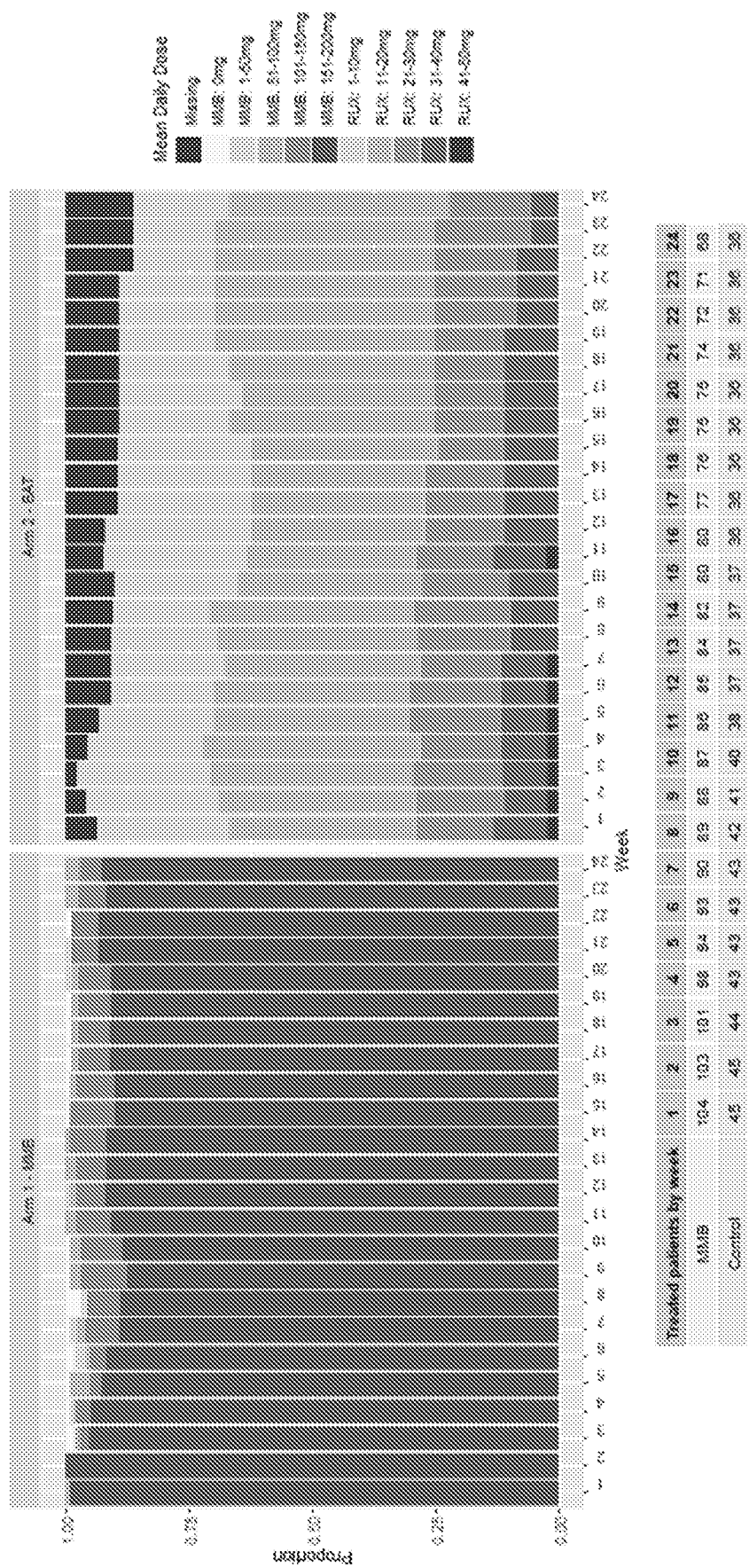
FIG. 35 shows dose categories by treatment for treated patients during the first 24 weeks of the SIMPLIFY 2 trial showing the drop in RUX doses and relative stability of MMB dose levels during treatment.

FIG. 35 shows a plot of mean daily dose in SIMPLIFY 2, by arm for each week of study during the 24 week randomized treatment phase. The vertical bars represent the proportion of subjects receiving the various doses. The vast majority of MMB subjects received 200 mg per day throughout the course of the study. In the BAT arm, the most common dose across the course of the study was 20 mg/day (10 mg BID), followed by 10 mg/day (5 mg BID). Very few subjects (approximately 10%) received 40 mg/day (20 mg BID).

FIGS. 34-35 show dose categories by treatment for treated patients of the SIMPLIFY 1 or 2 trials, respectively, indicating that there was a drop in RUX doses (dose reduction) and a relative stability of MMB dose levels during the 24 week treatment period.

Patient Responses According to Baseline Platelet Count Subgroups

SIMPLIFY 1 (S1)

The SIMPLIFY 1 clinical trial data was reanalyzed for subgroups of subjects having particular baseline platelet counts in the MMB versus RUX arms of the study.

Patient data was analyzed according to the following baseline platelet count (PLT) subgroups and in particular according to the threshold PLT of $150\times10^9$/L: 1) PLT<$50\times10^9$/L; 2) $50\times10^9$/L≤PLT<$100\times10^9$/L; 3) $100\times10^9$/L≤PLT<$150\times10^9$/L. The reanalyzed data is presented in Table 13 (SIMPLIFY 1). Selected data is also illustrated in the following figures.

The data presented in Tables 7-9 show that in general, for each endpoint (TSS, SRR and Week 24 TI rate), the response rates for RUX trended downwards (diminished efficacy) for subjects in Subgroups 2 ($50\times10^9$/L≤PLT<$100\times10^9$/L) and 3 ($100\times10^9$/L≤PLT<$150\times10^9$/L) relative to the ITT response rate with most results falling outside of the 95% CI of the result achieved for each endpoint. Response rates for RUX subjects who were symptomatic at initiation of RUX therapy (TSS≥6, or TSS≥10) are consistent with this observation.

The analysis indicates efficacy (SRR, TSS, TI) is diminished or greatly diminished with RUX in patients with low platelets (subgroups 2-3) and is contraindicated for patients whose platelets are <50K×10$^9$/L (subgroup 1) (not shown).

TABLE 7

SIMPLIFY 1, RUX (Control) TSS

|  | All patients | Platelets 100-150 (subgroup 3) | Platelets 50-100 (subgroup 2) |
| --- | --- | --- | --- |
| ITT | 41% | 39%* | 22% |
| TSS ≥ 6 | 42% | 33% | 23% |
| TSS ≥ 10 | 43% | 35% | 21% |

(*point estimate was within the 95% confidence interval (CI) for all patients; all other values in the table were outside of 95% CI)

TABLE 8

SIMPLIFY 1, RUX (Control) SRR

|  | All patients | Platelets 100-150 (subgroup 3) | Platelets 50-100 (subgroup 2) |
| --- | --- | --- | --- |
| ITT | 29% | 6% | 0% |
| TSS >/= 6 | 29% | 7% | 0% |
| TSS >/= 10 | 29% | 5% | 0% |

(all values in the table were outside of 95% CI of all patients)

TABLE 9

SIMPLIFY 1, RUX (Control) Week 24 TI rate

|  | All patients | Platelets 100-150 (subgroup 3) | Platelets 50-100 (subgroup 2) |
| --- | --- | --- | --- |
| ITT | 49% | 45%* | 39% |
| TSS ≥ 6 | 48% | 41% | 36% |
| TSS ≥ 10 | 51% | 45%* | 32% |

(*point estimate was within the 95% confidence interval (CI) for all patients; all other values in the table were outside of 95% CI for all patients)

Tables 10-12 show an analysis of the data for the MMB arm of SIMPLIFY 1 according to baseline platelet counts that corresponds to Tables 7-9. The data presented in Tables 10-12 show that in general, for each endpoint (TSS, SRR and Week 24 TI rate), the response rates for MMB remains consistent in Subgroups 2 (50×10$^9$/L≤PLT<100×10$^9$/L) and 3 (100×10$^9$/L≤PLT<150×10$^9$/L) relative to the ITT response rate with most results remaining within the 95% CI of the result achieved for each endpoint. Response rates for MMB subjects who were symptomatic at initiation of MMB therapy (TSS≥6, or TSS≥10) are consistent with this observation.

TABLE 10

SIMPLIFY 1, MMB TSS

|  | All patients | Platelets 100-150 (subgroup 3) | Platelets 50-100 (subgroup 2) |
| --- | --- | --- | --- |
| ITT | 28% | 24% | 33% |
| TSS ≥ 6 | 33% | 32% | 36% |
| TSS ≥ 10 | 33% | 32% | 36% |

(all values in the table were within the 95% CI for all patients)

TABLE 11

SIMPLIFY 1, MMB SRR

|  | All patients | Platelets 100-150 (subgroup 3) | Platelets 50-100 (subgroup 2) |
| --- | --- | --- | --- |
| ITT | 27% | 14% ‡ | 39% |
| TSS ≥ 6 | 25% | 14% ‡ | 43% |
| TSS ≥ 10 | 24% | 13% ‡ | 42% |

(‡ point estimate was outside of the 95% confidence interval (CI) for all patients; all other values in the table were within the 95% CI for all patients)

TABLE 12

SIMPLIFY 1, MMB Week 24 TI rate

|  | All patients | Platelets 100-150 (subgroup 3) | Platelets 50-100 (subgroup 2) |
| --- | --- | --- | --- |
| ITT | 67% | 62% | 61% |
| TSS ≥ 6 | 67% | 68% | 64% |
| TSS ≥ 10 | 67% | 68% | 64% |

(all values in the table were within the 95% CI for all patients)

In contrast to the generally deteriorating responses shown for RUX patients, the MMB subjects of subgroups 3 and 2 generally demonstrated stable efficacy (e.g., TSS and TI rate at 24 weeks) as compared to the response for all patients.

Although the splenic response rate (SRR) for subgroup 3 (Table 11) was below the response determined for all MMB patients and subgroup 2 patient, this subgroup 3 SRR rate was still higher for MMB versus RUX for this subgroup.

Figure 36:
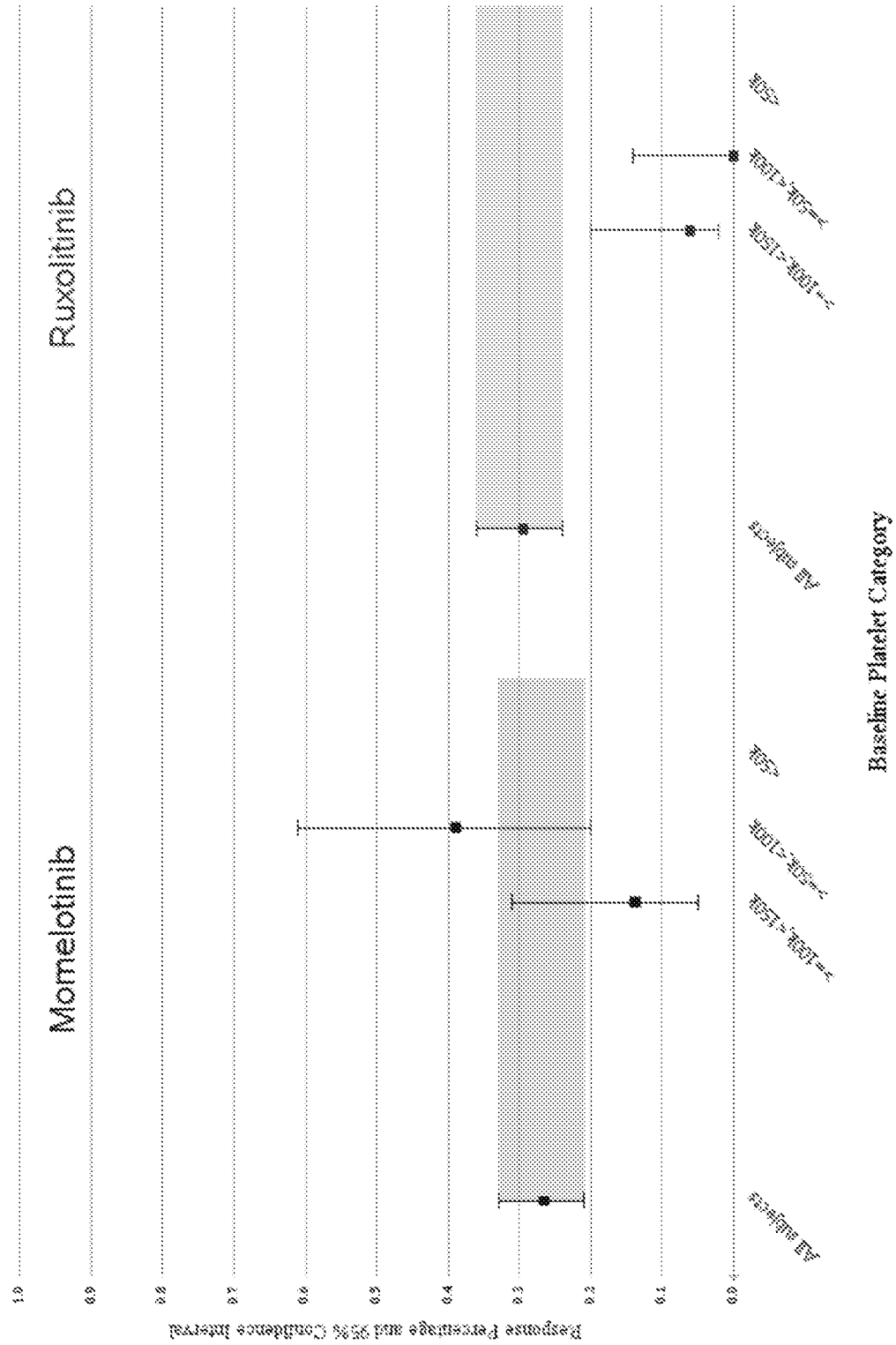
FIG. 36 shows a graph of splenic response rate (SRR) at week 24 versus baseline platelet count subgroup for all MMB or control (i.e., RUX) patients treated in the SIMPLIFY 1 study. The horizontal bars in the graphs of FIGS. 36-47 indicate 95% confidence intervals for mean response for all patients (All pts).

FIG. 36 shows a graph of splenic response rate (SRR) at week 24 versus baseline platelet count subgroup for all MMB or RUX patients treated in the SIMPLIFY 1 study. The horizontal bars indicate 95% confidence intervals for mean response for all patients (All pts).

Figure 38:
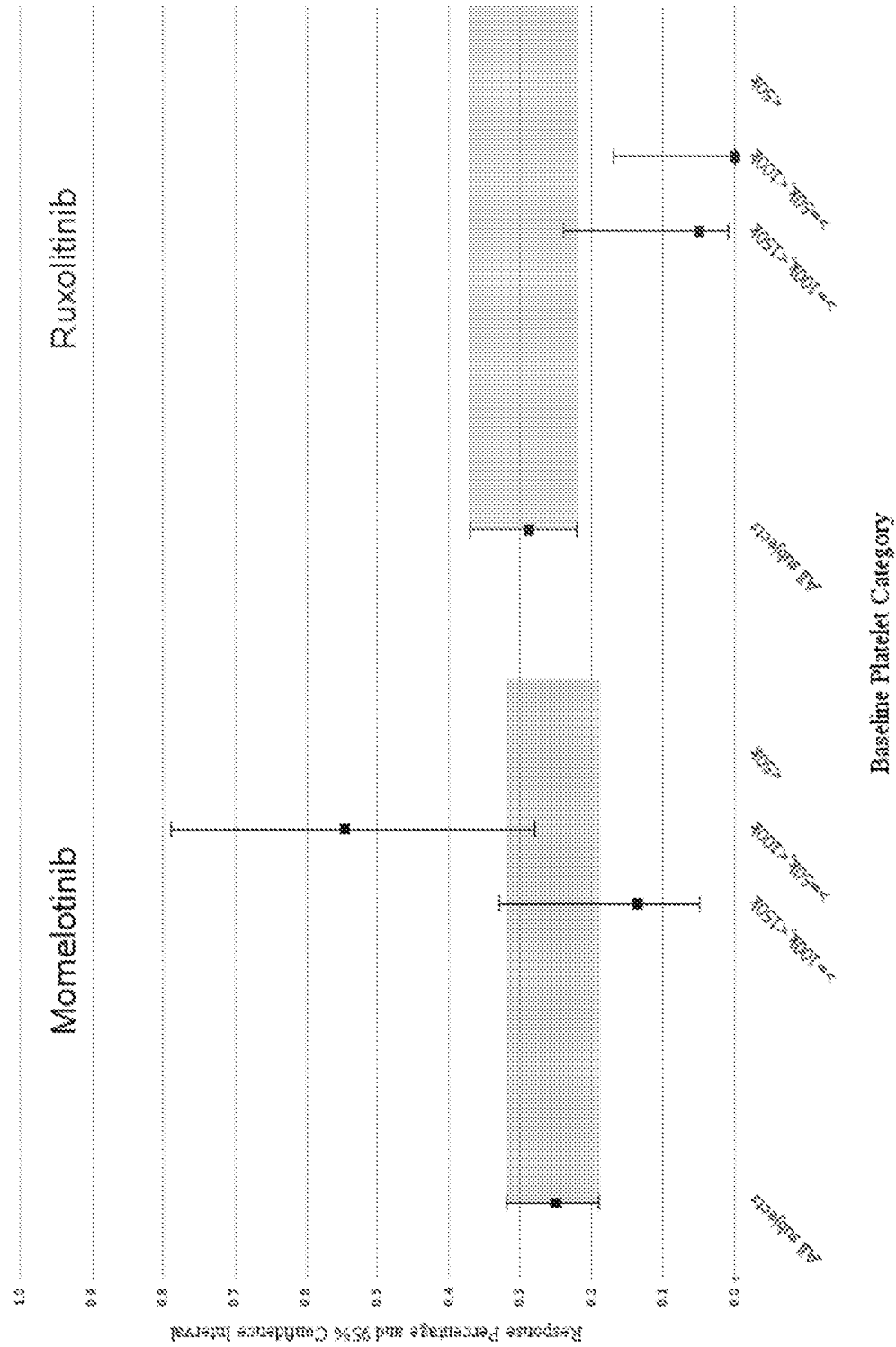
FIG. 38 shows a graph of SRR at week 24 versus baseline platelet count subgroup for symptomatic (e.g., baseline TSS of 10 or more) MMB or control (i.e., RUX) patients treated in the SIMPLIFY 1 study.

FIGS. 37-38 show a graph of splenic response rate (SRR) at week 24 versus baseline platelet count subgroup for symptomatic (e.g., TSS of 6 or more, or 10 or more, respectively) MMB or RUX patients treated in the SIMPLIFY 1 study. The horizontal bars indicate 95% confidence intervals for mean response for all patients (All pts).

Figure 39:
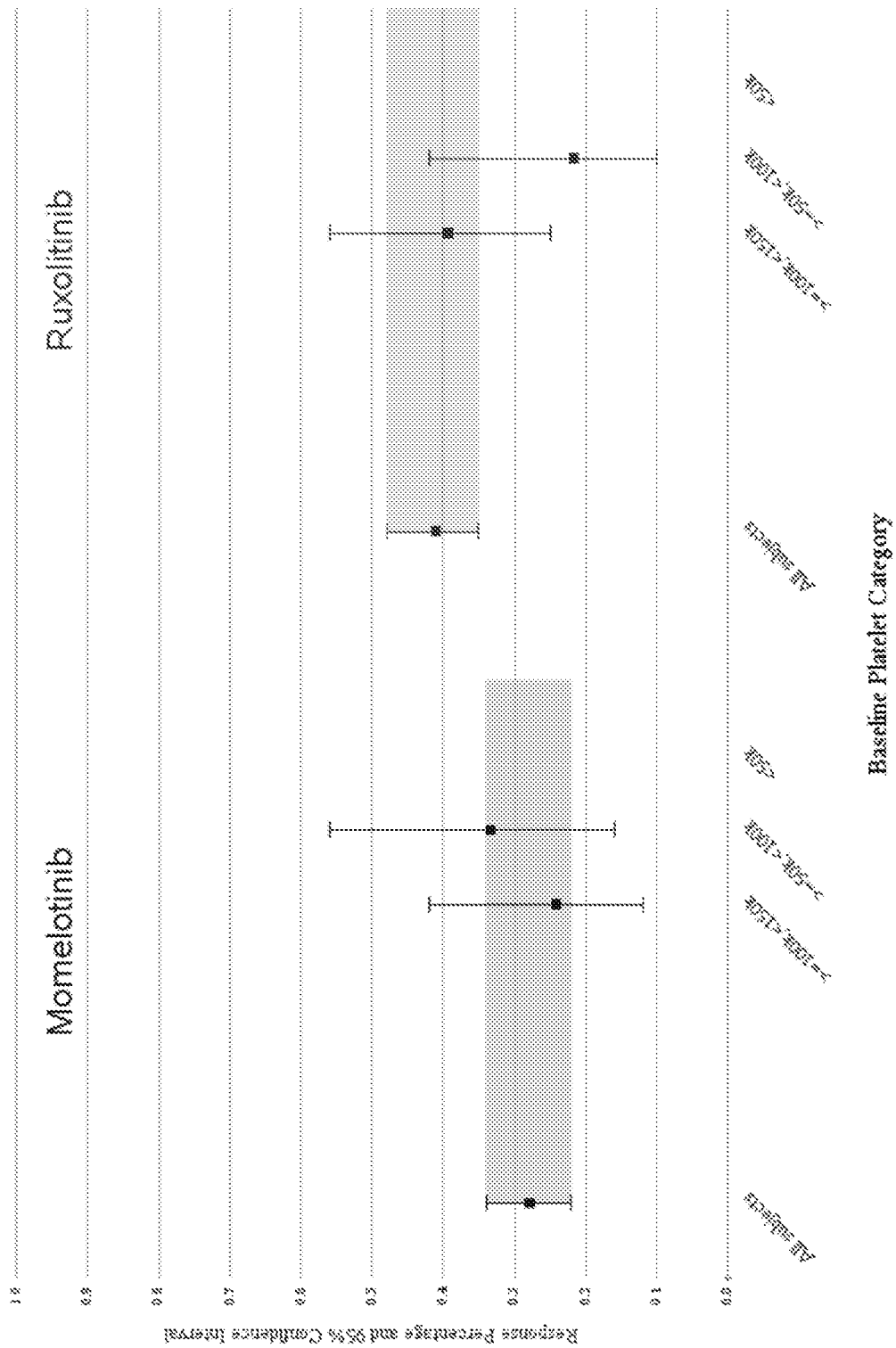
FIG. 39 shows a graph of total symptom score (TSS) at week 24 versus baseline platelet count subgroup for all MMB or control (i.e., RUX) patients treated in the SIMPLIFY 1 study.
Figure 41:
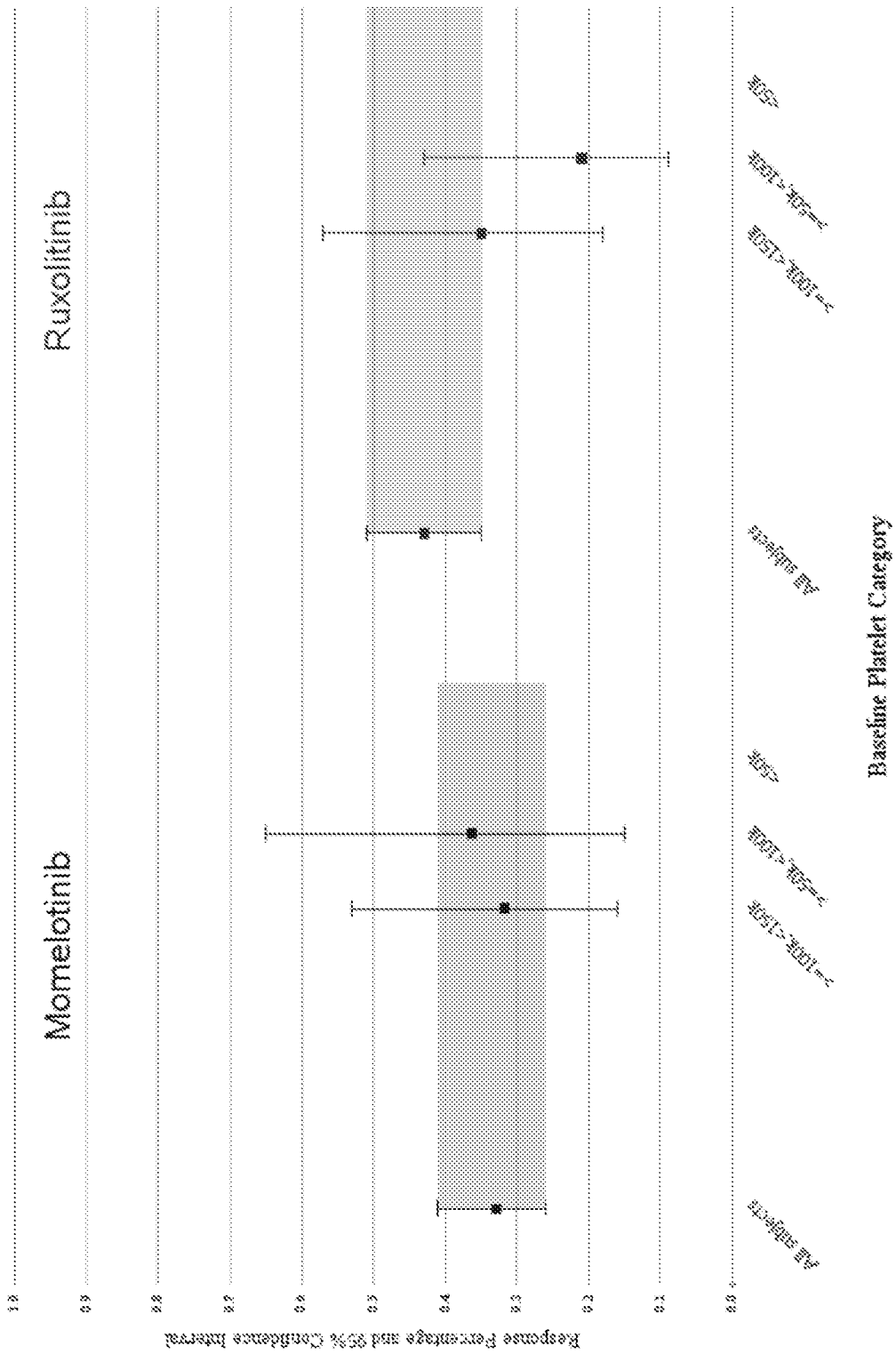
FIG. 41 shows a graph of TSS at week 24 versus baseline platelet count subgroup for symptomatic (e.g., baseline TSS of 10 or more) MMB or control (i.e., RUX) patients treated in the SIMPLIFY 1 study.
Figure 42:
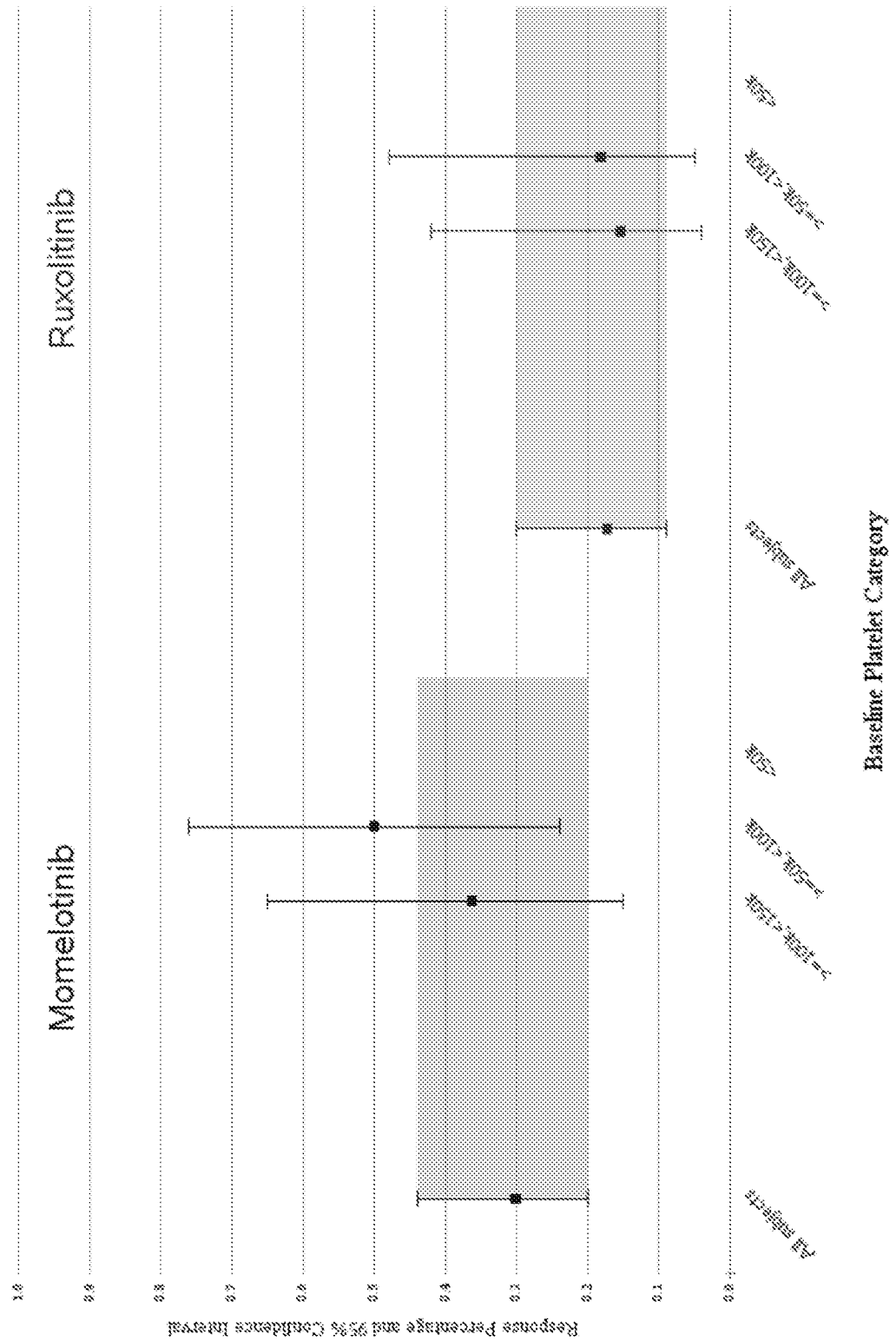
FIG. 42 shows a graph of rate of transfusion dependence (TD) to independence (TI) conversion at week 24 versus baseline platelet count subgroup for all MMB or control (i.e., RUX) patients treated in the SIMPLIFY 1 study.
Figure 44:
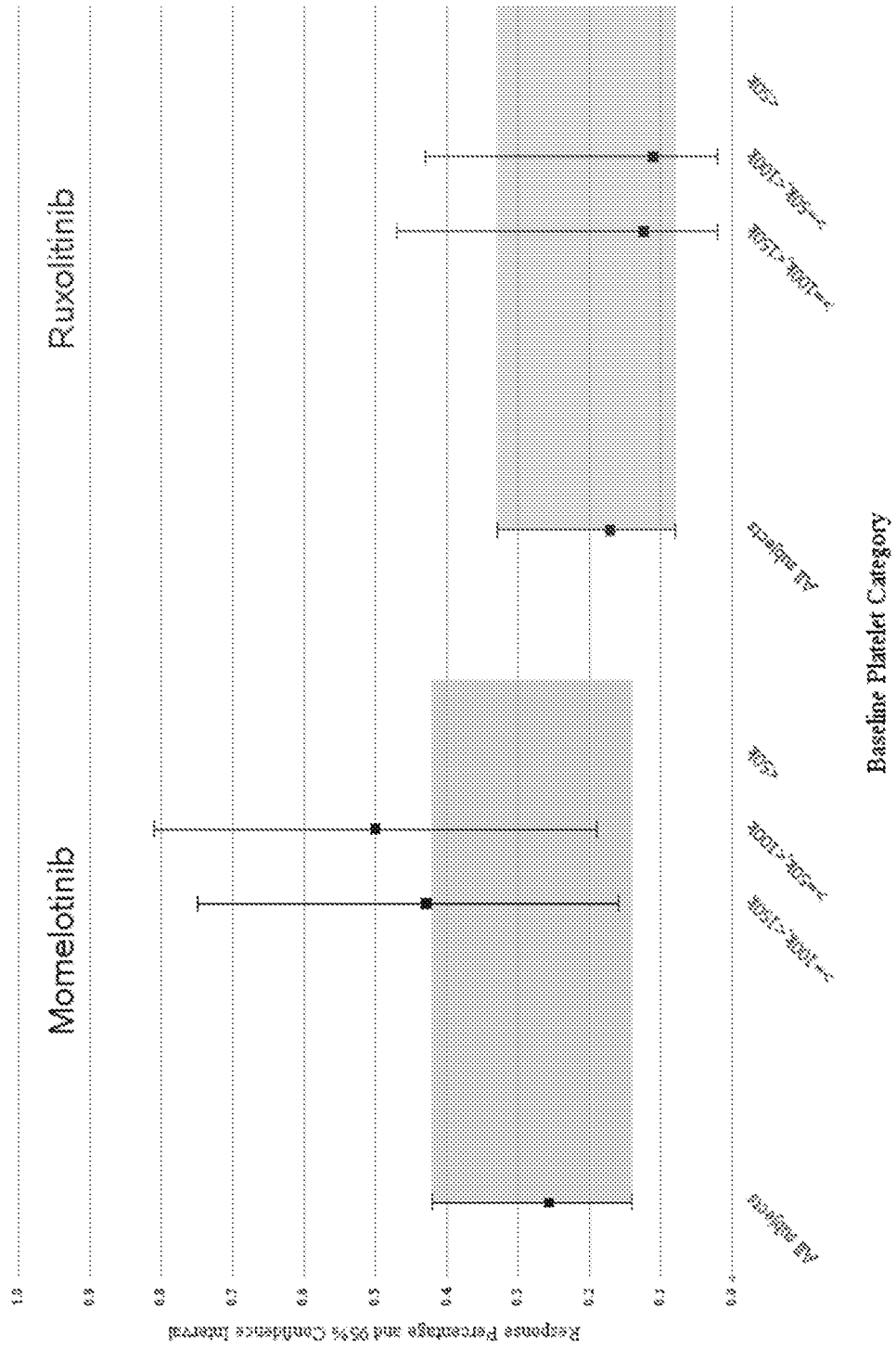
FIG. 44 shows a graph of rate of TD to TI at week 24 versus baseline platelet count subgroup for symptomatic (e.g., baseline TSS of 10 or more) MMB or control (i.e., RUX) patients treated in the SIMPLIFY 1 study.
Figure 45:
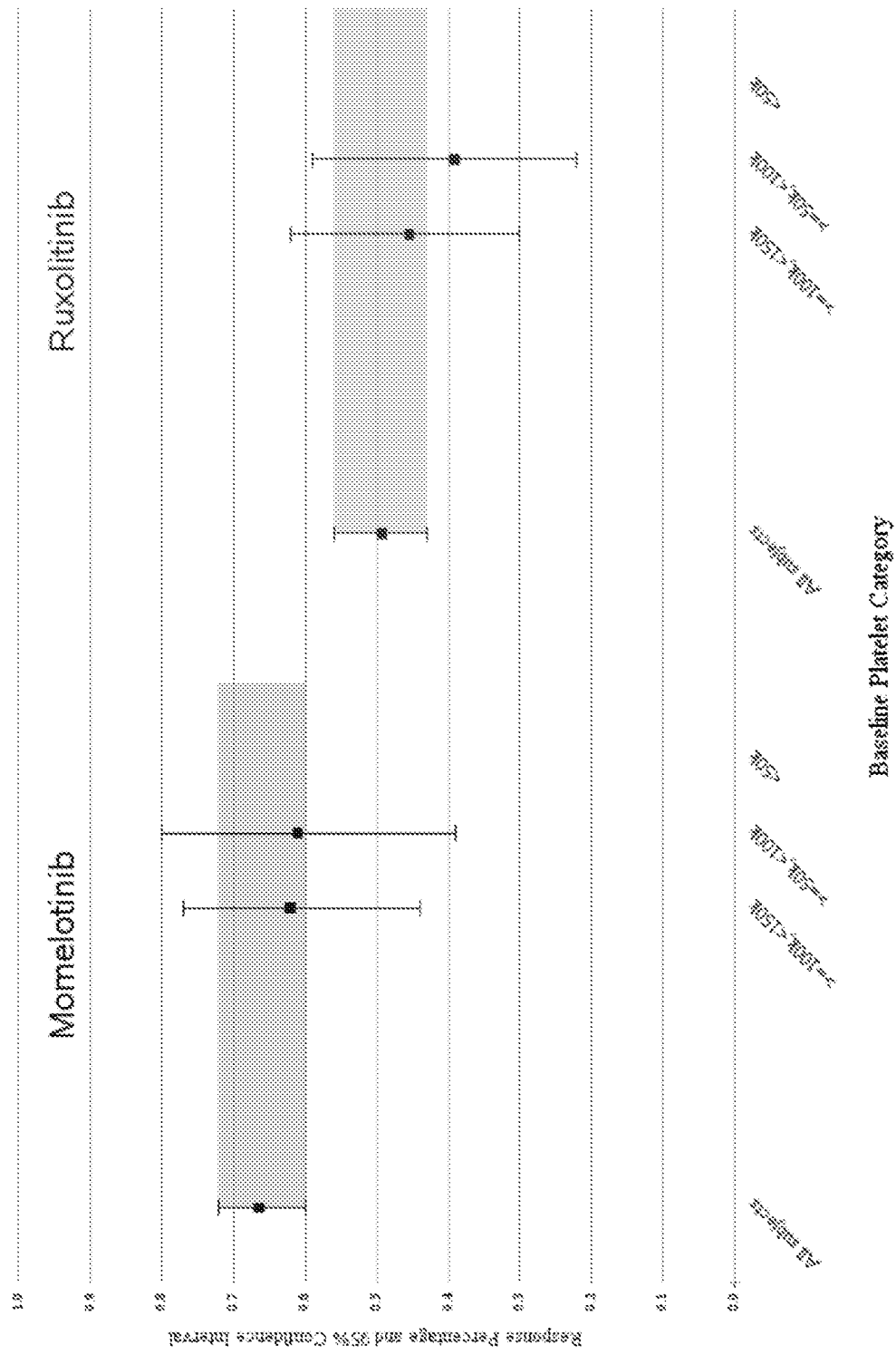
FIG. 45 shows a graph of transfusion independence (TI) response at week 24 versus baseline platelet count subgroup for all MMB or control (i.e., RUX) patients treated in the SIMPLIFY 1 study.
Figure 46:
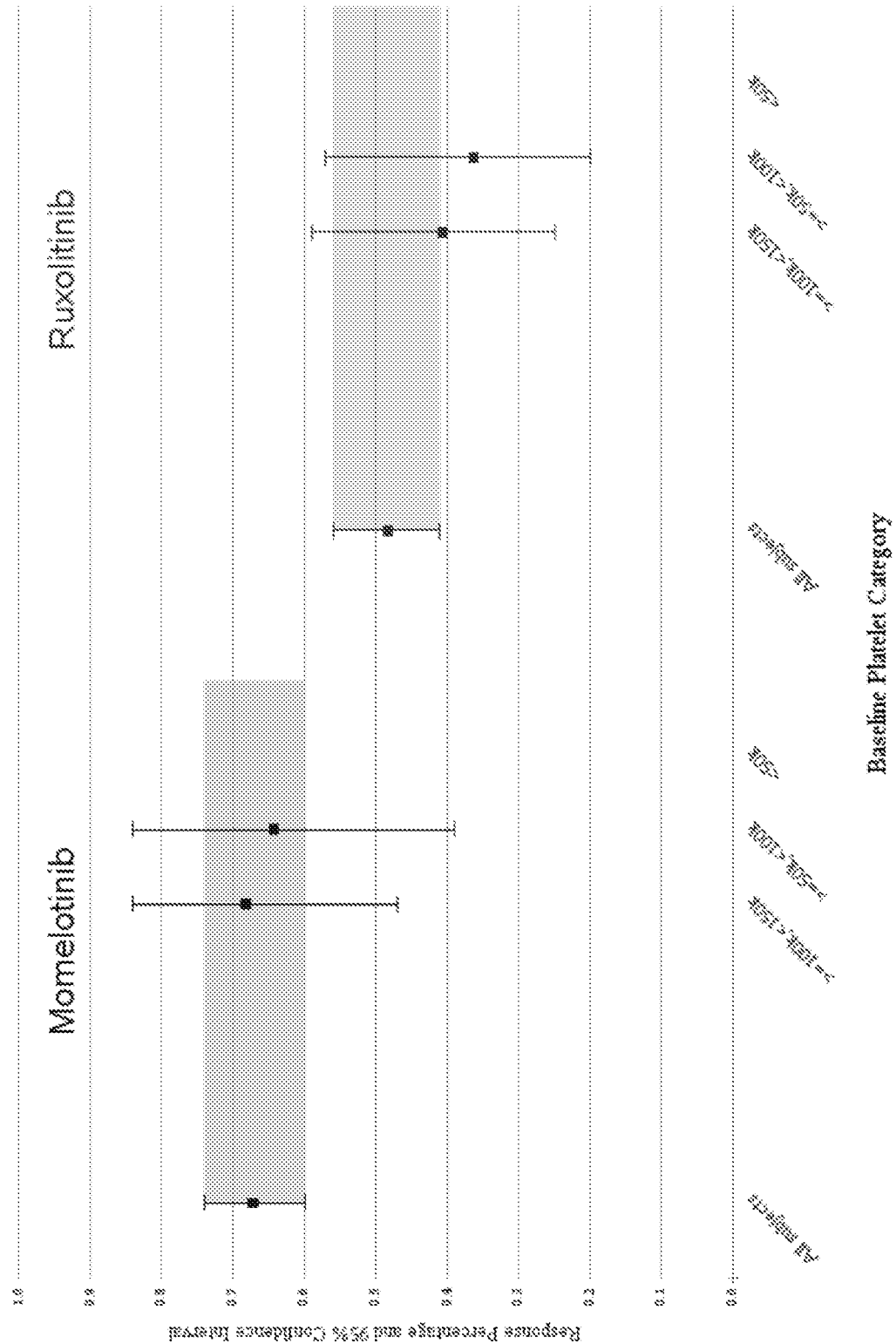
FIG. 46 shows a graph of TI response at week 24 versus baseline platelet count subgroup for symptomatic (e.g., baseline TSS of 6 or more) MMB or control (i.e., RUX) patients treated in the SIMPLIFY 1 study.
Figure 47:
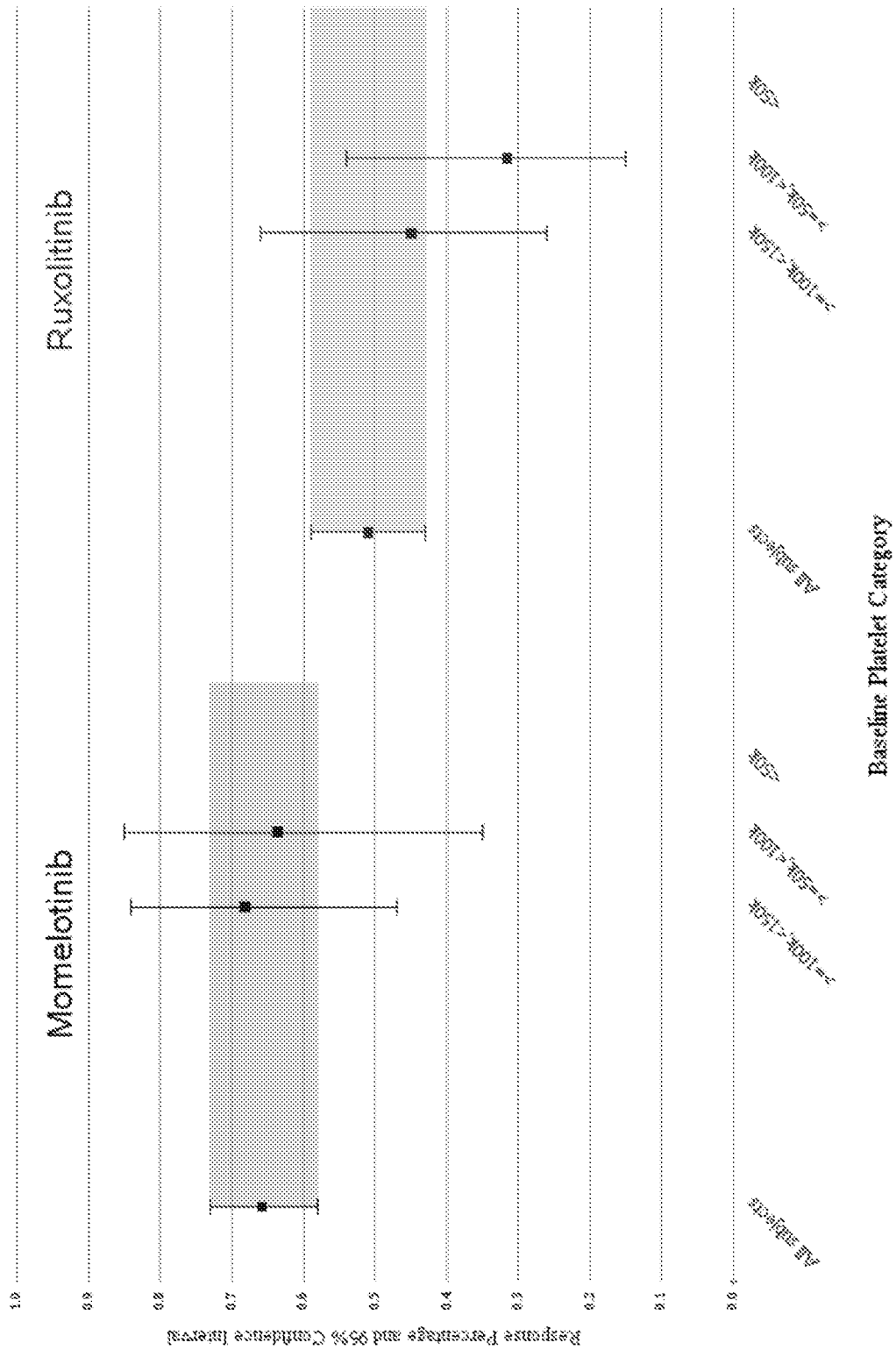
FIG. 47 shows a graph of TI response at week 24 versus baseline platelet count subgroup for symptomatic (e.g., baseline TSS of 10 or more) MMB or control (i.e., RUX) patients treated in the SIMPLIFY 1 study.

FIGS. 42-44 show similar results for rates of transfusion dependence to independence conversion at week 24. FIGS. 39-41 show similar results for symptom response rates (TSS). FIGS. 45-47 show similar results for TI response at week 24.

These graphs and tables illustrate that momelotinib therapy can provide a desirable therapeutic benefit to myelofibrosis patients having baseline platelet counts of 150× 10$^9$/L or less in in comparison to conventional ruxolitinib therapy. FIG. 36 illustrates that the splenic response rate (SRR) of MMB patients of the SIMPLIFY 1 study was better than RUX patients when the JAKi-näive myelofibrosis patients had baseline platelet count of 150×10$^9$/L or less, such as 100×10$^9$/L or less. That advantage of MMB over conventional RUX therapy was shown to be more pronounced when the subject was also symptomatic at initiation of therapy, e.g., the subject had a Total Symptom Score (TSS) of 6 or more (FIG. 37), such as 10 or more (FIG. 38). Similar advantages were discovered for transfusion dependence to independence conversion rates (FIGS. 42-44), and symptom response rates (FIGS. 39-41).

SIMPLIFY 2 (S2)

The SIMPLIFY 2 clinical trial data was reanalyzed for subgroups of subjects having particular baseline platelet counts in the MMB versus BAT arms of the study.

Patient data was analyzed according to the following baseline platelet count (PLT) subgroups and in particular according to a threshold PLT of $150\times10^9$/L: 1) PLT<$50\times10^9$/L; 2) $50\times10^9$/L≤PLT<$100\times10^9$/L; 3) $100\times10^9$/L≤PLT<$150\times10^9$/L. The reanalyzed data is presented in Table 14 (SIMPLIFY 2).

From the SIMPLIFY 2 data we know that MMB can be dosed at full dose in patients irrespective of platelet count including in those whose platelets are <$50\times10^9$/L. SRR, TSS, TI efficacy results are maintained with MMB in patients with platelets of 50 to $100\times10^9$/L (subgroup 2) and are maintained for the TSS and TI endpoint in patients with platelets of 100 to $150\times10^9$/L (subgroup 3).

The SIMPLIFY 2 study is a smaller study overall (<⅓ the size of SIMPLIFY 1) and thus the number of patients in the baseline platelet count subgroups are all smaller with more inherent variability across the results.

In general, the analysis of Table 14 shows superior outcomes for MMB subjects, as compared to BAT subjects, in the baseline platelet count subgroups<$150\times10^9$/L, for all endpoints except SRR. For example, for MMB subjects in the baseline platelet count subgroup 3 (100 to $150\times10^9$/L), the transfusion dependence to independence conversion rate at week 24 was 46% versus 9% for BAT subjects.

These results are generally consistent with those shown above for SIMPLIFY 1. However, due to the inherent variability of data in the smaller SIMPLIFY 2 study, conclusions were not drawn about the magnitude of the clinical benefits provided to the low baseline platelet count subgroup patients by MMB therapy.

TABLE 13

Response rates at 24 weeks for patient sub-groups of SIMPLIFY 1 study.
Outcomes: TSS is total symptom score; SRR is splenic response rate: TI rate is transfusion independent at weeks 24; TD to W24 TI is conversion from transfusion dependent at initiation of treatment to transfusion independent by week 24; TD to 12w rolling TI is conversion from transfusion dependent at initiation of treatment to transfusion indepencence for 12 consecutive weeks during treatment.
ITT = intention to treat. Subgroups: 1) PLT < $50 \times 10^9$/L 2) $50 \times 10^9$/L ≤ PLT < $100 \times 10^9$/L; 3) $100 \times 10^9$/L ≤ PLT < $150 \times 10^9$/L
N is number of subjects.

| Outcome | Subgroup Baseline Platelet Counts (PLT × $10^9$/L) | MMB (N) | MMB Responders | MMB proportion (Wilson 95% CI) | Control (N) | Control Responders | Control proportion (Wilson 95% CI) | Absolute risk difference (Newcombe 95% CI) |
|---|---|---|---|---|---|---|---|---|
| TSS | 50 ≤ PLT < 100 | 18 | 6 | 0.33 (0.16; 0.56) | 23 | 5 | 0.22 (0.10; 0.42) | 0.12 (−0.15; 0.37) |
| TSS | 100 ≤ PLT < 150 | 29 | 7 | 0.24 (0.12; 0.42) | 33 | 13 | 0.39 (0.25; 0.56) | −0.15 (−0.36; 0.08) |
| TSS | ITT | 215 | 60 | 0.28 (0.22; 0.34) | 217 | 89 | 0.41 (0.35; 0.48) | −0.13 (−0.22; −0.04) |
| SRR | 50 ≤ PLT < 100 | 18 | 7 | 0.39 (0.20; 0.61) | 23 | 0 | 0.00 (0.00; 0.14) | 0.39 (0.15; 0.61) |
| SRR | 100 ≤ PLT < 150 | 29 | 4 | 0.14 (0.05; 0.31) | 33 | 2 | 0.06 (0.02; 0.20) | 0.08 (−0.08; 0.25) |
| SRR | ITT | 215 | 57 | 0.27 (0.21; 0.33) | 217 | 64 | 0.29 (0.24; 0.36) | −0.03 (−0.11; 0.05) |
| TI rate | 50 ≤ PLT < 100 | 18 | 11 | 0.61 (0.39; 0.80) | 23 | 9 | 0.39 (0.22; 0.59) | 0.22 (−0.08; 0.47) |
| TI rate | 100 ≤ PLT < 150 | 29 | 18 | 0.62 (0.44; 0.77) | 33 | 15 | 0.45 (0.30; 0.62) | 0.17 (−0.08; 0.38) |
| TI rate | ITT | 215 | 143 | 0.67 (0.60; 0.72) | 217 | 107 | 0.49 (0.43; 0.56) | 0.17 (0.08; 0.26) |
| TD to W24 TI | 50 ≤ PLT < 100 | 10 | 5 | 0.50 (0.24; 0.76) | 11 | 2 | 0.18 (0.05; 0.48) | 0.32 (−0.08; 0.61) |
| TD to W24 TI | 100 ≤ PLT < 150 | 11 | 4 | 0.36 (0.15; 0.65) | 13 | 2 | 0.15 (0.04; 0.42) | 0.21 (−0.13; 0.51) |
| TD to W24 TI | ITT | 53 | 16 | 0.30 (0.20; 0.44) | 52 | 9 | 0.17 (0.09; 0.30) | 0.13 (−0.03; 0.28) |
| TD to 12w rolling TI | 50 ≤ PLT < 100 | 10 | 4 | 0.40 (0.17; 0.69) | 11 | 2 | 0.18 (0.05; 0.48) | 0.22 (−0.16; 0.53) |
| TD to 12w rolling TI | 100 ≤ PLT < 150 | 11 | 5 | 0.45 (0.21; 0.72) | 13 | 4 | 0.31 (0.13; 0.58) | 0.15 (−0.21; 0.47) |
| TD to 12w rolling TI | ITT | 53 | 19 | 0.36 (0.24; 0.49) | 52 | 13 | 0.25 (0.15; 0.38) | 0.11 (−0.07; 0.27) |

TABLE 14

Response rates for patient sub-groups of SIMPLIFY 2 study.
ND is not determined

| Outcome | Subgroup Baseline Platelet Counts (PLT × 10$^9$/L) | MMB (N) | MMB Responders | MMB proportion (Wilson 95% CI) | Control (N) | Control Responders | Control proportion (Wilson 95% CI) | Absolute risk difference (Newcombe 95% CI) |
|---|---|---|---|---|---|---|---|---|
| TSS | PLT < 50 | 9 | 1 | 0.11 (0.02; 0.43) | 7 | 1 | 0.14 (0.03; 0.51) | −0.03 (−0.41; 0.31) |
| TSS | 50 ≤ PLT < 100 | 33 | 9 | 0.27 (0.15; 0.44) | 20 | 0 | 0.00 (0.00; 0.16) | 0.27 (0.07; 0.44) |
| TSS | 100 ≤ PLT < 150 | 24 | 6 | 0.25 (0.12; 0.45) | 10 | 0 | 0.00 (0.00; 0.28) | 0.25 (−0.06; 0.45) |
| TSS | ITT | 104 | 27 | 0.26 (0.18; 0.35) | 52 | 3 | 0.06 (0.02; 0.16) | 0.20 (0.08; 0.30) |
| SRR | PLT < 50 | 9 | 0 | 0.00 (0.00; 0.30) | 7 | 0 | 0.00 (0.00; 0.35) | ND |
| SRR | 50 ≤ PLT < 100 | 33 | 1 | 0.03 (0.01; 0.15) | 20 | 1 | 0.05 (0.01; 0.24) | −0.02 (−0.21; 0.11) |
| SRR | 100 ≤ PLT < 150 | 24 | 3 | 0.13 (0.04; 0.31) | 10 | 1 | 0.10 (0.02; 0.40) | 0.03 (−0.29; 0.23) |
| SRR | ITT | 104 | 7 | 0.07 (0.03; 0.13) | 52 | 3 | 0.06 (0.02; 0.16) | 0.01 (−0.09; 0.08) |
| TI rate | PLT < 50 | 9 | 2 | 0.22 (0.06; 0.55) | 7 | 0 | 0.00 (0.00; 0.35) | 0.22 (−0.17; 0.55) |
| TI rate | 50 ≤ PLT < 100 | 33 | 18 | 0.55 (0.38; 0.70) | 20 | 8 | 0.40 (0.22; 0.61) | 0.15 (−0.12; 0.38) |
| TI rate | 100 ≤ PLT < 150 | 24 | 10 | 0.42 (0.24; 0.61) | 10 | 0 | 0.00 (0.00; 0.28) | 0.42 (0.09; 0.61) |
| TI rate | ITT | 104 | 45 | 0.43 (0.34; 0.53) | 52 | 11 | 0.21 (0.12; 0.34) | 0.22 (0.06; 0.35) |
| TD to W24 TI | PLT < 50 | 6 | 2 | 0.33 (0.10; 0.70) | 4 | 0 | 0.00 (0.00; 0.49) | 0.33 (−0.21; 0.70) |
| TD to W24 TI | 50 ≤ PLT < 100 | 13 | 6 | 0.46 (0.23; 0.71) | 11 | 1 | 0.09 (0.02; 0.38) | 0.37 (0.00; 0.63) |
| TD to W24 TI | 100 ≤ PLT < 150 | 13 | 4 | 0.31 (0.13; 0.58) | 5 | 0 | 0.00 (0.00; 0.43) | 0.31 (−0.16; 0.58) |
| TD to W24 TI | ITT | 58 | 19 | 0.33 (0.22; 0.46) | 27 | 1 | 0.04 (0.01; 0.18) | 0.29 (0.11; 0.42) |
| TD to 12w rolling TI | PLT < 50 | 6 | 3 | 0.50 (0.19; 0.81) | 4 | 0 | 0.00 (0.00; 0.49) | 0.50 (−0.08; 0.81) |
| TD to 12w rolling TI | 50 ≤ PLT < 100 | 13 | 7 | 0.54 (0.29; 0.77) | 11 | 3 | 0.27 (0.10; 0.57) | 0.27 (−0.12; 0.55) |
| TD to 12w rolling TI | 100 ≤ PLT < 150 | 13 | 3 | 0.23 (0.08; 0.50) | 5 | 1 | 0.20 (0.04; 0.62) | 0.03 (−0.42; 0.35) |
| TD to 12w rolling TI | ITT | 58 | 24 | 0.41 (0.30; 0.54) | 27 | 5 | 0.19 (0.08; 0.37) | 0.23 (0.01; 0.39) |

Further Analysis and Characterization of the Results of the SIMPLIFY-1 and SIMPLIFY-2 are Set Forth Below:

SIMPLIFY 1 Results:

Momelotinib activity on splenomegaly: 26.5% SRR. Momelotinib was statistically non-inferior to RUX on spleen (p=0.011).

Momelotinib showed a deepened spleen response after RUX crossover. Deepening response: 46.2% spleen response (SRR) at any time in the open label phase (momelotinib arm). Post-RUX benefit: 16.5% of subjects did not achieve a spleen response on ruxolitinib but did so after 24 weeks of additional momelotinib treatment (crossover arm).

Figure 9:
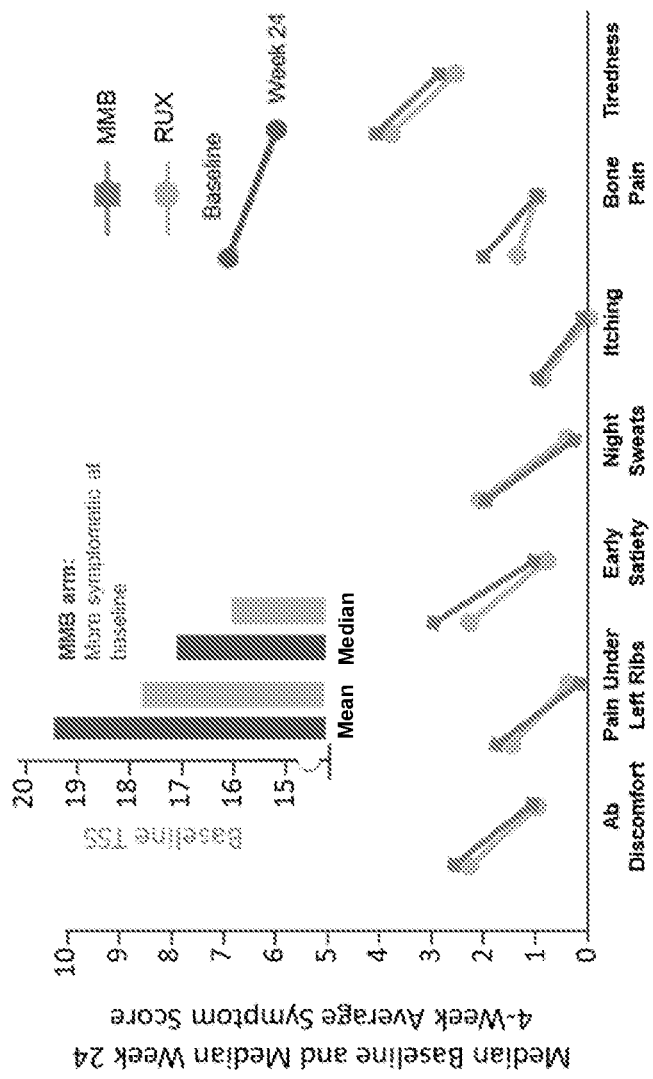
FIG. 9 shows a graph of median baseline and median week 24 average symptom score assessed as 4-week average of daily symptom scores for the 7 individual symptoms that make up the total symptom score (TSS) in the SIMPLIFY 1 trial indicating both momelotinib and ruxolitinib substantially improved all symptoms relative to baseline in a clinically comparable manner. The bar graph insert shows mean & median baseline TSS was higher in momelotinib arm vs. RUX.

FIG. 9 shows a graph of median baseline and median week 24 average symptom score assessed as 4-week average of daily symptom scores for the 7 individual symptoms that make up the total symptom score (TSS) in the SIMPLIFY 1 trial indicating momelotinib provided a clinically comparable symptom benefit to RUX. Both momelotinib and ruxolitinib substantially improved all symptoms relative to baseline in a clinically comparable manner (MMB marginally missed Total Symptom Score (TSS) non-inferiority to RUX in SIMPLIFY-1: 28.4% vs. 42.2% (Noninferior Proportion Difference 0.00 (−0.08, 0.08))). Mean & Median Baseline TSS higher in MMB vs. RUX, demonstrating the imbalance in baseline scores due to lack of stratification and which resulted in the need to achieve a greater absolute reduction in TSS in the MMB arm in order to achieve a response.

Figure 10:
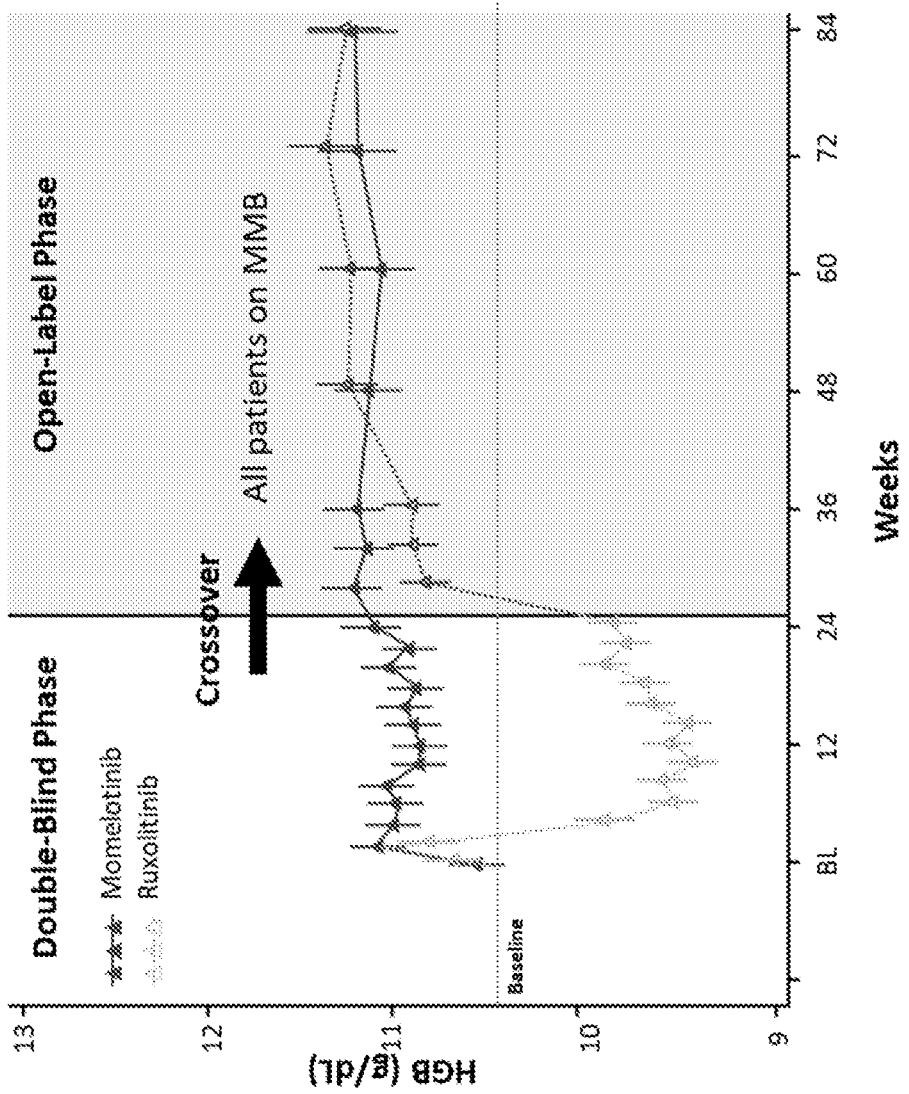
FIG. 10 shows a rapid and sustained hemoglobin improvement in patients after initiating MMB and a similar rapid and sustained hemoglobin improvement in subjects randomized to ruxolitinib after crossover to momelotinib after Week 24 in SIMPLIFY 11.

FIG. 10 shows a rapid and sustained hemoglobin improvement in patients after initiating MMB and a similar rapid and sustained hemoglobin improvement in subjects randomized to ruxolitinib after crossover to momelotinib after Week 24 in SIMPLIFY 1.

Momelotinib was well tolerated in myelofibrosis patients in the SIMPLIFY 1 trial. The anemia rate was 14% for momelotinib versus 38% for RUX. The ≥Grade 3 anemia rate was 6% for momelotinib versus 23% for RUX.

Momelotinib has a comparable overall safety profile to ruxolitinib in SIMPLIFY-1 and demonstrates substantially lower rates of thrombocytopenia and anemia. While adverse event (AE) rates were generally comparable, fewer patients experienced AEs and fewer patients experienced Grade 3 or 4 AEs on momelotinib vs. ruxolitinib.

Leukemia free survival (LFS) and overall survival (OS) trends favor momelotinib over ruxolitinib (mLFS/mOS not reached).

SIMPLIFY 2 Results:

Momelotinib showed a pronounced activity on symptoms compared to BAT (~90% ruxolitinib) in second line patients. Statistically significant symptom response (p<0.001): 26.2% TSS for momelotinib vs 5.9% for best available treatment (BAT).

LFS and OS trends favor momelotinib over best available therapy. The mOS for MMB is 28 months. Momelotinib provided noteworthy survival post-RUX when compared to historical control survival of 14 months reported in post-ruxolitinib treated patients (Newberry et al., 2017 Blood 130(9):1125-1131).

Momelotinib shows differentiated activity on anemia & transfusions. In SIMPLIFY 1, momelotinib promoted and maintained transfusion independence in 66% of patients vs. 49% for RUX. Statistically significant transfusion independent (TI) rate (p<0.001). In SIMPLIFY 2 momelotinib eliminated transfusions: 32.8% of transfusion dependent (TD) patients at baseline were TI at week 24 on momelotinib, vs. 3.7% for BAT. In SIMPLIFY 2 momelotinib promoted and maintained transfusion independence: 43% of patients were TI at week 24 on momelotinib, vs. 21% for BAT.

SIMPLIFY-1 & SIMPLIFY-2 Phase 3 Studies indicate momelotinib provided maintenance of Transfusion Independence (TI).

SIMPLIFY-1 & SIMPLIFY-2 Phase 3 Studies indicate momelotinib provided for switch from Transfusion Dependent to Independent (12 Weeks): For SIMPLIFY-1, the ≥12 week transfusion independence rate was 49.1%. For SIMPLIFY-2, the ≥12 week transfusion independence rate was 46.6%.

SIMPLIFY-1 & SIMPLIFY-2 Phase 3 Studies indicate momelotinib provided for switch from Transfusion Dependent to Independent (8 Weeks): For SIMPLIFY-1, the ≥8 week transfusion independence rate was 58.5%. For SIMPLIFY-2, the ≥8 week transfusion independence rate was 46.6%.

A combined analysis across studies of transfusion dependent to independent rates at 12 weeks/8 weeks) indicates the ≥12 week transfusion independence rate was 44.1%, and the ≥8 week transfusion independence rate was 48.7% (Combined TI response rate in TD patients from SIMPLIFY-1, SIMPLIFY-2 and '1672 (n=152). This aggregate data is representative of a continuum of Intermediate/High Risk MF patients.

TABLE 15

Momelotinib addresses the key unmet needs in MF.
MF Physician survey (2016): 60 Qualitative Interviews
(15 US; 45 EU); 240 Quantitative Surveys (100 US; 140 EU).

| MF Physician Survey: Most important MF issues to manage | US 46-51%* EU 56-59% Abdominal Pain; Fatigue | US 69% EU 76% Anemia, transfusion dependent | US 49% EU 59% Splenomegaly |
|---|---|---|---|
| | CONSTITUTIONAL SYMPTOMS | ANEMIA | SPLENOMEGALY |
| Momelotinib Benefit | Clinically comparable to ruxolitinib in 1L. Superior benefit in 2L. | Maintain Transfusion Independence. Convert Transfusion Dependence into Independence. Eliminate or decrease transfusion frequency and overall burden. Increase Hgb levels. | Equivalent to ruxolitinib in first line treatment. Clinically comparable in 2L, without RUX washout. |

*percentages indicate physician survey responses of key needs

Figure 11:
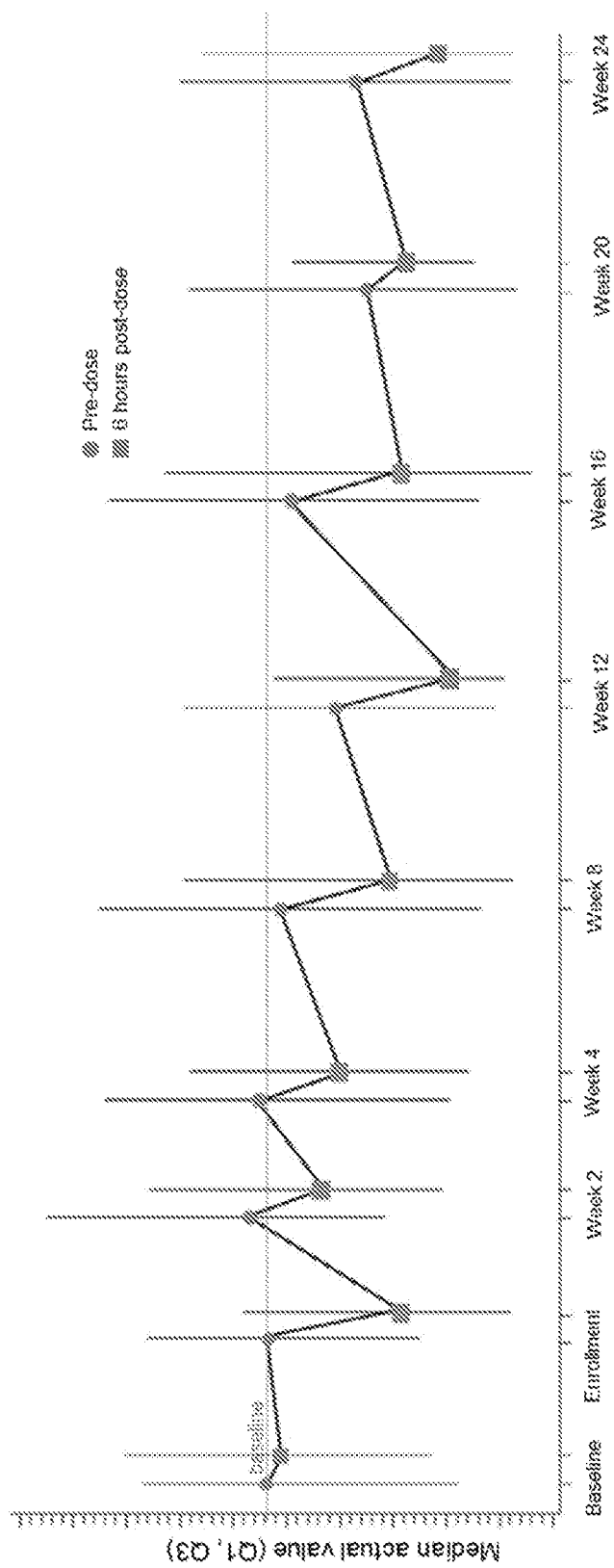
FIG. 11 is a graph illustrating momelotinib consistently decreased hepcidin post-MMB administration. In addition to the acute declines following dosing, there was also a gradual decline over the 24-week study period compared to baseline and the pre-dosing levels at enrollment. Translational biology Phase 2 study (N=41; GS-US-352-1672).

FIG. 11 is a graph illustrating momelotinib consistently decreased hepcidin post-MMB administration. Translational biology Phase 2 study (N=41; GS-US-352-1672). The 12 week transfusion independent (TI) response rate was 34%, indicating a clinically effective mechanism where ACVR1 activity and hepcidin are decreased and iron and hemoglobin increased.

Figure 13:
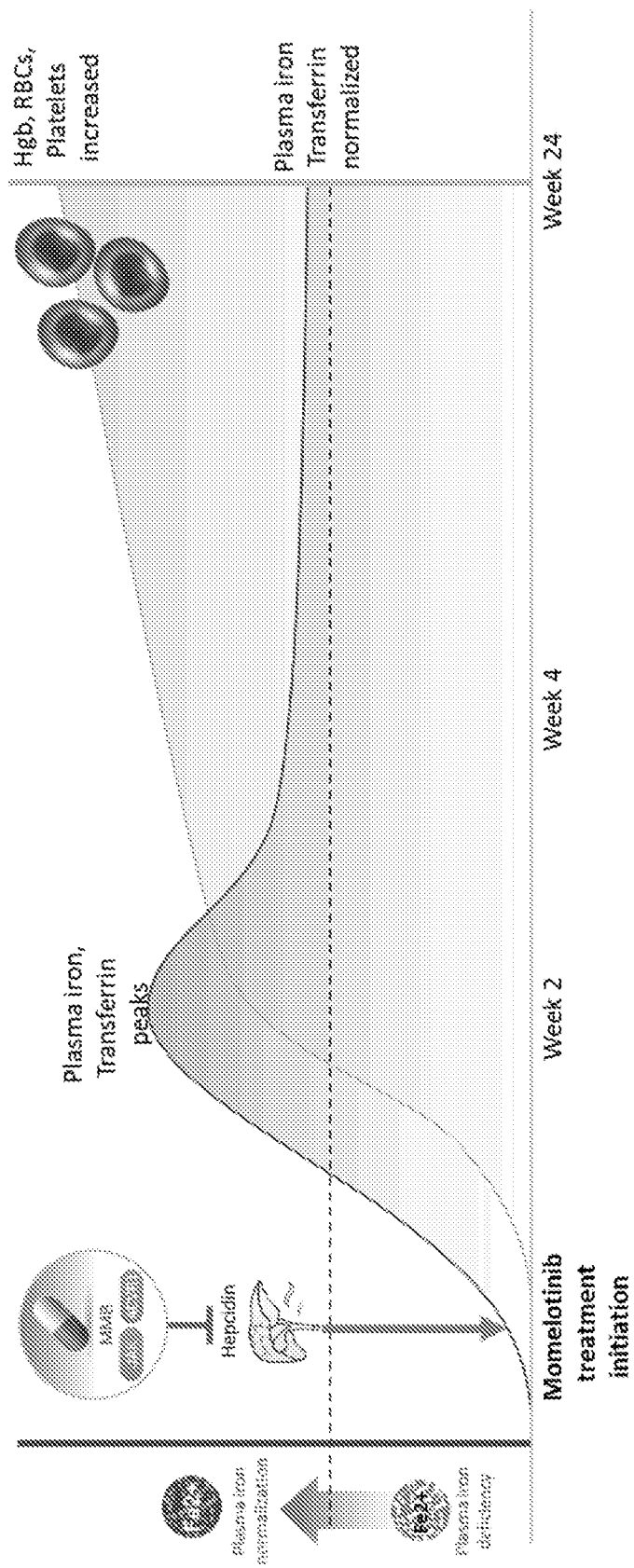
FIG. 13 is an illustrative timeline of elevated iron and hemoglobin level after momelotinib treatment initiation as supported by data from the translational biology Phase 2 study (N=41; GS-US-352-1672).

FIG. 13 is an illustrative timeline of elevated iron and hemoglobin level after momelotinib treatment initiation. Momelotinib treatment reduces hepcidin, resulting in increased serum iron and transferrin within 2 weeks, providing a bolus of iron to erythroblasts to facilitate RBC maturation. As erythropoiesis is restored, iron levels subsequently normalize while hemoglobin, RBCs and platelets continue to increase through week 24.

Translational Biology Study

In a translational biology study, we determined the impact of momelotinib on plasma hepcidin, markers of iron storage and availability, erythropoiesis, and inflammation to explore mechanisms of the favorable effects of momelotinib on MF-associated anemia and transfusion independence. See Oh et al. "Hepcidin Suppression by Momelotinib Is Associated With Increased Iron Availability and Erythropoiesis in Transfusion-Dependent Myelofibrosis Patients", Abstract #4282: Presented at ASH 60th Annual Meeting & Exposition: Dec. 1-4, 2018, San Diego, Calif., the disclosure of which is herein incorporated by reference.

Figure 12:
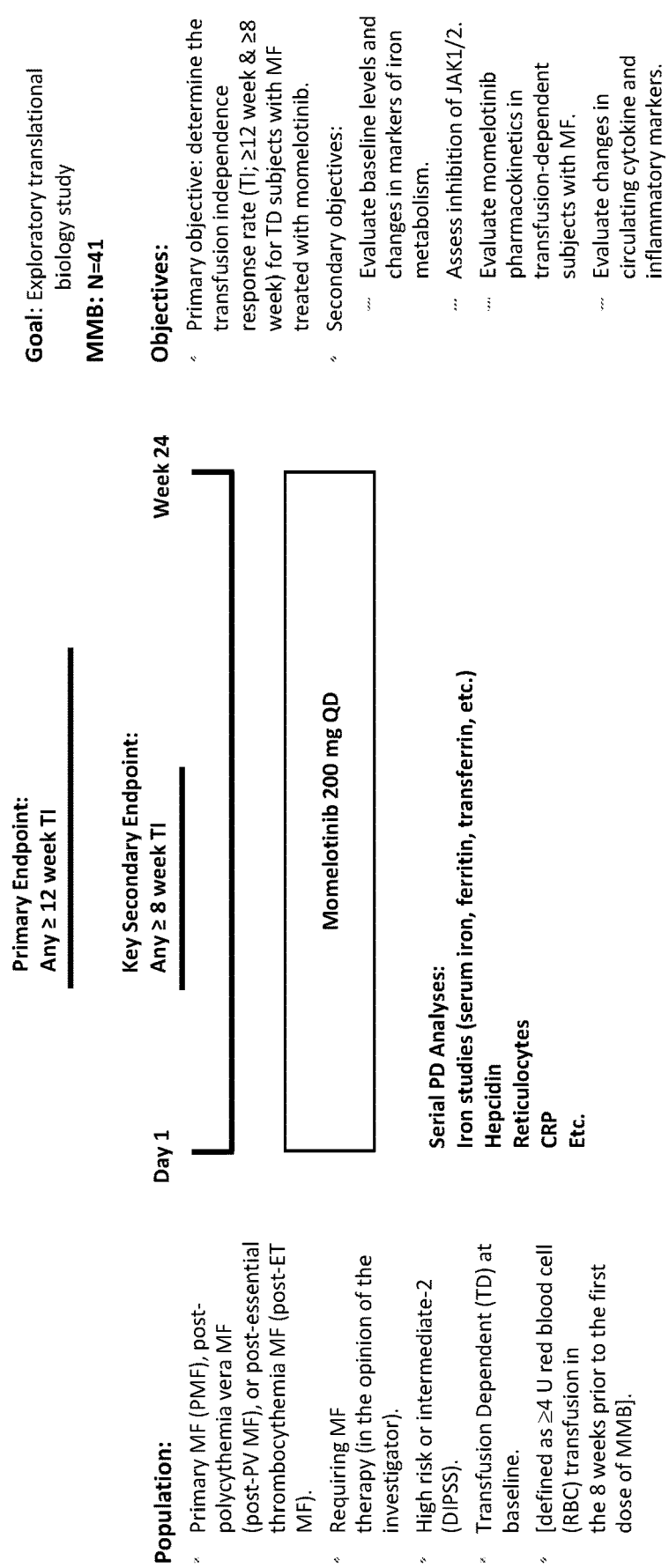
FIG. 12 shows a schematic of an exploratory translational biology study of MMB.

FIG. 12 shows a schematic of the exploratory translational biology study. Population: Primary MF (PMF), post-polycythemia vera MF (post-PV MF), or post-essential thrombocythemia MF (post-ET MF). Requiring MF therapy (in the opinion of the investigator). High risk or intermediate-2 (DIPSS). Transfusion Dependent (TD) at baseline. [defined as ≥4 U red blood cell (RBC) transfusion in the 8 weeks prior to the first dose of MMB]. Goal: Exploratory translational biology study (MMB: N=41 subjects). Objectives: Primary objective: determine the transfusion independence response rate (TI; ≥12 week & ≥8 week) for TD subjects with MF treated with momelotinib. Secondary objectives: Evaluate baseline levels and changes in markers of iron metabolism; Assess inhibition of JAK1/2; Evaluate momelotinib pharmacokinetics in transfusion-dependent subjects with MF; and Evaluate changes in circulating cytokine and inflammatory markers.

TABLE 16

A high rate of advanced (Grade 3) bone marrow fibrosis (73%) was observed in this TD population.

| Baseline Characteristic | Overall N = 41 |
|---|---|
| Age, mean (SD) years | 70 (9.0) |
| Type of MF, n (%) | |
| PMF | 32 (78.0) |
| Post-PV/ET MF | 9 (22.0) |
| Time since MF diagnosis, mean (SD) | 3.3 (2.78) |
| years RBC units transfused ≤8 weeks prior to enrollment, mean (SD) | 6 (2.3) |
| Bone marrow fibrosis grade, n (%) | |
| 0 or 1 | 2 (4.9) |
| 2 | 6 (14.6) |
| 3 | 30 (73.2) |
| DIPSS risk level, n (%) | |
| Intermediate-1/2 | 27 (65.9) |
| High | 14 (34.1) |
| Hemoglobin, mean (SD) g/dL | 8.3 (0.96) |
| <8 g/dL (%) | 29.3 |
| ≥8 g/dL (%) | 70.7 |
| Platelets, mean (SD) ×10$^3$/uL | 181 (129.9) |

Figure 14:
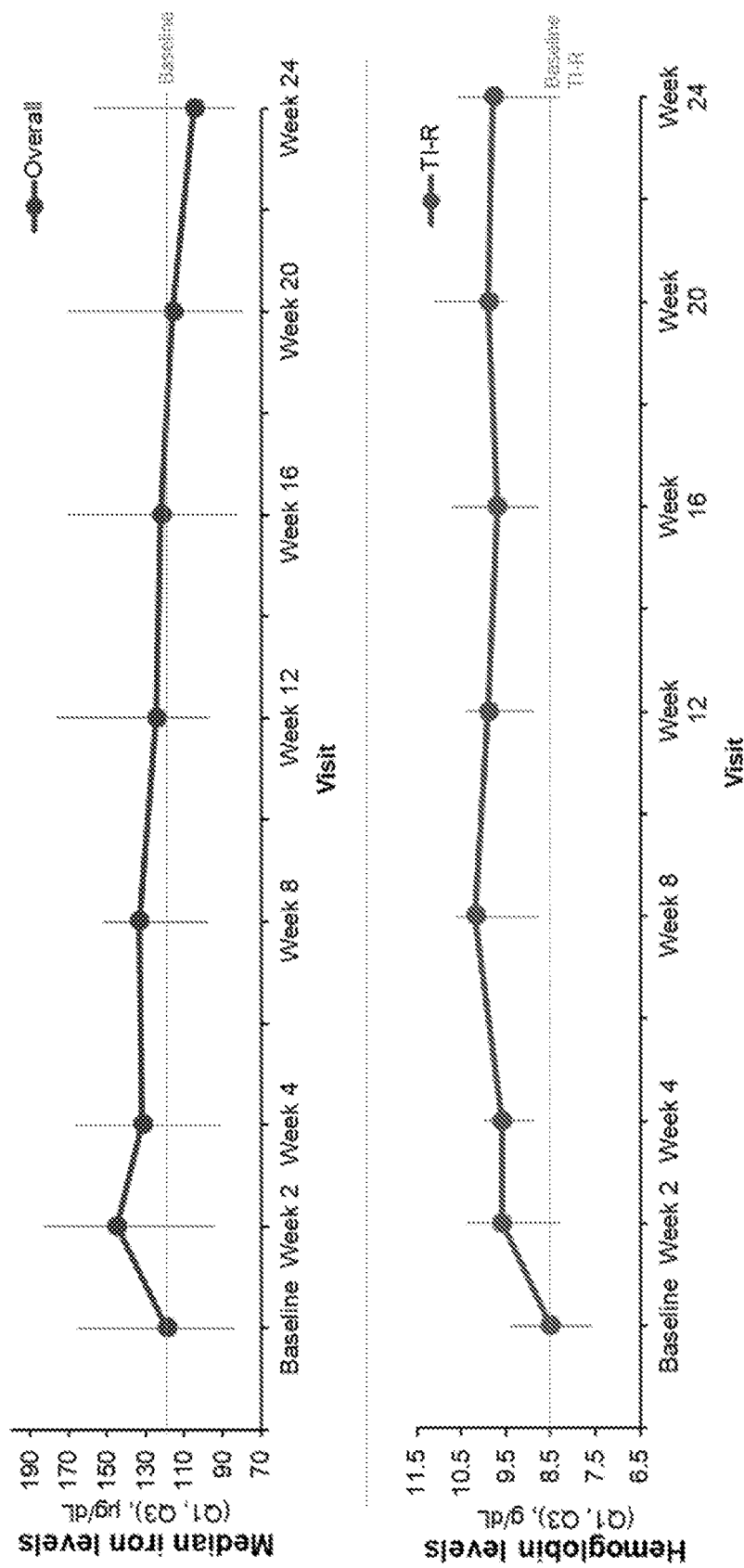
FIG. 14 shows graphs illustrating increased iron and hemoglobin levels observed overall and for transfusion independent responder (TI-R) to MMB treatment. Translational biology Phase 2 study (N=41; GS-US-352-1672).
Figure 15:
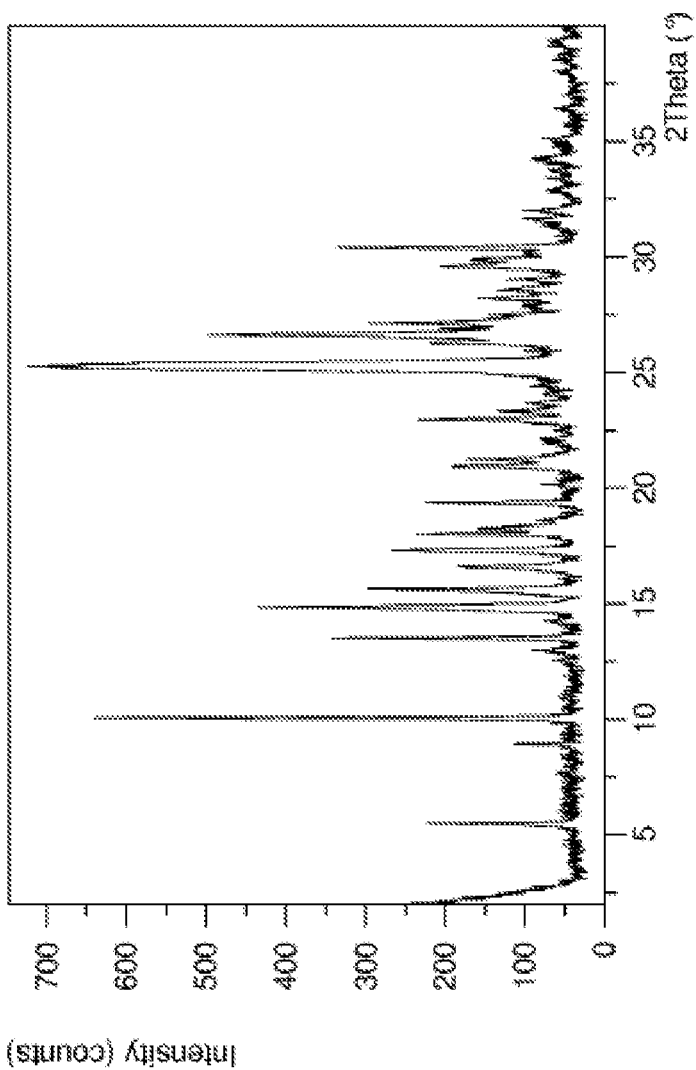
FIG. 15 shows a X-ray powder diffraction (XRPD) of momelotinib dihydrochloride anhydrous Form IV.
Figure 16:
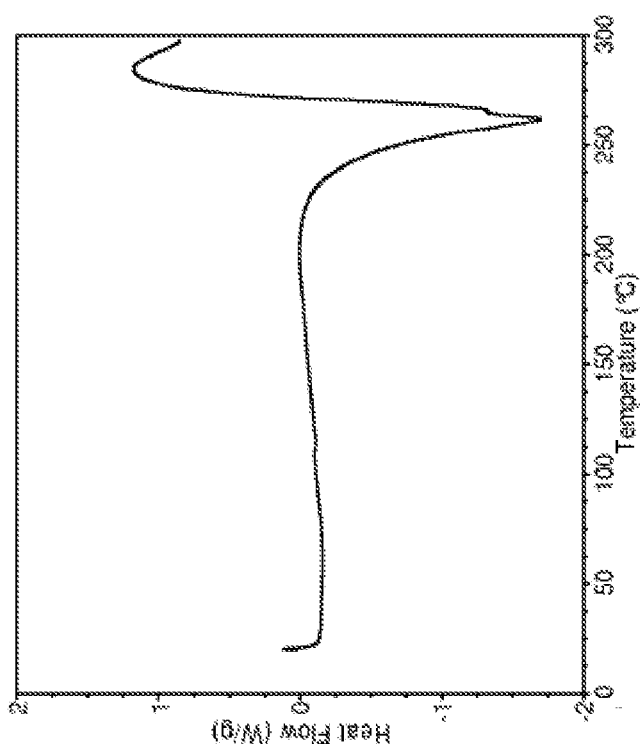
FIG. 16 shows a differential scanning calorimetry (DSC) plot for momelotinib dihydrochloride anhydrous Form IV.
Figure 17:
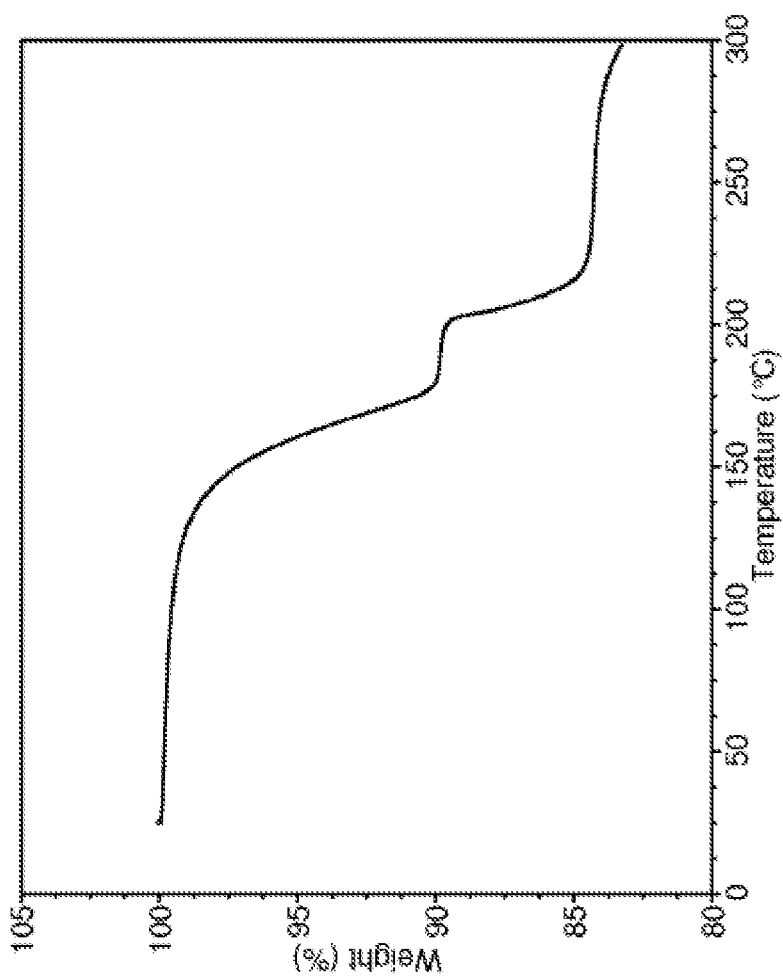
FIG. 17 shows a thermogravimetric analysis (TGA) of momelotinib dihydrochloride anhydrous Form IV.
Figure 18:
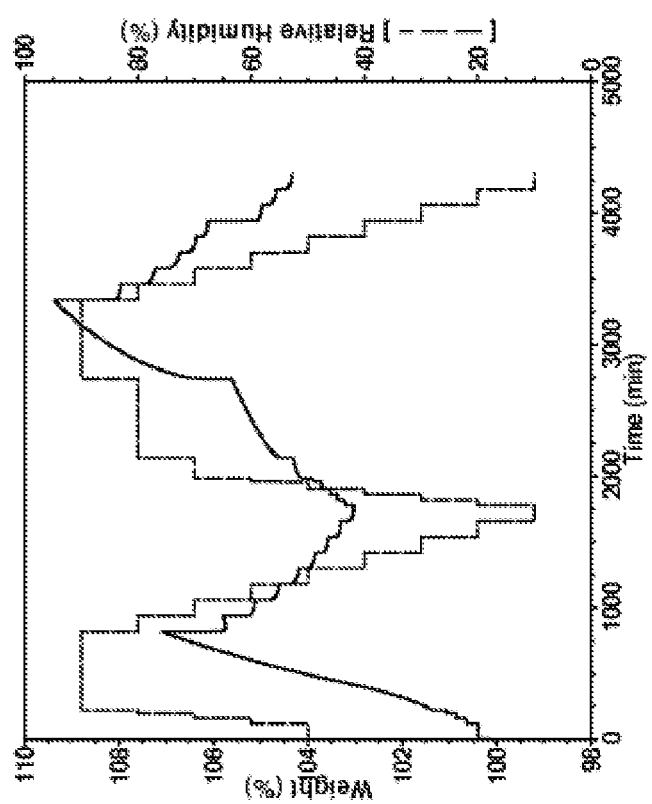
FIG. 18 shows a Dynamic Vapor Sorption (DVS) plot for momelotinib dihydrochloride anhydrous Form IV.

FIG. 14 shows graphs illustrating increased iron and hemoglobin levels observed overall and for transfusion independent responder (TI-R) to MMB treatment.

Results

Primary Endpoints: ≥12 week transfusion independence rate was 34.1%. Secondary Endpoints: ≥8 week transfusion independence rate was 39.0%.

Anemia Benefit in TI-NR Patients. Decreased transfusion burden (≥50%) in TI-NR patients was observed in 77.8% of cases for any 8 week period (units of RBC; ≥2 unit decrease).

Example 3

Dynamic and Time-to-Event Analyses Demonstrate Marked Reduction in Transfusion Requirements for Janus Kinase Inhibitor—Naïve Myelofibrosis Patients Treated with Momelotinib Compared Head to Head with Ruxolitinib Momelotinib (MMB) is a potent, selective, orally-bioavailable, small-molecule inhibitor of JAK1, JAK2 and ACVR1 being developed for the treatment of intermediate and high risk myelofibrosis (MF). Systemic inflammation integral to the pathogenesis of MF leads to increased ACVR1 activity which in turn increases secretion of hepcidin, resulting in perturbed iron homeostasis and an iron-restricted anemia (Ganz T. "Systemic Iron Homeostasis:, Physiol Rev. 2013; 93:1721-41; and Langdon J M, Yates S C, Femnou L K et al. "Hepcidin-dependent and hepcidin-independent regulation of erythropoiesis in a mouse model of anemia of chronic inflammation", Am J Hematol. 2014; 89:470-9). MMB's inhibition of ACVR1, unique amongst the JAK inhibitor (JAKi) class, leads to a reduction of hepcidin, restoring iron homeostasis and RBC production and alleviating anemia and transfusion dependency (TD). Chronic, progressive anemia is a key characteristic feature of MF; anemia and TD are strongly predictive of reduced survival (Pardanani A, Finke C, Abdelrahman R A, Lasho TL and Tefferi A. "Associations and prognostic interactions between circulating levels of hepcidin, ferritin and inflammatory cytokines in primary myelofibrosis." Am J Hematol. 2013; 88:312-6). MMB is the only clinical stage JAKi to possess potent ACVR1 inhibitory activity, resulting in improvement of anemia in contrast to ruxolitinib (RUX) which results in worsening.

The SIMPLIFY-1 (S1) trial, a double-blind, active-controlled Phase 3 study in which 432 patients received randomized treatment with MMB or RUX for 24 weeks was previously reported (Mesa R A, Kiladjian J J, Catalano J V. et al. "Simplify-1: A phase III randomized trial of momelotinib versus ruxolitinib in j anus kinase inhibitor—naïve patients with myelofibrosis", Journal of Clinical Oncology, 2017; 35:3844-50). In addition to a significant reduction in splenomegaly and improvement in constitutional symptoms, the study demonstrated that patients in the MMB arm achieved nominal-statistical significance for all anemia endpoints tested, including a higher rate of transfusion independence (p<0.001) and lower rates of TD (p=0.019) at Week 24, compared to patients on RUX, consistent with MMB's pro-erythropoietic effect. Overall, a demonstrably decreased transfusion requirement was noted in patients who received MMB vs RUX.

Since transfusion burden is of significant concern to clinicians and patients, to better understand the dynamics of RBC transfusions we further examined the S1 data through statistical models utilizing a variety of novel anemia benefit endpoints including time until transfusion and overall intensity of transfusions across time. The proportions of patients with 0 and 4 transfusions were calculated and time-to-event analyses examining time-to-first and time-to-fifth units transfused also conducted. Since transfusions typically comprise 2 units, the fifth unit transfused represents a de facto third transfusion event. The number of units transfused were also considered to be recurrent events and examined with and without patients' baseline characteristics as covariates. Finally, a mixture model, based on a zero-inflated negative binomial (ZINB) distribution fit to the transfusion data, was employed to compare between the treatment groups the proportions of subjects with zero transfusion burden and the mean transfusion rates.

Figure 29:
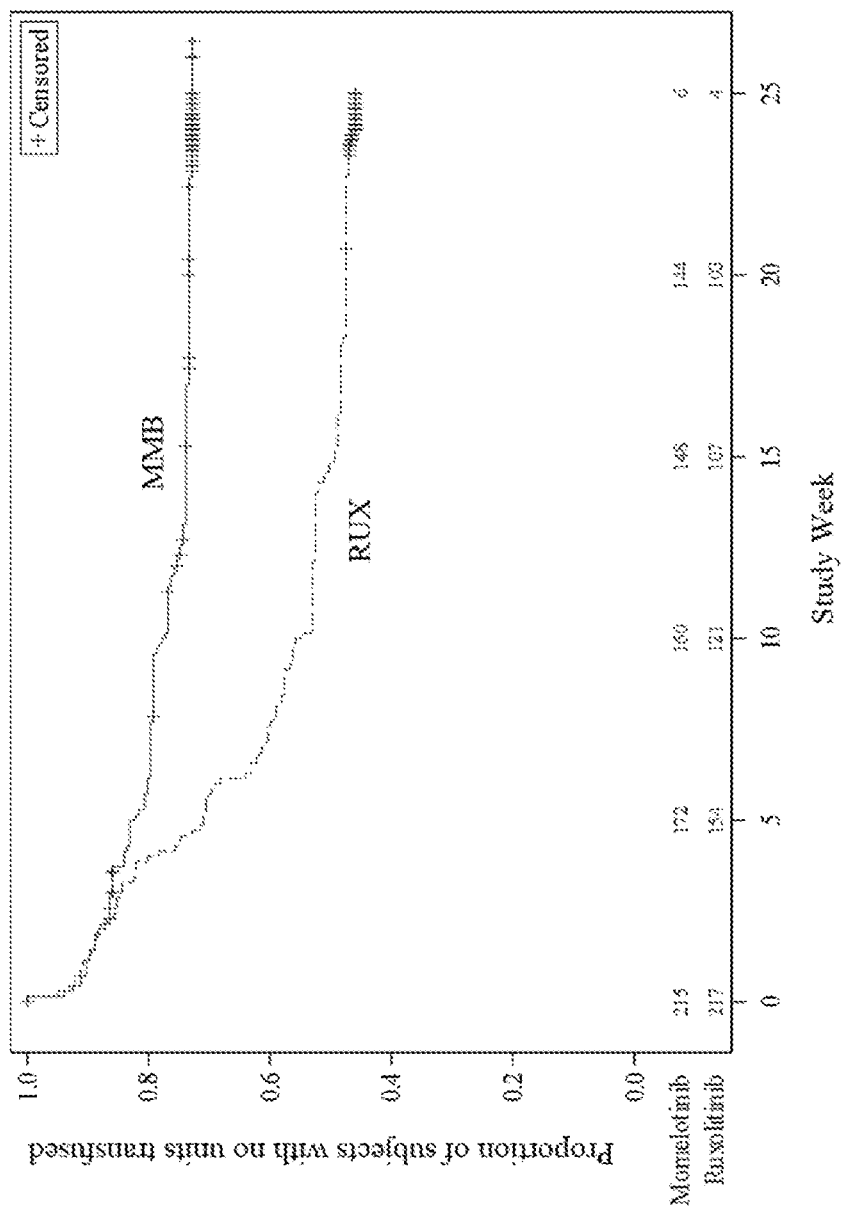
FIG. 29 shows Kaplan-Meier estimates of the proportion of patients not requiring red blood cell (RBC) transfusion during 24 weeks of RUX or MMB treatment of SIMPLIFY-1 study.
Figure 30:
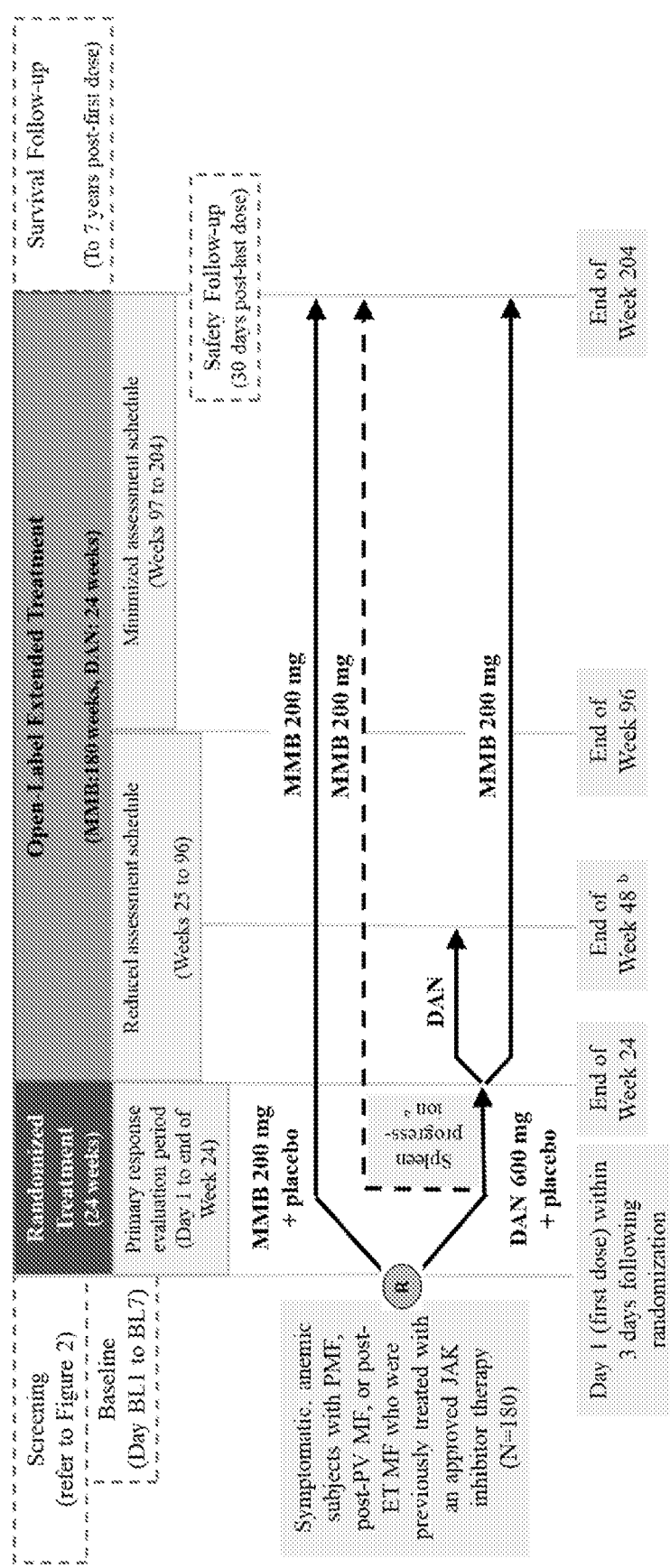
FIG. 30 shows a schematic summarizing the parameters of the MOMENTUM study of treatment of myelofibrosis using momelotinib (MMB).

Kaplan-Meier estimates of the proportion of patients who did not require any units transfused during the 24 week randomized treatment period were 73% and 46% for MMB and RUX respectively (p<0.0001; FIG. 29), while the proportion of patients requiring 4 or fewer units were 83% and 62% (p<0.0001). When examining units transfused as recurrent events, patients receiving MMB possessed a hazard ratio of approximately one-half that for patients on RUX (HR 0.522; p<0.0001) for models both with and without patients' baseline characteristics as covariates. The ZINB covariate model demonstrated that MMB increased the odds of having zero units transfused in the first 24 weeks by a factor of 9.3 (p<0.0001) vs RUX.

Taken together, the novel dynamic and time-to-event analysis methods described are relevant and informative additions to standard measures of transfusion burden in patients with MF. The results of these analyses allow more detailed description of MMB's differentiated anemia benefit as compared to RUX in a double-blind study of JAKi—naïve patients. These results when combined with additional data from the SIMPLIFY studies demonstrate that MMB is able to address the three characteristic features of MF, namely splenomegaly, constitutional symptoms and anemia, differentiating it from other JAK inhibitors.

Example 4

MOMENTUM Clinical Study

A randomized, double-blind, Phase 3 study to evaluate the activity of momelotinib (MMB) versus danazol (DAN) in symptomatic, anemic subjects with Primary Myelofibrosis (PMF), Post-Polycythemia Vera (PV) Myelofibrosis, or Post Essential Thrombocythemia (ET) Myelofibrosis who were previously treated with JAK inhibitor therapy (MOMENTUM trial) is conducted. The benefits of MMB in reducing transfusion burden are evaluated. In addition to assessment of constitutional symptoms, splenomegaly and anemia, MOMENTUM further evaluates associations between anemia benefit and patient reported measures of clinical benefit.

Momelotinib (MMB) or N-(cyanomethyl)-4-(2(4morpholinophenylamino)pyrimidin-4-yl)benzamide, dihydrochloride monohydrate is the active ingredient.

Primary Objectives: To determine the efficacy of MMB versus DAN assessed by improvement in Myelofibrosis Symptom Assessment Form v4.0 (MFSAF) total symptom score (TSS) in subjects with PMF, post-PV myelofibrosis (MF), or post-ET MF who were previously treated with approved JAK inhibitor therapy.

Secondary Objectives:
To compare the effect of MMB versus DAN on transfusion independent (TI) status at Week 24
To compare SRR for subjects treated with MMB versus DAN
To compare RBC transfusion requirements in subjects treated with MMB versus DAN
To assess the duration of MFSAF TSS response
To assess duration of TI status at Week 24
To compare the benefit of MMB versus DAN on anemia response and transfusion requirements
To compare change from baseline MFSAF TSS at Week 24 in subjects treated with MMB versus DAN
To characterize the safety of MMB
To compare the overall survival (OS) and leukemia-free survival (LFS) of subjects treated with MMB versus DAN
To assess association of MMB exposure (pharmacokinetics [PK]) with outcome
Other secondary objectives as defined by the protocol.

Exploratory objectives:
To assess time to splenic progression for subjects treated with MMB versus DAN
Other exploratory endpoints.

Trial Design:
This is a randomized, double-blind study to confirm the differentiated clinical benefit of MMB versus DAN in subjects who have previously received approved Janus kinase (JAK) inhibitor therapy for MF for a minimum of 90 days, or a minimum of 28 days if JAK inhibitor therapy was complicated by RBC transfusion requirement of ≥4 units in 8 weeks, or Grade 3/4 adverse events (AEs) of thrombocytopenia, anemia, or hematoma. Subjects must be symptomatic with a MFSAF TSS of ≥10 at Screening, and anemic with hemoglobin (Hgb)<10 g/dL.

For subjects with ongoing JAK inhibitor therapy at Screening, JAK inhibitor therapy must be tapered over a period of at least 1 week, followed by a 2-week non-treatment interval that concludes prior to Randomization. A 7-day Baseline Period (Days BL1 to BL7) is required prior to Randomization during which time daily symptom scores are captured. For subjects who have tapered and discontinued their prior JAK inhibitor, and have begun this 14-day non-treatment interval, the 7-day Baseline Period begins only after 1 week of the non-treatment interval has been completed. Day 1 of study treatment occurs within 3 days after Randomization.

Subjects orally self-administer their randomized treatment, MMB plus DAN placebo or DAN plus MMB placebo.

Subjects remain blinded to their randomized treatment assignment whenever possible. To enable decisions as to which patients are allowed to initiate open-label MMB, for example, an unblinding process must be followed. Following completion of all Week 24 assessments, subjects are given the option to receive MMB in the Open Label Extended Treatment Period, with the exception of subjects who discontinued blinded study treatment prior to the completion of Week 24 if unblinding confirmed that they were receiving MMB. Prior to Week 24, subjects discuss with the investigator or designee whether they wish to receive open-label MMB after the completion of Week 24. With the exception of subjects who discontinued early from the MMB arm, subjects may begin open-label MMB at the following timepoints and continue therapy up to the end of Week 204; a) at the end of Week 24 if they complete the Randomized Treatment Period and all Week 24 assessments; b) at the end of Week 24 if they discontinued treatment with DAN prior to the end of Week 24 but continued study assessments and did not receive prohibited medications; c) at any time during the Randomized Treatment Period if they meet the protocol-defined criteria for confirmed symptomatic splenic progression. Open-label treatment with MMB may continue up to the end of Week 204. Transition to an MMB extension study, if available, may occur once a subject has completed at least 48 weeks on-study.

Subjects randomized to receive DAN who are receiving clinical benefit at the end of Week 24 may continue open-label DAN therapy up to Week 48. The decision whether to remain on DAN or cross-over to MMB must be made by the end of Week 24.

Analysis of the primary efficacy endpoint occurs when the outcome of the primary endpoint is determinable for all subjects i.e., when each subject has completed the Randomized Treatment Period or dropped out. The maximum participation in the trial inclusive of the Screening, Randomized Treatment, Open-Label Extended Treatment, Safety Follow-Up, and Survival Follow-Up periods is approximately 7 years. During the conduct of the trial, a Data Monitoring Committee (DMC) reviews the interim progress of the clinical trial, safety data, critical efficacy endpoints, and make recommendations to the sponsor regarding the continued conduct of the study. While the DMC will be asked to advise the sponsor regarding future conduct of the study, the sponsor retains final decision-making authority on all aspects of the study.

After the Screening and Baseline Period, this trial begins with a 24-week Randomized Treatment Period, during which time data are collected for the primary analysis of efficacy. Subjects are randomized on a 2:1 basis (MMB plus DAN placebo: DAN plus MMB placebo), stratified by baseline MFSAF TSS, baseline palpable spleen length below the left costal margin, baseline RBC units transfused in the 8-week period prior to Randomization, and investigational site.

Blinded treatment (MMB plus placebo or DAN plus placebo) may be interrupted and/or reduced due to thrombocytopenia, neutropenia, non-hematologic or other toxicities according to protocol-specified criteria. Continuation of treatment at a reduced dose is preferred over treatment discontinuation, however, study treatment is discontinued if disease progression or toxicity is observed that, in the judgement of the investigator, compromises the ability to continue therapy and/or trial-specific procedures required for the safe continuation of therapy. Subjects with confirmed symptomatic splenic progression as defined per protocol or leukemic transformation, discontinue study treatment. Subjects randomized to DAN may cross-over to MMB at any time during the Randomized Treatment Period if they meet the protocol-defined criteria for confirmed symptomatic splenic progression.

If a subject discontinues treatment every attempt is made to continue all trial assessments according to the Schedule of Events (including transfusion recording, symptom assessments, and patient reported outcomes [PROs]), to the end of Week 24, and to perform follow-up procedures including Safety Follow-Up Visit and Survival Follow-Up assessments.

Only if it is not possible or acceptable to the subject or investigator for a subject to continue trial assessments after discontinuing treatment should the subject be withdrawn from the trial.

Methodology:

Screening and Baseline Assessments:

Screening activities commence after informed consent is obtained. Screening assessments include a serum pregnancy test for women of childbearing potential (WOCBP), laboratory tests (chemistry, CBC with differential, and urinalysis), virology screen, physical examination including disease-related clinical signs, vital signs, 12-lead electrocardiogram (ECG), Dynamic International Prognostic Scoring System (DIPSS, or DIPSS-plus) disease assessment, and Eastern Cooperative Oncology Group (EGOG) performance status. Recording of AEs and serious adverse events (SAEs) begin at the time of signing the informed consent form (ICF). Medical and medication history is recorded, including the last course of JAK inhibitor therapy, last spleen volume measurement, and best spleen response (response, stable disease, or splenic progression per IWG criteria) during prior therapy. Recording of concomitant medications begin, including the use of a subject-completed narcotic pain medication log. Recording of RBC transfusions begin, including pre-transfusion Hgb concentration, and documentation of whether the transfusion was given due to factors such as clinically overt bleeding, or accident/injury. Transfusion history and pre-transfusion Hgb concentrations for the period of 12 weeks prior to Randomization is gathered from subject records. Subjects are trained in the use of an ePRO device issued to them. The ePRO device is the physical hardware that is used by the patient to collect daily PRO data at home and also at study visits. To determine eligibility, the MFSAF is completed on a single day using an ePRO device at the site. For 7 consecutive days, immediately prior to Randomization, daily MFSAF assessments using an ePRO device is completed at home by the subject to determine the baseline MFSAF TSS.

At Baseline, a urine pregnancy test is performed (for WOCBP), along with laboratory tests (chemistry, CBC with differential, urinalysis, and blood samples for exploratory assessments including mutational analysis), physical examination including disease-related clinical signs, vital signs, ECOG performance status, and continued recording of AEs and SAEs, RBC transfusions, and concomitant medications. Baseline spleen length measurement for stratification is made by palpation (or ultrasound) as part of the physical examination.

In order to provide a consistent baseline assessment of spleen volume, the baseline magnetic resonance imaging (MRI) scan, or computed tomography (CT) scan if a subject is unable to have an MRI, must be performed within the following time periods: for subjects receiving any active MF therapy known to reduce spleen size at Screening (including JAK inhibitors), the scan should be performed within 1 week prior to Day 1 (within 3 days is preferable, if feasible); for subjects not receiving any active MF therapy known to reduce spleen size at the start of the Screening period, the scan should be performed within 14 days prior to the first dose of study treatment (Day 1). However, the results of the scan are not required prior to beginning study treatment.

The MFSAF baseline assessment is completed electronically using an ePRO device at home; daily assessments are completed for 7 consecutive days (Days BL1 to BL7) immediately prior to Randomization. If more than 3 daily MFSAF TSS results are missing from this 7-day assessment period, the score is considered missing and the subject should not be randomized. Therefore, it is critical if the site is notified that a subject has missed a day of baseline MFSAF that they immediately contact the subject and counsel on the importance of completing their daily assessments. If the baseline MFSAF is missing due to reasons other than subject non-compliance (e.g., technical problems with the ePRO device), the sponsor should be contacted for guidance.

Baseline assessments are also completed electronically using an ePRO device during site visit for European Organization for Research and Treatment of Cancer Quality of Life Questionnaire (EORTC QLQ-C30), Patient-Reported Outcomes Measurement Information System (PROMIS)—Physical Function, Patient Global Impression of Severity (PGIS), and EuroQoL Five Dimension (EQ-5D).

First Day of Study Treatment (Day 1):

The first dose of study treatment (Day 1) occurs within 3 days after Randomization. Subjects are required to remain for observation for a minimum of 4 hours following the first dose and anti-hypertensive therapy should not be taken on the day of the first dose until at least 4 hours after study treatment administration. Study procedures on Day 1 include dispensing of study treatment, physical exam, vital signs, ECG, ECOG performance status, and the beginning of daily MFSAF recording and daily study treatment self-administration.

Efficacy Assessments:

In order to assess transfusion status, RBC transfusion history including pre-transfusion Hgb concentration is gathered from subject records for the 12 weeks prior to Randomization, and at each visit until discontinuation. In the Randomized Treatment Period, transfusion and CBC recording occurs at least once every 4 weeks, even if the subject has discontinued therapy. In the Open-Label Extended Treatment Period, transfusion and CBC recording continues at each study visit until the end of Week 96, or discontinuation.

PRO questionnaires are completed electronically at intervals. The MFSAF is completed daily using an ePRO device throughout the Randomized Treatment Period, and for the last 7 days of each 4-week period (±7 days) from Week 25 to Week 48 in the Open-Label Extended Treatment Period. Subjects who discontinue treatment prior to Week 24 continue daily MFSAF assessments until the end of Week 24.

Clinical, laboratory, and disease assessments (including ECOG performance status and MF symptom assessment), and continued recording of RBC transfusions are completed at regular visits.

Spleen volume is assessed at the end of Week 24 and 48, and as required to confirm splenic progression.

Leukemia-free survival and OS is assessed during Survival Follow-Up.

Safety Assessments: Recording of AEs and SAEs begin at the time of signing the ICF and continue until 30 days after the last dose of study treatment. Concomitant medications, laboratory tests (chemistry, CBC with differential, and urinalysis), urine pregnancy tests, 12-lead ECGs, physical examinations (including spleen length measurements by palpation or ultrasound), and vital signs are completed at visits.

Exploratory Assessments: Additional exploratory data is collected at various timepoints.

Pharmacokinetic Assessments: Blood samples for PK analysis are collected at various timepoints.

Number of Subjects: Initially 180 subjects, which may be increased to the maximum of 270.

Diagnosis and Main Criteria for Inclusion:

Symptomatic, anemic subjects with PMF, post-PV MF, or post-ET MF who were previously treated with approved JAK inhibitor therapy.

Inclusion Criteria:
1. Age≥18 years
2. Confirmed diagnosis of PMF in accordance with the World Health Organization (WHO) 2016 criteria, or Post-PV/ET MF in accordance with the International Working Group-Myeloproliferative Neoplasms Research and Treatment (IWG-MRT) criteria
3. Symptomatic, defined as a MFSAF TSS of ≥10 units assessed by a single MFSAF v4.0 assessment at Screening visit
4. Anemic, defined as any of the following:
   For any subject; having received a transfusion within 28 days prior to the first day of Baseline assessments (BL1), with pre-transfusion Hgb<10 g/dL, or
   For subjects without ongoing JAK inhibitor therapy at Screening; Hgb<10 g/dL during the Baseline Period (Days BL1 to Day BL7), or
   For subjects receiving ongoing JAK inhibitor therapy at Screening; Hgb<10 g/dL during Screening, prior to beginning of JAK inhibitor taper
5. Previously treated, with an approved JAK inhibitor for PMF or Post-PV/ET MF for ≥90 days, or ≥28 days if JAK inhibitor therapy is complicated by RBC transfusion requirement of ≥4 units in 8 weeks, or Grade 3/4 AEs of thrombocytopenia, anemia, or hematoma
   Subjects who discontinued JAK inhibitor therapy prior to Screening require no additional non-treatment interval
   For subjects with ongoing JAK inhibitor therapy at Screening, JAK inhibitor therapy must be tapered over a period of at least 1 week, and a non-treatment interval begin 7 days prior to Day BL1 (the first of 7 consecutive days of baseline MFSAF assessments)
6. Baseline splenomegaly, defined as having a palpable spleen at ≥5 cm, below the LCM, or with volume≥450 cm³ on imaging (ultrasound, MRI or CT are acceptable), assessed during Screening at any point prior to Randomization
7. High risk, intermediate-2, or intermediate-1 risk as defined by DIPSS, or DIPSS-plus
8. No allogeneic stem cell transplant planned
9. Acceptable laboratory assessments:

| | |
|---|---|
| ANC | ≥0.75 × 10⁹/L |
| PLT | ≥25 × 10⁹/L |
| Peripheral blast count | <10% |
| AST/SGOT and ALT/SGPT | ≤3 × ULN (≤5 × ULN if liver is involved by extramedullary hematopoiesis as judged by the investigator or if related to iron chelator therapy that was started within the prior 60 days) |
| Calculated creatinine clearance | ≥30 mL/min (According to Cockcroft-Gault calculation) |
| Direct bilirubin | ≤2.0 × ULN |

ANC—absolute neutrophil count, ALT/SGPT—alanine aminotransferase/serum glutamic-pyruvic transaminase, AST/SGOT—alanine aminotransferase/glutamic-oxaloacetic transaminase, PLT—platelet count 10. Eastern Cooperative Oncology Group (ECOG) performance status of 0, 1, or 2
11. Life expectancy>24 weeks
12. Able to understand and willing to sign the ICF
13. Willing and able to complete PRO assessments using an ePRO device according to protocol
14. WOCBP, men with partners of childbearing potential, and subjects with pregnant or lactating partners must agree to follow the contraceptive requirements of the clinical trial protocol, effective from the first administration of MMB, throughout the trial and for 6 months after the last dose of MMB.

Exclusion Criteria:
1. Use of the following treatments within the time periods noted (criteria a-i):
   a. MMB at any time
   b. JAK inhibitor therapy within 2 weeks prior to Randomization (refer to inclusion criterion #5)
   c. Active anti-MF therapy within 2 weeks prior to Randomization. Supportive care including steroids for non-MF indications may be used
   d. Potent cytochrome P450 3A4 (CYP3A4) inducers within 1 week prior to Randomization
   e. Investigational agent within 4 weeks prior to Randomization
   f. Erythropoiesis stimulating agent (ESA) within 4 weeks prior to Randomization
   g. Danazol within 3 months prior to Randomization
   h. Splenic irradiation within 3 months prior to Randomization
   i. Current treatment with simvastatin, atorvastatin, lovastatin or rosuvastatin
2. History of prostate cancer, with the exception of localized prostate cancer that has been treated surgically or by radiotherapy with curative intent and presumed cured
3. Prostate specific antigen (PSA)>4 ng/mL
4. Unsuitable for spleen volume measurements due to prior splenectomy or unwilling or unable to undergo an MM or CT scan for spleen volume measurement
5. Any of the following (criteria a-k):
   a. Uncontrolled intercurrent illness including, but not limited to: active uncontrolled infection (subjects receiving outpatient antibacterial and/or antiviral treatments for infection that is under control or as infection prophylaxis may be included in the trial)
   b. Significant active or chronic bleeding event≥Grade 2 per Common Terminology Criteria for Adverse Events (CTCAE) v5.0, within 4 weeks prior to Randomization
   c. Unstable angina pectoris within 6 months prior to Randomization d. Symptomatic congestive heart failure within 6 months prior to Randomization
e. Uncontrolled cardiac arrhythmia within 6 months prior to Randomization
f. QTcF interval>500 msec, unless attributed to bundle branch block
g. Current progressive thrombosis despite treatment
h. History of *porphyria*
i. Child-Pugh score≥10
j. Psychiatric illness, social situation, or any other condition that would limit compliance with trial requirements or may interfere with the interpretation of study results, as judged by investigator or sponsor
k. Inability or unwillingness to comply with the protocol restrictions on MF therapy and other medications prior to and during study treatment
6. Subjects with a prior or concurrent malignancy, whose natural history or treatment has a significant potential to interfere with the safety or efficacy assessment of the investigational regimen
7. Known clinically significant anemia due to iron, vitamin B12, or folate deficiencies, or autoimmune or hereditary hemolytic anemia, or gastrointestinal bleeding
8. Known positive status for HIV
9. Chronic active or acute viral hepatitis A, B, or C infection, or hepatitis B or C carrier (testing required for hepatitis B and C)
10. Unresolved non-hematologic toxicities from prior therapies that are >Grade 1 per CTCAE v5.0
11. Presence of peripheral neuropathy≥Grade 2 per CTCAE v5.0
12. Women who are already pregnant or lactating
13. Known intolerance or hypersensitivity to MMB or DAN, their metabolites, or formulation excipients.
14. Patients with rare hereditary problems of galactose intolerance, Lapp lactase deficiency or glucose-galactose malabsorption. Note: DAN capsules contain lactose.

Investigational Product, Reference Therapy, and Placebo Dosage and Mode of Administration:

MMB plus DAN placebo or DAN plus MMB placebo is orally self-administered, without regard to food, at approximately the same times each day. The starting dose of MMB is 200 mg; preferably administered in the morning. The starting dose of DAN is 600 mg total daily dose. Blinded treatment and open-label treatment with MMB or DAN may be tapered, if appropriate, and interrupted and/or reduced due to thrombocytopenia, neutropenia, or other toxicities according to protocol-specified criteria.

The starting MMB dose in this trial is 200 mg. This dose has resulted in clinical improvements in splenomegaly, constitutional symptoms, and anemia benefit, and was well tolerated over an extended use period with no significant drug related safety concerns observed in the Phase 3 SIMPLIFY studies. The starting DAN dose in this trial is 600 mg total daily dose. Subjects continuing open-label DAN treatment to Week 48 receive a reduced dose of 400 mg total daily dose, and may be progressively reduced to the minimum dose necessary to maintain the response. The dose of study treatment is reduced due to treatment-related toxicities.

Duration of Treatment:

The Randomized Treatment Period has a duration of 24 weeks. Open-label extended treatment with MMB (for those randomized to MMB) or cross-over to treatment with MMB (for those randomized to receive DAN) may continue up to end of Week 204, i.e., a total period of treatment of approximately 4 years. The maximum participation in the trial inclusive of The Screening, Randomized Treatment, Open-Label Extended Treatment, and Follow-Up periods are approximately 7 years.

Transition to an MMB extension study, if available, may occur once a subject has completed at least 48 weeks on-study.

Criteria for Evaluation:

Primary Endpoint:

The MFSAF TSS response rate at Week 24. TSS response rate is defined as the proportion of subjects who achieve a ≥50% reduction in TSS over the 28 days immediately prior to the end of Week 24 compared to baseline.

TABLE 17

Primary Objective and Endpoint

| Primary Objective | Primary Endpoint |
| --- | --- |
| To determine the efficacy of MMB versus DAN assessed by improvement in MFSAF TSS in subjects with PMF, post-PV MF, or post-ET MF who were previously treated with approved JAK inhibitor therapy | Difference in MFSAF TSS response rate at Week 24. TSS response is defined as the proportion of subjects who achieve a ≥50% reduction in TSS over the 28 days immediately prior to the end of Week 24 compared to baseline |

Secondary Endpoints (Abbreviated):

Proportion of subjects with TI status at the end of Week 24; defined as not requiring RBC transfusion (except in the case of clinically overt bleeding) for ≥12 weeks immediately prior to the end of Week 24, with Hgb level≥8 g/dL. Assessed in all subjects SRR; defined as the proportion of subjects who have splenic response (reduction in spleen volume of ≥35% from baseline) at the end of Week 24

Other secondary endpoints include: measures of anemia benefit and duration of response, mean change from baseline MFSAF TSS, safety assessments, survival analyses, change from baseline in PROs, and plasma concentration of MMB.

Exploratory Endpoints (Abbreviated):

Exploratory endpoints include time to splenic progression and other endpoints.

Definitions

Myelofibrosis Symptom Assessment Form Total Symptom Score (MFSAF TSS):
Symptomatic: MFSAF TSS of ≥10 units assessed by MFSAF v4.0 at Screening visit.
Baseline MFSAF TSS: Average of the daily MFSAF TSS for the period of 7 consecutive days (Days BL1 to BL7) immediately prior to Randomization.
MFSAF TSS response: ≥50% reduction in MFSAF TSS at Week 24, i.e., the average of the daily TSS from the consecutive 28-day period prior to the end of Week 24, compared to baseline.

Splenic Response and Progression:
Splenic response: ≥35% spleen volume reduction from baseline.
Confirmed splenic progression: defined as meeting both of the following criteria:
Worsening of early satiety with weight loss≥Grade 2 (ie, ≥10% from baseline), or worsening of sustained splenic pain following either:

2 consecutive weeks of daily narcotic pain medication, or

≥50% increase from baseline in the daily dose of narcotic pain medication.

Increase in spleen volume≥15% from baseline (additional magnetic resonance imaging [MM] or computed tomography [CT] scan is performed to confirm splenic progression).

Anemia:

Anemic: defined for the purpose of study eligibility as any of the following:

For any subject; having received a transfusion within 28 days prior to the first day of Baseline assessments (BL1), with pre-transfusion Hgb<10 g/dL, or For subjects without ongoing JAK inhibitor therapy at Screening; Hgb<10 g/dL during the Baseline Period (Days BL1 to Day BL7), or For subjects receiving ongoing JAK inhibitor therapy at Screening; Hgb<10 g/dL during Screening, prior to beginning of JAK inhibitor taper Baseline Hgb level: Last observed Hgb prior to Randomization, unless a RBC transfusion was received within 28 days in which case the pre-transfusion (up to 7 days prior to transfusion) Hgb value is used.

Baseline RBC transfusion requirement: number of units of RBC transfusion required per month; determined from number of RBC transfusions given in the 8-week period prior to Randomization (note: transfusion history is collected for the period of 12 weeks prior to Randomization).

Transfusion independent (TI): not requiring RBC transfusion (except in the case of clinically overt bleeding) for ≥12 weeks, with Hgb level≥8 g/dL.

Transfusion dependent (TD): requiring RBC transfusion≥4 units in the 8 weeks prior to Randomization. Only RBC transfusions given when Hgb levels are ≤9.5 g/dL are counted towards TD. RBC transfusions given for clinically overt bleeding, or accident/injury (as assessed by the investigator) are not counted towards TD.

Transfusion requiring (TR): not meeting TD or TI criteria.

Duration of TI response: the number of days from the first day of the 12-week period over which TI status was established, to the first RBC transfusion (except in the case of clinically overt bleeding) or Hgb level<8 g/dL.

Conversion to TI status: For subjects who were TD or TR at baseline, loss of requirement for RBC transfusion (except in the case of clinically overt bleeding) for ≥12 weeks, with Hgb level≥8 g/dL.

Conversion to TD status: For subjects who were TI or TR at baseline, the development of a requirement for ≥4 RBC units in an 8-week period prior to Week 24 (and Week 48 for MMB arm).

Rate of RBC transfusion: the average number of RBC units per month not associated with clinically overt bleeding, or accident/injury.

Leukemic Transformation:

Leukemic transformation: a bone marrow blast count of ≥20% or peripheral blood blast content of ≥20% associated with an absolute blast count of ≥1×10$^9$/L that lasts for ≥2 weeks.

Criteria for Adjustment or Stopping Doses

Blinded treatment (MMB plus placebo or DAN plus placebo) and open-label treatment with MMB or DAN is interrupted and/or reduced due to thrombocytopenia, neutropenia, or other toxicities. During the Randomized Treatment Period, doses of both components of the study treatment i.e., MMB plus placebo or DAN plus placebo is reduced in the event of toxicity according to protocol-specified criteria below.

Continuation of study treatment at a reduced dose is preferred over treatment discontinuation. Dose reduction is by sequential dose decrements, except in the case of non-hematologic or other toxicities. Treatment may be interrupted for up to 28 days, inclusive of taper, and restarted as described in the following sections. If toxicity persists beyond 28 days, treatment may be restarted upon sponsor approval. If toxicity recurs, additional treatment interruptions may be made and sequential dose reductions may be applied if treatment is resumed. Re-escalation is allowed upon resolution of toxicity or return to baseline grade.

TABLE 18

Study Treatment Dose Reduction

| | MMB total daily dose (mg) | DAN total daily dose (mg) |
|---|---|---|
| Starting dose (mg/day) | 200 | 600 |
| Dose Decrement 1 | 150 | 400 |
| Dose Decrement 2 | 100 | 300 |
| Dose Decrement 3 | 50 | 200 |

Dose Adjustments for Thrombocytopenia

Platelet counts are monitored throughout the study and the study treatment dose adjusted based on degree of thrombocytopenia. Re-escalation is allowed upon resolution of toxicity or return to baseline grade, at the investigator's discretion.

Splenic Progression, Leukemic Transformation, and Disease Progression

Subjects with confirmed symptomatic splenic progression or leukemic transformation discontinue study treatment. Subjects randomized to DAN who discontinue due to confirmed symptomatic splenic progression may cross-over to open-label treatment with MMB.

Study treatment is discontinued if disease progression or toxicity is observed that, in the judgement of the investigator, compromises the ability to continue therapy and/or trial specific procedures required for the safe continuation of therapy.

Study Treatment Cross-Over

Prior to Week 24, subjects discuss with the investigator or designee whether they wish to receive open-label MMB after completing all Week 24 assessments. Following the completion of all Week 24 assessments, subjects are able to receive MMB in the Open Label Extended Treatment Period, providing they are not restricted from doing so according to the trial criteria.

Subjects who are willing and able to receive open-label MMB may begin open-label MMB at the following time-points and continue therapy up to the end of Week 204:

At the end of Week 24 if they complete the Randomized Treatment Period and all Week 24 assessments.

At the end of Week 24 if they discontinued treatment with DAN prior to the end of Week 24, but continued study assessments and did not receive prohibited medications At any time during the Randomized Treatment Period if they meet the protocol-defined criteria for symptomatic splenic progression and it is confirmed they were receiving randomized treatment with DAN as per the unblinding process.

At completion of the Randomized Treatment Period including all Week 24 assessments, subjects who choose to receive open-label MMB, and are not restricted by protocol from doing so, begin treatment at the 200 mg starting dose, unless during the Randomized Treatment Period the dose of study treatment was reduced for suspected MMB associated toxicity. Dose re escalation is allowed upon resolution of toxicity or return to baseline grade, at the investigator's discretion, to a maximum daily dose of 200 mg MMB.

Subjects randomized to receive DAN who are receiving clinical benefit at the end of Week 24 and do not to cross-over to MMB may continue open-label DAN therapy up to Week 48 at a maximum total daily dose of 400 mg. Subjects who were receiving a reduced dose of DAN during the Randomized Treatment Period should remain on the reduced dose. During open-label treatment with DAN, the dose may be progressively reduced to the minimum dose necessary to maintain the response. Subjects who choose not to continue to open-label MMB or DAN discontinue study treatment.

The MOMENTUM trial is a randomized, double-blind, Phase 3 study to evaluate the activity of momelotinib (MMB) versus danazol (DAN) in symptomatic, anemic subjects with Primary Myelofibrosis (PMF), Post-Polycythemia Vera (PV) Myelofibrosis, or Post Essential Thrombocythemia (ET) Myelofibrosis who were previously treated with JAK inhibitor therapy (MOMENTUM trial). The results of the Phase 3 study confirm clinical benefits of MMB (e.g., as described above) in reducing transfusion burden, and constitutional symptoms, splenomegaly and anemia. Associations between anemia benefit and patient reported measures of clinical benefits are confirmed by the results of the Phase 3 study.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of treating myelofibrosis in a subject, the method comprising:
    administering a therapeutically effective amount of momelotinib or a pharmaceutically acceptable salt thereof to a subject identified as having (i) myelofibrosis and (ii) a baseline platelet count of less than $50 \times 10^9$/L.

2. The method of claim 1, wherein the baseline platelet count is a baseline platelet count determined within one week prior to initiation of momelotinib therapy, wherein the subject had not been treated with previous JAK inhibitor therapy for at least 2 weeks prior to momelotinib therapy.

3. The method of claim 1, wherein the subject has previously been treated with a JAK inhibitor.

4. The method of claim 3, wherein the subject has previously been treated with ruxolitinib.

5. The method of claim 4, wherein the subject is an adult human who has had an inadequate response to or is intolerant of ruxolitinib or wherein the subject failed to respond or ceased to respond to previous ruxolitinib therapy.

6. The method of claim 3, wherein the subject has previously been treated with fedratinib.

7. The method of claim 6, wherein the subject is an adult human who has had an inadequate response to or is intolerant of fedratinib or wherein the subject failed to respond or ceased to respond to previous fedratinib therapy.

8. The method of claim 1, wherein the subject is naïve to JAK inhibitor therapy.

9. The method of claim 1, wherein the myelofibrosis is intermediate, intermediate-2, or high-risk myelofibrosis.

10. The method of claim 1, wherein the myelofibrosis is primary myelofibrosis (PMF) or post-polycythemia vera or post-essential thrombocythemia myelofibrosis (Post-PV/ET MF).

11. The method of claim 1, wherein the momelotinib or a pharmaceutically acceptable salt thereof is administered orally.

12. The method of claim 1, wherein the momelotinib or a pharmaceutically acceptable salt thereof is administered once daily.

13. The method of claim 1, wherein the therapeutically effective amount is between 50 mg/day and 200 mg/day.

14. The method of claim 1, wherein the subject has thrombocytopenia or neutropenia.

15. The method of claim 14, wherein the subject has thrombocytopenia.

16. The method of claim 15, wherein the therapeutically effective amount of momelotinib is about 200 mg/day, about 150 mg/day, about 100 mg/day, or about 50 mg/day.

17. The method of claim 15, wherein the therapeutically effective amount of momelotinib, or a pharmaceutically acceptable salt thereof, is administered in a first dose of about 200 mg, and subsequent doses of about 150 mg.

18. The method of claim 15, wherein the therapeutically effective amount of momelotinib, or a pharmaceutically acceptable salt thereof, is administered in a first dose of about 200 mg, a second dose of about 150 mg, and subsequent doses of about 100 mg.

19. The method of claim 15, wherein the therapeutically effective amount of momelotinib, or a pharmaceutically acceptable salt thereof, is administered in a first dose of about 200 mg, a second dose of about 150 mg, a third dose of about 100 mg, and subsequent doses of about 50 mg.

20. The method of claim 15, wherein the therapeutically effective amount of momelotinib, or a pharmaceutically acceptable salt thereof, is administered in a first dose of about 200 mg and subsequent doses decreased in 50 mg increments.

21. The method of claim 15, comprising administering not less than 50 mg/day of momelotinib, or a pharmaceutically acceptable salt thereof.

* * * * *